US010036683B2

(12) United States Patent
Moldover et al.

(10) Patent No.: US 10,036,683 B2
(45) Date of Patent: Jul. 31, 2018

(54) ACOUSTO-MICROWAVE SYSTEM FOR DETERMINING MASS OR LEAK OF GAS IN A VESSEL AND PROCESS FOR SAME

(71) Applicant: THE UNITED STATES OF AMERICA, AS REPRESENTED BY THE SECRETARY OF COMMERCE, Washington, DC (US)

(72) Inventors: Michael R. Moldover, Bethesda, MD (US); Keith A. Gillis, Washington Grove, MD (US); James B. Mehl, Orcas, WA (US)

(73) Assignee: THE GOVERNMENT OF THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 160 days.

(21) Appl. No.: 15/188,211

(22) Filed: Jun. 21, 2016

(65) Prior Publication Data

US 2016/0370327 A1 Dec. 22, 2016

Related U.S. Application Data

(60) Provisional application No. 62/182,729, filed on Jun. 22, 2015.

(51) Int. Cl.
*G01N 21/00* (2006.01)
*G01M 3/24* (2006.01)
*G01N 29/036* (2006.01)

(52) U.S. Cl.
CPC ............ *G01M 3/24* (2013.01); *G01N 29/036* (2013.01); *G01N 2291/014* (2013.01); *G01N 2291/02809* (2013.01); *G01N 2291/02881* (2013.01)

(58) Field of Classification Search
CPC ............ H01L 27/124; G02F 1/136209; G01N 21/1702; G01N 1/24; G01N 29/024;
(Continued)

(56) References Cited

U.S. PATENT DOCUMENTS

| 7,408,456 B2* | 8/2008 | Whitesmith .......... G01S 13/751 340/500 |
| 2010/0164488 A1* | 7/2010 | Lowe .................... G01N 29/12 324/239 |

OTHER PUBLICATIONS

L. Pitre et al., Progress Towards an Acoustic/Microwave Determination of the Boltzmann Constant at LNE_INM/CNAM, International Journal of Thermo Physics, 2008, 1730-1739, vol. 29.
(Continued)

*Primary Examiner* — Manish S Shah
*Assistant Examiner* — Nigel Plumb
(74) *Attorney, Agent, or Firm* — Office of Chief Counsel for National Institute of Standards and Technology

(57) ABSTRACT

An acousto-microwave system to determine a mass M of gas disposed in a vessel includes: a microwave transmitter disposed on the vessel to transmit microwave radiation inside the vessel, a portion of the microwave radiation occurring at a microwave resonance of the vessel; a microwave receiver disposed on the vessel to receive microwave radiation communicated through an interior of the vessel from the microwave transmitter; an acoustic transmitter disposed on the vessel to transmit acoustic radiation inside the vessel, a portion of the acoustic radiation occurring at an acoustic resonance of the gas in the vessel; and an acoustic receiver disposed on the vessel to receive acoustic radiation communicated through the gas from the acoustic transmitter. The mass M of the gas is determined by analyzing the microwave radiation received by the microwave receiver and the acoustic radiation received by the acoustic receiver.

16 Claims, 24 Drawing Sheets

(58) Field of Classification Search
CPC ........... G01N 29/036; G01N 2291/014; G01N 2291/02809; G01N 2291/02881; G01M 3/24; H05B 6/64; H05B 6/80
USPC .......................................................... 257/72
See application file for complete search history.

(56) References Cited

OTHER PUBLICATIONS

M.R. Moldover et. al., Acoustic gas thermometry, Metrologia, 2014, R1-R19, vol. 51.
Moldover, M.R., et al., Microwave determination of the volume of a pressure vessel, Measurement Science and Technology, 2015, 26.

* cited by examiner

ACOUSTO-MICROWAVE SYSTEM FOR DETERMINING MASS OR LEAK OF GAS IN A VESSEL AND PROCESS FOR SAME

CROSS REFERENCE TO RELATED APPLICATIONS

This application claims the benefit of U.S. Provisional Patent Application Ser. No. 62/182,729, filed Jun. 22, 2015, the disclosure of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is an acousto-microwave system to determine a mass M of gas disposed in a vessel, the acousto-microwave system comprising: a microwave transmitter disposed on the vessel to transmit microwave radiation inside the vessel, a portion of the microwave radiation occurring at a microwave resonance of the vessel; a microwave receiver disposed on the vessel to receive microwave radiation communicated through an interior of the vessel from the microwave transmitter; an acoustic transmitter disposed on the vessel to transmit acoustic radiation inside the vessel, a portion of the acoustic radiation occurring at an acoustic resonance of the gas in the vessel; and an acoustic receiver disposed on the vessel to receive acoustic radiation communicated through the gas from the acoustic transmitter.

Further disclosed is a process for determining a mass M of a gas disposed in a vessel, the process comprising: subjecting an interior of the vessel with microwave radiation transmitted by a microwave transmitter disposed on the vessel, a portion of the microwave radiation occurring at a microwave resonance of the vessel; communicating the microwave radiation through an interior of the vessel; receiving, by a microwave receiver disposed on the vessel, the microwave radiation communicated through the interior of the vessel; transmitting, by an acoustic transmitter disposed on the vessel, acoustic radiation; subjecting the gas disposed in the vessel with the acoustic radiation transmitted by the acoustic transmitter, a portion of the acoustic radiation occurring at an acoustic resonance of the gas in the vessel; and communicating the acoustic radiation through the gas disposed in the vessel; receiving, by an acoustic receiver disposed on the vessel, the acoustic radiation communicated through the gas disposed in the vessel; and analyzing the microwave radiation received by the microwave receiver and the acoustic radiation received by the acoustic receiver to determine the mass M of the gas disposed in the vessel.

Additionally disclosed is a process for detecting a leak of a gas disposed in a vessel, the process comprising: determining a pressure p of the gas disposed in the vessel; transmitting, by an acoustic transmitter disposed on the vessel, acoustic radiation inside the vessel; subjecting the gas in the vessel to acoustic radiation; receiving, by an acoustic receiver disposed on the vessel, acoustic radiation communicated through the gas from the acoustic transmitter; determining an acoustic frequency of an acoustic resonance $f_a$ of the gas based on the acoustic radiation received by the acoustic receiver; and combining the pressure of the gas and the acoustic frequency of the acoustic resonance $f_a$ of the gas to detect the leak of the gas disposed in the vessel according to a decrease in $p/(f_a)^2$.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that an acousto-microwave system herein uses microwave techniques that are scalable to very large volumes to determine an interior volume of a vessel. The microwave techniques provide a determination of the volume of the vessel in an absence of thermostatting the vessel and are scalable to an arbitrary size of the vessel, which does not result in increased uncertainty or cost. Further, the acousto-microwave system determines the mass M of gas disposed in the vessel by combining a measured pressure p of the gas, measured microwave resonance frequency, measured acoustic resonance frequency, and an accurate equation of state of the gas. Also, the resonance frequencies can be used to weigh a gas in a vessel that is made, e.g., from a ferromagnetic steel at a high pressure in a non-thermostatted environment. Accordingly, the acousto-microwave system has many applications in gas metrology. Advantageously, the acousto-microwave system detects a leak of the gas from the vessel by determining a time dependence of the ratio pressure p of the gas in the vessel to the acoustic resonance frequency, i.e., $p/f_a^2$, wherein $f_a$ is a resonance frequency of an acoustic mode of the gas inside the vessel, and p is the pressure of the gas.

Figure 1:
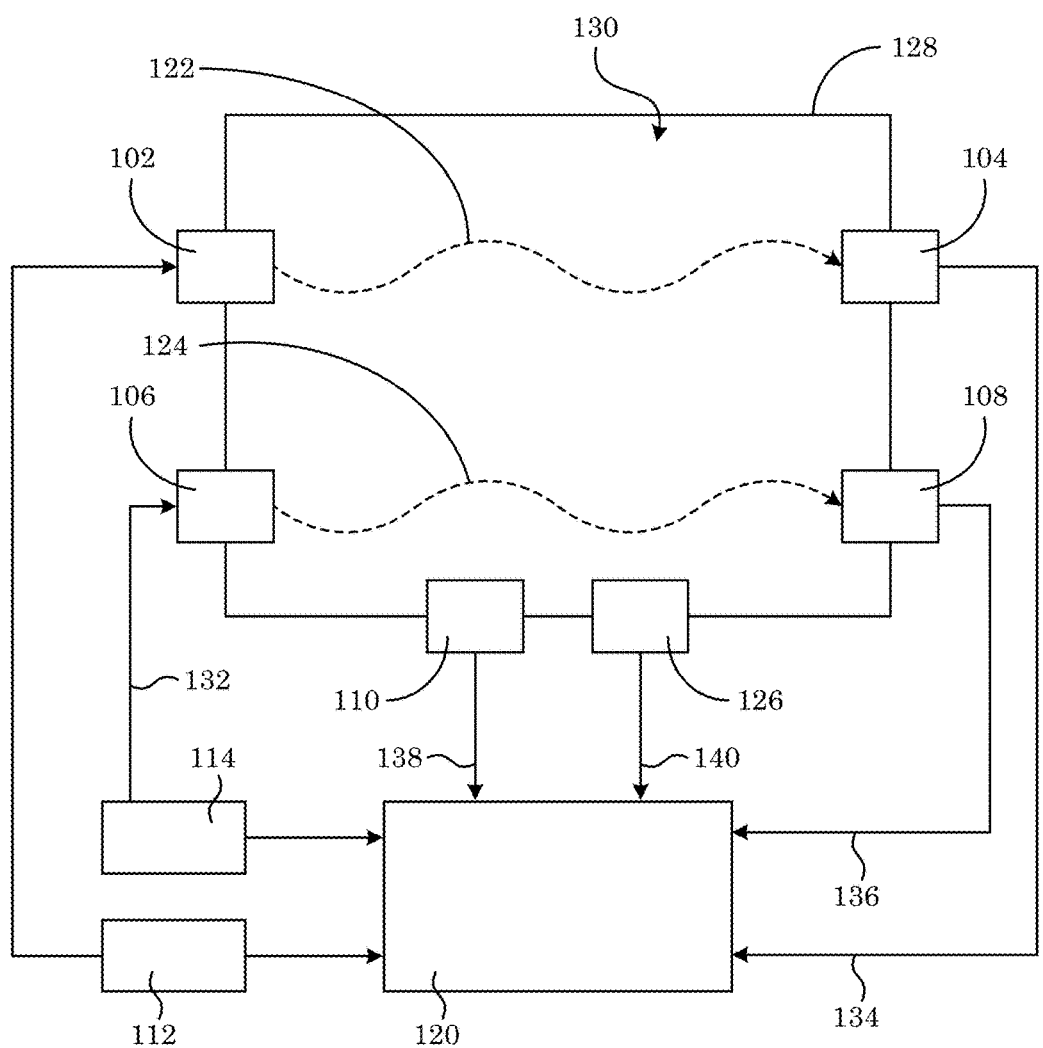
FIG. 1 shows an acousto-microwave system.

In an embodiment, with reference to FIG. 1, acousto-microwave system 100 includes microwave transmitter 102 disposed on vessel 128 to transmit microwave radiation 122 inside vessel 128 in which a portion of microwave radiation 122 occurs at a microwave resonance of vessel 128 and from which a volume of vessel 128 is determined. Acousto-microwave system 100 also includes microwave receiver 104 disposed on vessel 128 to receive microwave radiation 122 communicated through interior 130 of vessel 128 from microwave transmitter 106. Acoustic transmitter 106 is disposed on vessel 128 and provided to transmit acoustic radiation 124 inside vessel 128, wherein a portion of acoustic radiation 124 occurs at an acoustic resonance of the gas in vessel 128 and from which an average temperature of the gas disposed in vessel 128 is determined. Acousto-microwave system 100 also includes acoustic receiver 108 disposed on vessel 128 to receive acoustic radiation 124 communicated through the gas from acoustic transmitter 106. Pressure meter 110 also is disposed on vessel 128 to provide a pressure of the gas in vessel 128.

Acousto-microwave system 100 can include microwave source 112 in electrical communication with microwave transmitter 102, wherein microwave source 112 provides microwave radiation 122 to microwave transmitter 102 prior to transmission of microwave radiation 122 inside vessel 128. Acoustic driver 114 can be disposed in in electrical communication with acoustic transmitter 106 to control acoustic transmitter 106 for production of acoustic radiation 124 by acoustic transmitter 106 in response to an acoustic control signal 132 provided to acoustic transmitter 106 from acoustic driver 114. An optional temperature probe 126 can be disposed on vessel 128 to provide a temperature of vessel 128, for diagnostic purposes, in a selected location.

In some embodiments, acousto-microwave system 100 includes processor 120 in electrical communication optionally and independently with microwave transmitter 102, microwave receiver 104, acoustic transmitter 106, acoustic receiver 108, pressure meter 110, microwave source 112, acoustic driver 114, temperature probe 126, and the like. Processor 120 receives microwave data 134 from microwave receiver 104, acoustic data 136 from acoustic receiver 108, pressure data 138 from pressure meter 110, or temperature data from temperature probe 126. Processor 120 determines mass M of the gas disposed in vessel 128 based on microwave data 134, acoustic data 136, pressure data 138, temperature data 140, or a combination thereof. In a particular embodiment, processor 120 determines a volume of vessel 128 from microwave data 134 and determines a speed of sound in the gas from acoustic data 136. Without wishing to be bound by theory, it is believed that the mass M of the gas is determined by processor 120 according to formula (1)

$$M = \rho(p, u)V \approx \frac{\gamma_0 pV}{u^2}\left[1 + (\beta_\alpha - B)\frac{p}{RT}\right], \qquad (1)$$

wherein M is the mass of the gas in vessel 128; ρ is the density of the gas; $\gamma_0$ is a zero-pressure heat-capacity ratio that is equal to $C_p/C_v$, wherein $C_p$ is a constant pressure heat capacity of the gas, and $C_v$ is the constant volume heat capacity of the gas; p is the pressure of the gas; V is the volume of vessel 128; u is the speed of sound in the gas; $\beta_\alpha$ is an acoustic virial coefficient of the gas; B is a density virial coefficient of the gas; R is an ideal gas constant; and T is an average temperature of the gas in vessel 128. The approximation on the right-hand-side of formula (1) is valid at low pressure such that the second term in the square brackets is small compared to unity.

Processor 128 can also be in electrical communication with microwave source 112 or acoustic driver 114 to receive data about a frequency, power, or the like, of microwave radiation 122 and acoustic control signal 132.

Microwave transmitter 102 is provided to transmit microwave radiation 122 from which the volume of interior 130 of vessel 128 can be determined. Microwave transmitter 102 is selected to transmit microwave radiation 122 and can be a microwave purpose-built antenna, a loop at the end of coaxial cable or a straight extension of the center conductor of a coaxial cable and the like that has a selected shape or size. The selected shape or size can depend on a geometry (e.g., a shape, size, material, and the like) of vessel 128. The shape of microwave transmitter 102 can be a straight wire that generates the electric field of the microwaves or a loop that generates the magnetic field of the microwaves. A length of microwave transmitter 102 can be from less than 1% of the microwave wavelength to 10% of the microwave wavelength or even more. However, antennas that are too large compared with the microwave wavelength may distort the microwave fields and lead to inaccurate determinations of the mass of gas in the vessel.

A frequency of microwave radiation 122 produced by microwave transmitter 102 can be selected to excite a microwave mode of vessel 128 such that a peak as a function of the microwave frequency occurs in the amplitude of the detected microwave signal at the microwave receiver. in response to being subjected with microwave radiation 122 from microwave transmitter 102. The frequency of microwave radiation 122 can be from the ratio of the speed of light in vacuum to the one-half of the longest dimension of the vessel to ten or more times the ratio of the speed of light in vacuum to the one-half of the longest dimension of the vessel. If the microwave frequency is too low, no peaks will be detected; if the frequency is too high, overlapping peaks will be detected and they will reduce the accuracy of the determination of the mass of the gas in the vessel. More specifically, the frequencies of the resonances can be determined by solving Maxwell's equations for the internal shape of the vessel using well-established numerical and/or analytical techniques. A power of microwave radiation can be any convenient value, but is typically chosen such that the detected microwave amplitude is well above the noise. A typical value is one milliwatt.

In an embodiment, microwave source 112 is in electrical communication with microwave transmitter 102 and provides microwave radiation 122 to microwave transmitter 102. Microwave source 112 produces a selected frequency and amplitude (e.g., power) of microwave radiation 122 and can provide modulation to microwave radiation 122 such as amplitude modulation, frequency modulation, and the like having a selected period and duty cycle. Further, microwave source 112 can be in electrical communication with controller 120 to provide controller 120 with information (e.g., frequency, amplitude, and the like) about microwave radiation 122 provided to microwave transmitter 102.

Microwave receiver 104 is provided to receive microwave radiation 122 transmitted in interior 130 of vessel 128 that is transmitted from microwave transmitter 102. Microwave receiver 104 can be a microwave antenna similar to the microwave transmitter 102. The selected shape or size can depend on a geometry (e.g., a shape, size, material, and the like) of vessel 128. A length of microwave receiver 104 can be chosen to be the same as the transmitter.

Microwave receiver 104 can be the same as or different from microwave transmitter 102. With regard to a mutual arrangement or disposition of microwave transmitter 102 and microwave receiver 104 on vessel 128, they can be well separated such as being disposed on opposite ends of vessel 128. By separating transmitter 102 and receiver 104 by a large distance, it the microwave energy can unintentionally pass directly from transmitter 102 to receiver 104 without passing through vessel 128. However, microwave transmitter 102 or microwave receiver 104 do not have to be disposed in a specific place on vessel 128.

Acoustic transmitter 106 is provided to transmit acoustic radiation 124 inside vessel 128 from which the mass of the gas disposed in interior 130 of vessel 128 can be determined. Acoustic transmitter 106 is selected to produce and transmit acoustic radiation 124 and can be a transducer such as a piezoelectric crystal or ceramic, coil-in-magnet loud speaker or earphone, or capacitor loud speaker or earphone and the like that has a selected shape or size. The selected shape or size can depend on a type of gas (e.g., a hydrocarbon gas, halogenated gas, and the like) in vessel 128. Exemplary transducers include piezoelectric loud speakers. A shape of acoustic transmitter 106 can be a circular disk. A frequency of acoustic radiation 124 produced by acoustic transmitter 106 can be selected to interact with the gas disposed in interior 130 such that a peak as a function of the acoustic frequency occurs in the amplitude of the sound detected by the acoustic receiver 108 in response to being subjected with acoustic radiation 124 from acoustic transmitter 106. The frequency of acoustic radiation 124 can be from tens of hertz to several kilohertz, depending upon the size of the vessel 128 with larger vessels requiring lower frequencies. A power of acoustic radiation 124 can be from milliwatts to tens of watts.

Figure 2:
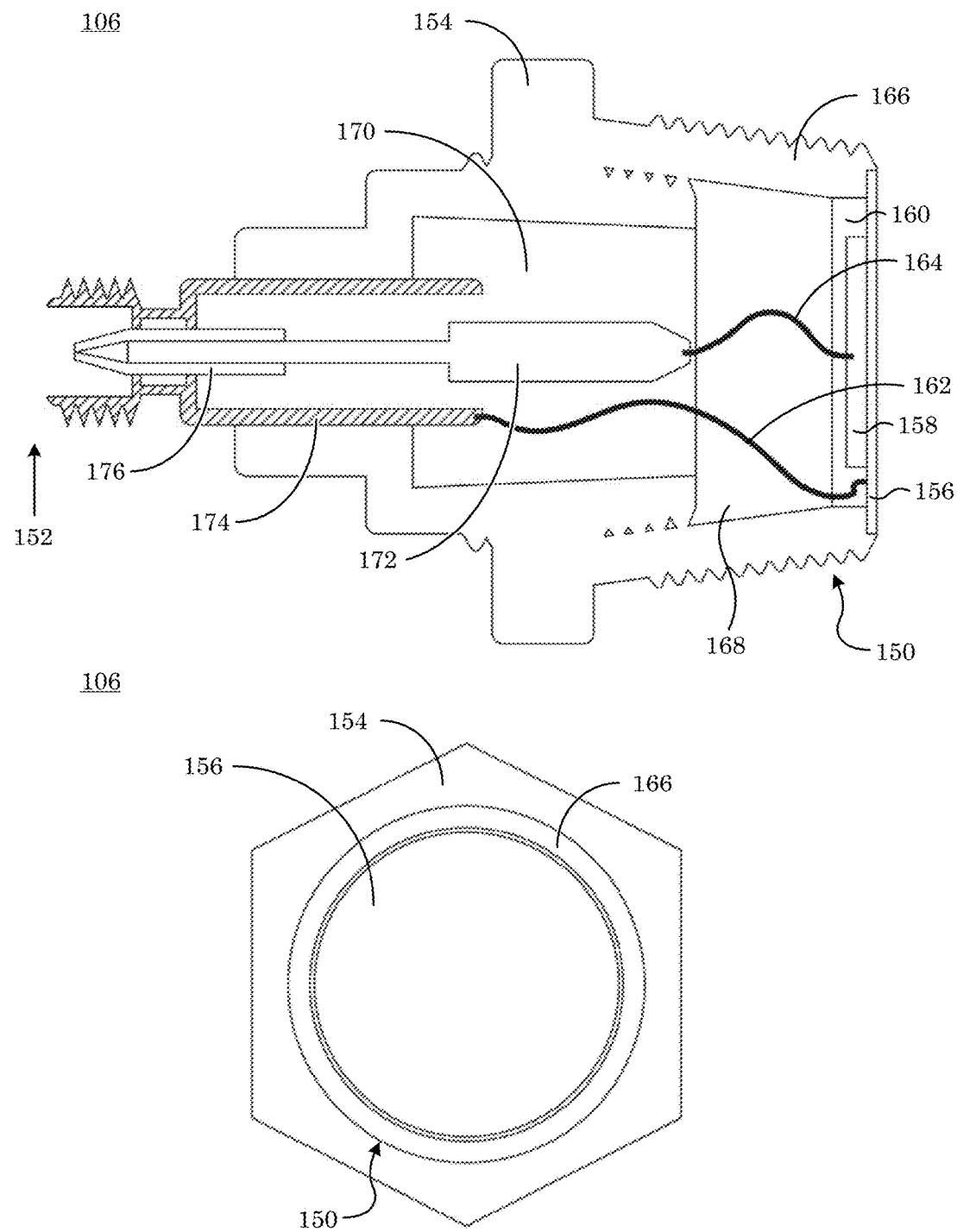
FIG. 2 shows an acoustic transmitter.

In an embodiment, with reference to FIG. 2, acoustic transmitter 106 includes metal diaphragm 156 driven by an attached piezoceramic disk 158 disposed at first end 150, NPT (National Pipe Thread Taper, a U.S. standard for tapered threads defined by ANSI/ASME B1.20.1) male thread 166 disposed at first end 150, pressure release hole 155 that traverses through a side of male thread 166 to equalize pressure across diaphragm 156. A space behind diaphragm 160 was filled with glass wool 168 to dampen a Helmholtz resonance. Source signal lead 164 was soldered to center contact 172, and ground lead 162 was soldered to shield contact 174 of hermetic, grounded, coaxial SMA feed-through 152 with coaxial contact 176. Shield contact 174 was silver soldered to NPT cored plug 153. PTFE tape can be used to seal threads of the two pipe fittings. Also included is NPT cored plug 153, NPT reducer 154, NPT male thread 166, and internal gas volume 170.

Acoustic receiver 108 is provided to receive acoustic radiation 124 that is communicated through the gas disposed in interior 130 of vessel 128 from which the speed of sound in the gas can be determined. Acoustic receiver 108 is selected to receive acoustic radiation 124 and can be a transducer such as a piezoelectric crystal or ceramic, an electromagnetic (dynamic) microphone, a condenser microphone, and the like that has a selected shape or size. The selected shape or size can depend on a type of gas (e.g., a hydrocarbon gas, halogenated gas, and the like) in vessel 128. Exemplary transducers include piezoceramic and electret condenser microphones. A shape of acoustic receiver 108 can be a disk or a cylindrical cartridge.

Figure 3:
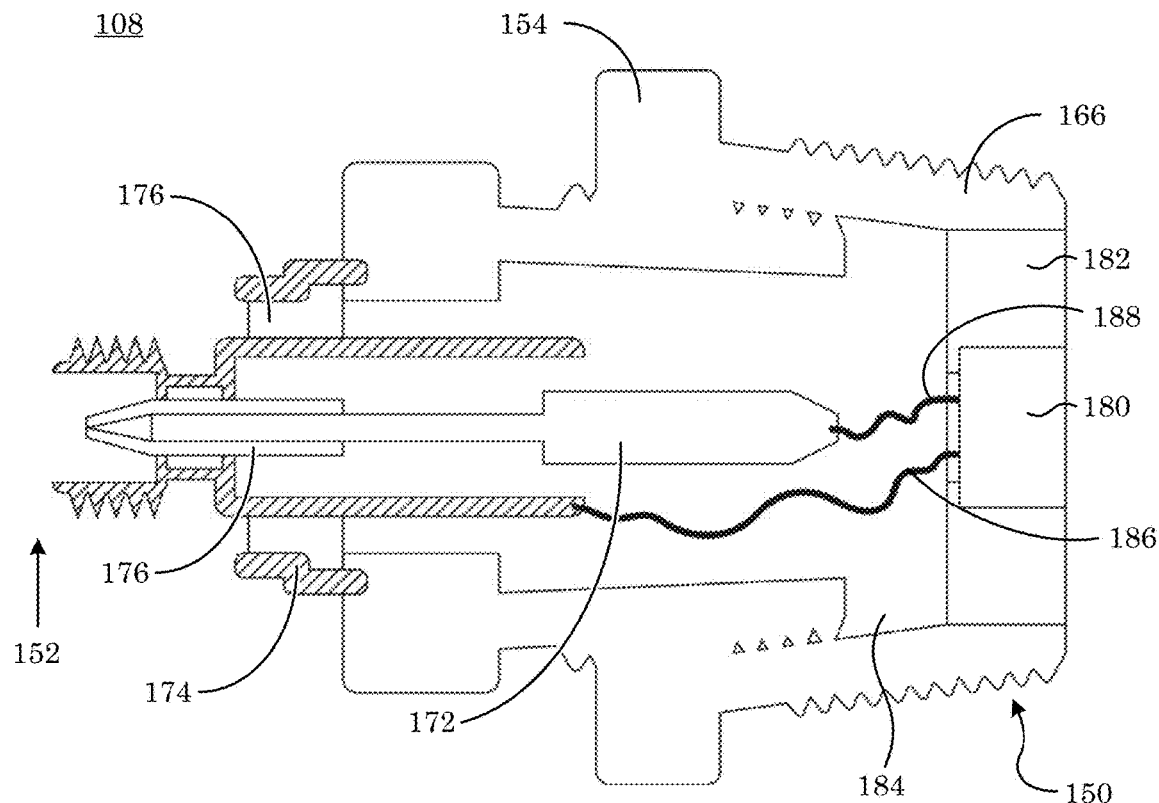
FIG. 3 shows an acoustic receiver.
Figure 3:
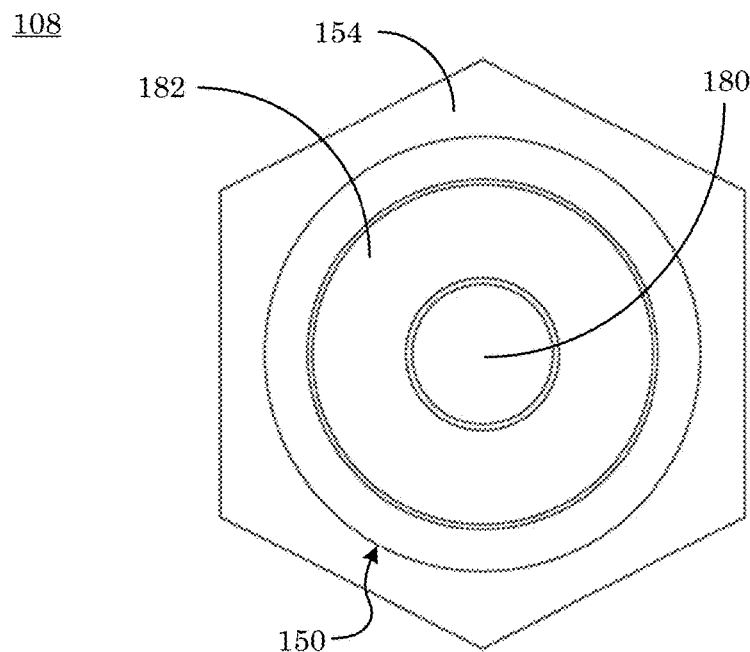
Figure 4:
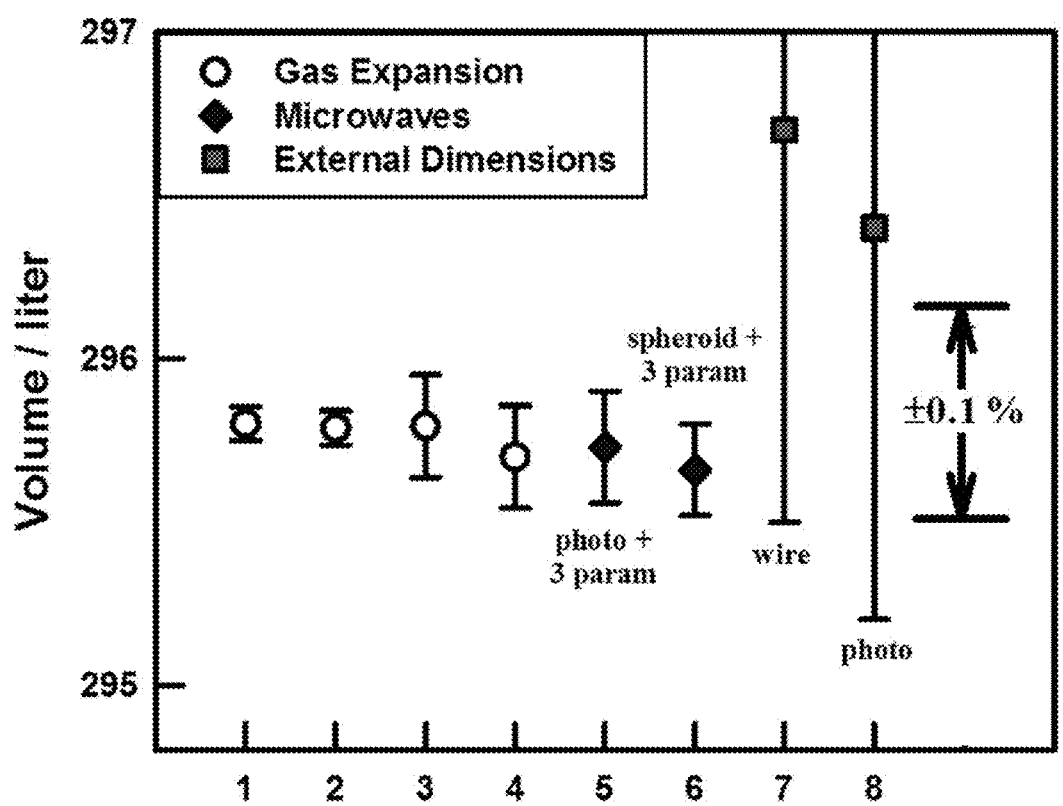
FIG. 4 shows a graph of volume versus measurement number according to Example 1.

In an embodiment, with reference to FIG. 3, acoustic receiver 108 includes electret condenser microphone 180, PTFE insulator disk 182, male-threaded end 150 of a pipe fitting NPT reducer 154, pipe fitting reducer 153 soldered to welding lip 175 of hermetic SMA feedthrough 152 that had floating shield 174, ceramic insulator 176, and coaxial contact 177. Microphone 180 had low signal lead 186 and high signal lead 188 passed through a hole through the back of PTFE disk 182 and soldered to feed-through contacts 172 and 174. Holes through PTFE disk 182 equalized an outside pressure with gas volume 184 behind microphone 180. Acoustic receiver 108 also can include male NPT thread 166.

Acoustic receiver 108 can be the same as or different from acoustic transmitter 106. With regard to a mutual arrangement or disposition of acoustic transmitter 106 and acoustic receiver 108 on vessel 128, they can be well separated, for example on opposite ends of vessel 128. By locating acoustic transmitter 106 and acoustic receiver 108 on distant portions of vessel 128, it is less likely that acoustic energy will pass directly from transmitter 106 to receiver 108 without passing through vessel 128. However, acoustic transmitter 106 or acoustic receiver 108 do not have to be disposed in a specific place on vessel 128.

In an embodiment, acoustic driver 114 is in electrical communication with acoustic transmitter 106 and provides acoustic control signal 132 to acoustic transmitter 106. Acoustic driver 114 produces a voltage or current waveform as acoustic control signal 132 to control production of acoustic radiation 124 by acoustic transmitter 106. Acoustic control signal 132 can have a selected frequency or amplitude to control the frequency or amplitude of acoustic radiation 124 from acoustic transmitter 106. Acoustic control signal 132 can provide modulation for acoustic radiation 124 such as amplitude modulation, frequency modulation, and the like having a selected period and duty cycle. Further, acoustic driver 114 can be in electrical communication with controller 120 to provide controller 120 with information (e.g., frequency, power, and the like) about acoustic radiation 124 produced by acoustic transmitter 106.

Vessel 128 receives microwave transmitter 102, microwave receiver 104, acoustic transmitter 106, acoustic receiver 108, pressure meter 110, temperature probe 126, and the gas. In this regard, vessel 128 can include a gas line connected to it for communication of the gas to interior 130. A valve can be disposed on vessel 128 to isolate or throttle communication of the gas to interior 130 of vessel 128. A vacuum pump can be in fluid communication with interior 130 of vessel 128 to evacuate or reduce a pressure of vessel 128.

Vessel 128 has a shape or size to receive the aforementioned components (e.g., microwave transmitter 102 acoustic transmitter 106, and the like), the gas, and the like as well as provide such components operability to determine volume V of vessel 128, mass M of the gas, a leak rate of vessel 128, or a combination thereof. Vessel 128 can be a commercially available vessel or a customized vessel. Vessel 128 can have a symmetrical shape, e.g. spherically symmetric, cylindrically symmetric, and the like. In some embodiments, vessel 128 has an irregular or asymmetrical shape.

Vessel 128 can be made of any material that allows for such components to perform determination of volume V of vessel 128, mass M of the gas, a leak rate of vessel 128, or a combination thereof. Exemplary materials for determining the mass M include metallic conductors such as aluminum, aluminum alloys, steels, copper, titanium, and other metals. For detection of a leak rate of vessel 128, the vessel can be made of any material that will contain the gas of interest. Exemplary materials for detection of leak rate include glass, fused silica, carbon fiber laminates, and good and poor conducting metals.

Here, it is contemplated that vessel 128 contains the gas in a cavity that allows the transmission and detection of microwave radiation 122 and also the transmission and detection of acoustic radiation 124 for determining the mass M of the gas in the cavity. For determining the mass M, the cavity should not contain electrically-conducting internal parts such as baffles, columns, pipes, struts, or electrically conducting level detectors or other electrical instruments except if such conducting parts are located in contact with one of the walls of the cavity and occupy only a small fraction of the volume of the cavity and do not obstruct the passage of microwaves 122. For detection of a leak rate of vessel 128, it is necessary that the internal parts of the vessel should not interfere with the transmission of acoustic radiation 124 from the acoustic transmitter 106 to the acoustic detector 108. Because acoustic radiation 124 passes around electrically conducting parts and electrically non-conducting parts such as baffles, columns, pipes, struts, or electrically conducting instruments, such internal structures are acceptable for detection of the leak rate of the vessel 128.

The gas disposed in vessel 128 is subjected to acoustic radiation 124 from acoustic transmitter 106. In response to receipt of acoustic radiation 124, the gas is subjected to a pressure wave that is transmitted through the gas and is received by acoustic receiver 108. It is contemplated that the gas has an acoustic resonance that can be excited by acoustic radiation 124, wherein and amplitude of acoustic radiation 124 resonant with the acoustic resonance of the gas decreases due to expectation of the acoustic resonance of the gas. In this manner, acoustic radiation 124 received by acoustic receiver 108 has an amplitude that varies depending on a species of the gas (e.g., nitrogen, methane, water, oxygen, a hydrocarbon, and the like, or a combination thereof) and frequency of acoustic radiation 124. The properties of diverse gases will not prevent the determination of the mass of the gas or leak rate.

Acousto-microwave system 100 can determine mass M of the gas disposed in vessel 128 by determining the volume of the vessel from the frequencies of microwave resonances, as corrected for the dielectric constant of the gas, and by determining the density of the gas from the measurements of the pressure and frequencies of the acoustic resonances. If the molar density of the gas is much less than 40 moles per cubic meter, acoustic radiation 124 in the vessel 128 will be attenuated within the gas and at the boundaries between the gas and the vessel. Therefore, accurate determinations of the mass require gas densities larger than approximately 4 moles per cubic meter, which occurs at pressures near $\frac{1}{10}^{th}$ of an atmosphere near 25° C. for gases such as methane and air. For such gases, accurate mass determinations cannot be made at pressures below $\frac{1}{10}^{th}$ of an atmosphere. If the product of the mass density of the gas and the square of the speed of sound in the gas is a significant fraction of the product of the mass density of the vessel's walls and the square of the speed of sound in the vessel's walls, the mass density cannot be determined accurately because the vessel's walls will vibrate excessively when they are subjected to acoustic radiation in the gas. For example, methane gas at 25° C. and a pressure of 100 MPa (equivalent to approximately 1000 atmospheres) has the product $3 \times 10^{11}$ gm·m$^{-1}$·s$^{-2}$ and steel has the product $3 \times 10^{14}$ gm·m$^{-1}$·s$^{-2}$; therefore, accurate determinations of the mass M cannot be made for methane at pressures above 100 MPa.

A mass spectrometer can be disposed on or in fluid communication with interior 130 of vessel 128. The mass spectrometer provides speciation of the gas disposed in vessel 128. In this manner, acousto-microwave system 100 determines a species of the gas (e.g., in a combination of gases) and mass M of the gas. Accordingly, if the gas is a single component gas or a combination of molecular or atomic species, mass M will provide a total mass of the gas in vessel 128.

Pressure meter 110 is disposed on vessel 128 and is in fluid communication with interior 130 to provide pressure p of the gas disposed in vessel 128. Pressure meter 110 can be selected depending on the type gas (e.g., corrosive, oxidative, noble, and the like) or a pressure regime (high pressure, low pressure, vacuum, and the like). Exemplary pressure meters 110 include a capacitance manometer, bourdon tube gauge, oscillating silicon crystal gauge, and the like. The accuracy of the determination of the mass M of the gas in the vessel 128 may not be, fractionally, more accurate than the accuracy of the pressure measurement. Pressure p of interior 130 of vessel 128 can be less than 100 MPa or greater than 10 kPa. Acousto-microwave system 100 can detect a presence of a leak of vessel 128. The smallest detectable leak in one day can be less than ten parts per million of the mass of gas in the vessel.

Temperature probe 126 is disposed on vessel 128 and is in thermal communication with vessel 128 to provide a temperature of vessel 128 that is in contact with the gas disposed therein. Temperature probe 126 can be selected depending on the type gas (e.g., corrosive, oxidative, noble, and the like) or a temperature regime (high temperature, low temperature, and the like). Exemplary temperature probes 126 include a thermocouple, resistance TD, and the like. The temperature of vessel 128 and interior 130 do not have to be the same or substantially identical. The temperature probe is a convenience to monitor the operation of the acousto-microwave system and to make certain corrections to the measurements; however, the temperature probe does not need to be very accurate. For example, the determination of the mass M in the pressure vessel can be accomplished with a temperature probe with an uncertainty of one degree Celsius.

Controller 120 is provided to receive data from various other components of acousto-microwave system 100. The data can include microwave data 134 from microwave receiver 104, acoustic data 136 from acoustic receiver 108, pressure data 138 from pressure meter 110, microwave input data from microwave source 112, acoustic input data from acoustic driver 114, temperature data 140 from temperature probe 126, and the like. Microwave data 134 can include the frequencies and widths of several microwave resonances. It is desirable that the microwave resonance frequencies be measured with an uncertainty of one part in one hundred thousand. Acoustic data 136 can include the frequencies and widths of several acoustic resonances. It is desirable that the acoustic resonance frequencies be measured with an uncertainty of one part in ten thousand or less. Pressure data 138 can include pressure measurements made every minute. It is desirable the pressure measurements be made with an uncertainty of one tenth of one percent or less.

In an embodiment, controller 120 includes a computer system for determining a property of acousto-microwave system 100 and optionally includes: a memory; and a processor, in communications with the memory, wherein the computer system is configured to determine the property of the acousto-microwave system 100. The property can be mass M of gas disposed in vessel 128, volume V of vessel 128, a leak of gas from vessel 128, or a combination thereof.

According to an embodiment, a computer program product for determining the property of acousto-microwave system 100 includes: a non-transitory computer readable storage medium readable by a processor and storing program code for execution by the processor to perform a process for determining mass M of gas disposed in vessel 128, volume V of vessel 128, a leak of gas from vessel 128, or a combination thereof.

Acousto-microwave system 100 has numerous beneficial and unexpected uses including determining mass M of the gas disposed in vessel 128. In an embodiment, a process for determining mass M of the gas disposed in vessel 128 includes: subjecting interior 130 of vessel 128 with microwave radiation 122 transmitted by microwave transmitter 102 disposed on vessel 128, a portion of microwave radiation 122 occurring at a microwave resonance of vessel 128; communicating microwave radiation 122 through interior 130 of vessel 128; receiving, by microwave receiver 104 disposed on vessel 128, microwave radiation 122 communicated through interior 130 of vessel 128; transmitting, by acoustic transmitter 108 disposed on vessel 128, acoustic radiation 124; subjecting the gas disposed in vessel 128 with acoustic radiation 124 transmitted by acoustic transmitter 106, a portion of acoustic radiation 124 occurring at an acoustic resonance of the gas in vessel 128; and communicating acoustic radiation 124 through the gas disposed in vessel 128; receiving, by acoustic receiver 108 disposed on vessel 128, acoustic radiation 124 communicated through the gas disposed in vessel 128; and analyzing microwave radiation 122 received by microwave receiver 104 and acoustic radiation 124 received by acoustic receiver 108 to determine mass M of the gas disposed in vessel 128.

The process also can include determining a pressure of the gas disposed in vessel 128, wherein determining the pressure of the gas disposed in vessel 128 includes acquiring a pressure signal 138 from pressure meter 110 disposed on vessel 128.

Analyzing microwave radiation 122 can include: determining a microwave frequency of a microwave resonance $f_m$ of vessel 128 based on microwave radiation 122 received by microwave receiver 104; determining an acoustic frequency of an acoustic resonance $f_a$ of the gas based on acoustic radiation 124 received by acoustic receiver 108; and combining the pressure of the gas, microwave frequency of the microwave resonance $f_m$ of vessel 128, and acoustic frequency of the acoustic resonance $f_a$ of the gas to determine mass M of the gas disposed in vessel 128.

The process can include determining volume V of vessel 128 from microwave frequency of the microwave resonance $f_m$ of vessel 128, wherein determining volume V of vessel 128 includes: providing a model shape of vessel 128; providing a plurality of model geometric parameters (e.g., the internal radius and volume of a spherical container and the expansion of that radius and volume with increasing temperature and internal pressure and the like) of vessel 128; computing a model microwave resonance of vessel 128 based on the model shape and the model geometric parameters; fitting microwave frequency of the microwave resonance $f_m$ and the model microwave resonance; adjusting the model geometric parameters to obtain a best fit of microwave frequency of the microwave resonance $f_m$ and the model microwave resonance; and determining volume V of vessel 128 from the geometric parameters used to obtain the best fit. If the vessel 128 is a cylindrical vessel with heads, the process can determine the radius of the cylinder, the length of the cylinder and the depth of the cylinder's heads.

The process can include determining an average temperature of the gas in vessel 128 from acoustic frequency of the acoustic resonance $f_a$ of the gas in vessel 128, wherein determining the average temperature of the gas includes determining a speed of sound in the gas from acoustic frequency of the acoustic resonance $f_a$ of the gas in vessel 128.

The process can include determining a density of the gas in vessel 128 from an equation of state of the gas, wherein mass M of the gas is determined according to formula (1), which is repeated here:

$$M = \rho(p, u)V \approx \frac{\gamma_0 pV}{u^2}\left[1 + (\beta_a - B)\frac{p}{RT}\right], \quad (1)$$

wherein M is the mass of the gas; $\rho$ is the density of the gas; $\gamma_0$ is a zero-pressure heat-capacity ratio that is equal to $C_p/C_v$, wherein $C_p$ is a constant pressure heat capacity of the gas, and $C_v$ is the constant volume heat capacity of the gas; p is the pressure of the gas; V is the volume of the vessel;

u is the speed of sound in the gas; $\beta_\alpha$ is an acoustic virial coefficient; B is a density virial coefficient; R is an ideal gas constant; and T is an average temperature of the gas in the vessel. The approximation on the right-hand-side of formula (1) is valid at low pressure such that the second term in the square brackets is small compared to unity.

According to an embodiment, a process for detecting a leak of the gas disposed in vessel 128 includes: determining pressure p of the gas disposed in vessel 128; transmitting, by acoustic transmitter 106 disposed on vessel 128, acoustic radiation 124 inside vessel 128; subjecting the gas in vessel 128 to acoustic radiation 124; receiving, by acoustic receiver 108 disposed on vessel 128, acoustic radiation 124 communicated through the gas from acoustic transmitter 106; determining acoustic frequency of an acoustic resonance $f_a$ of the gas based on acoustic radiation 124 received by acoustic receiver 108; and combining the pressure of the gas and acoustic frequency of the acoustic resonance $f_a$ of the gas to detect the leak of the gas disposed in vessel 128 according to a decrease in $p/(f_a)^2$. The process further can include: subjecting interior 130 of vessel 128 with microwave radiation 122 transmitted by microwave transmitter 102 disposed on vessel 128, a portion of microwave radiation 122 occurring at a microwave resonance of vessel 128; communicating microwave radiation 122 through interior 130 of vessel 128; receiving, by microwave receiver 104 disposed on vessel 128, microwave radiation 122 communicated through interior 130 of vessel 128; determining microwave frequency of a microwave resonance $f_m$ of vessel 128 based on microwave radiation 122 received by microwave receiver 104; and determining volume V of vessel 128 from microwave frequency of the microwave resonance $f_m$ of vessel 128.

In the process for detecting the leak of the gas, determining the volume of the vessel can include: providing a model shape of vessel 128; providing a plurality of model geometric parameters of vessel 128; computing a model microwave frequency of the microwave resonance of vessel 128 based on the model shape and the model geometric parameters; fitting the microwave frequency of the microwave resonance $f_m$ and the model microwave frequency; adjusting the model geometric parameters to obtain a best fit of microwave frequency of the microwave resonance $f_m$ and the model microwave frequency; and determining volume V of vessel 128 from the geometric parameters used to obtain the best fit.

The process for detecting the leak of the gas can include: determining an average temperature of the gas in vessel 128 from acoustic frequency of the acoustic resonance $f_a$ of the gas in vessel 128; and determining mass M of the gas in vessel 128 according to formula (1) repeated here:

$$M = \rho(p, u)V \approx \frac{\gamma_0 p V}{u^2}\left[1 + (\beta_\alpha - B)\frac{p}{RT}\right], \quad (1)$$

wherein M is the mass of the gas; $\rho$ is the density of the gas; $\gamma_0$ is the zero-pressure heat-capacity ratio that is equal to $C_p/C_v$, wherein $C_p$ is the constant pressure heat capacity of the gas, and $C_v$ is the constant volume heat capacity of the gas; p is the pressure of the gas; V is the volume of the vessel; u is the speed of sound in the gas; $\beta_\alpha$ is the acoustic virial coefficient; B is the density virial coefficient; R is the ideal gas constant; and T is the average temperature of the gas in the vessel. The approximation on the right-hand-side of formula (1) is valid at low pressure such that the second term in the square brackets is small compared to unity.

Acousto-microwave system 100 has numerous beneficial uses, including determining the mass of gas in a collection vessel that is used as part of a system to calibrate meters that measure gas flow. The high accuracy of the mass determination and the insensitivity of the mass determination to temperature gradients in the gas are particularly advantageous in this application. Another use is the determination of mass in very large tanks for custody transfer of valuable gases. Another use is rapidly detecting leaks in air locks such as the air locks used to gain controlled access to the containment systems for nuclear power plants. The ability of the acousto-microwave system to rapidly detect leaks, even in the presence of temperature changes is particularly advantageous in this application because rapid leak detection shortens the down-time required to maintain and verify the safe operation of nuclear power plants.

Beneficially, acousto-microwave system 100 The acousto-microwave system can be used to test complex vessels for leaks. For example, the system might be used to detect leaks from airplane fuselages or between a ship's water-tight compartments during the construction and maintenance of such complex vessels.

The articles and processes herein are illustrated further by the following Examples, which are non-limiting.

Examples

Example 1

Determination of Volume of a Vessel

Here, microwave techniques were used that were scalable to very large volumes. We measured an interior volume of a 0.3 m$^3$, commercially manufactured vessel with a relative uncertainty of 0.06%. It was contemplated that the vessel (or a much larger one of a similar design) could be used as a calibrated volume standard, gas source, or gas collector for calibration of gas-flow meters. In addition, we determined the expansion of the vessel with temperature $(\partial V/\partial T)_p/V = (35.3 \pm 1.9) \times 10^{-6}$ K$^{-1}$, and we estimated the pressure expansion $(\partial V/\partial p)_T/V = 0.9 \times 10^{-3}$ MPa$^{-1}$. The volume measurement did not include careful thermostatting. Estimated uncertainties were one standard uncertainty with coverage factor k=1 corresponding to 68% confidence level.

Here, we showed accurate determination of volume and density of gas within a large, off-the-shelf, commercially manufactured, un-thermostatted vessel. To measure the vessel volume with microwaves we: 1) proposed a shape and defining geometric parameters (e.g., length of the central cylinder L and end cap ellipsoid dimensions a and b), 2) used a finite element simulation to compute the spectrum of resonant microwave frequencies, 3) fit the measured and computed resonances by adjusting the geometric parameters, and 4) calculated the volume from the geometric parameters.

Figure 5:
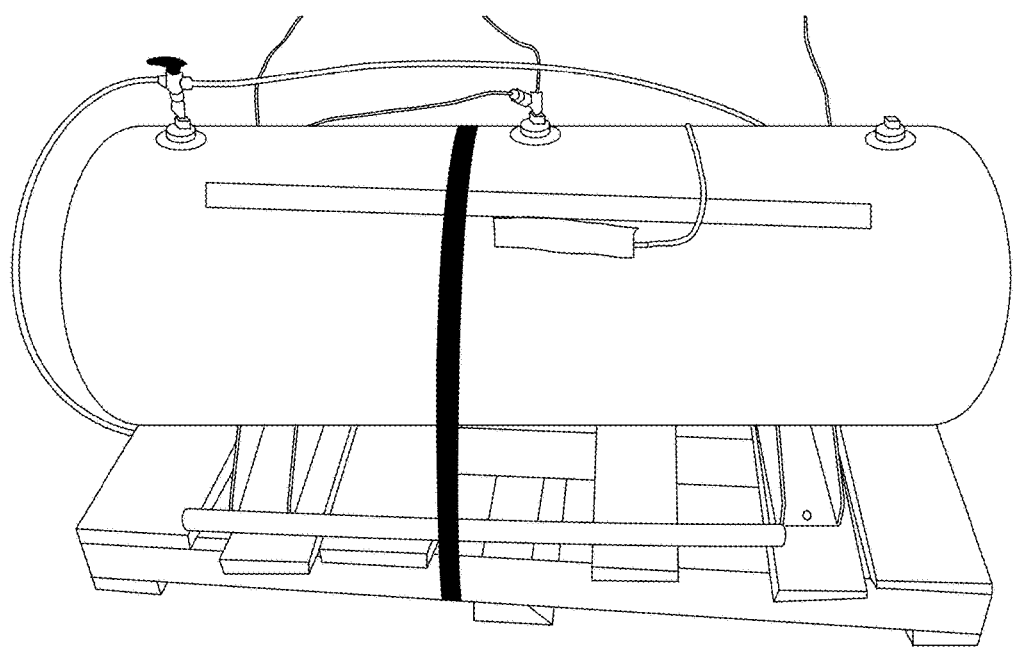
FIG. 5 shows a photograph of a vessel according to Example 1.

Microwave and acoustic resonance frequencies were used to determine a volume of a commercially available, inexpensive vessel that had a poorly known shape. A photograph of the vessel as shown in FIG. 5. Because of the complicated shape of the present volume, we determined at least 3 lengths to determine its volume geometrically with the relative uncertainty $u_r(V)=0.0005$. The vessel was made of ferromagnetic steel.

Other applications of our technology using microwave resonances include fluid metrology. Our techniques can be used to measure of a quantity of hydrogen fuel (liquid or gaseous) in vehicle fuel vessels or in storage vessels at refueling stations, determine a quantity of liquid oxygen in a dewar, monitor cryogenic propellant transfers in low gravity, and more.

The vessel was a 0.3 m³, horizontal vessel commercially manufactured for use as an air receiver with a maximum operating pressure of 1.38 MPa (Silvan Industries, Inc., Marinette, Wis., USA, Part Number A10031). The manufacturer stated that it was designed and built to comply with ASME Code, Section VIII, Div. 1, 20$^{th}$ Edition. For this research, the vessel was not modified in any way except by the addition of sensors inserted into the ports that were built into the vessel. As shown in FIG. 5, the vessel was a horizontal, approximately circular cylinder with hemispheroidal "end caps" (called "heads") welded to each end of the cylinder. According to the manufacturer, these parts were made of hot-rolled carbon steel SA414-G. (For this steel, the ASTM specifies the maximum mole percentages: C, 0.31; Mn, 1.35; P, 0.035; S, 1.04.) The manufacturer's drawings indicate that the cylindrical section has a length of 1.3 m, an outside diameter of 0.51 m, and a wall thickness of 3.9 mm. The cylindrical section had been manufactured from a plate, and it had a weld bead along its entire length on both its outside and inside surfaces. The end caps were "2:1 semi-elliptical heads." Their shapes were approximately oblate hemispheroids (that is, half of an ellipse of revolution) with an outside semiminor axis of 0.12 m and a 3.2 mm wall thickness. The end caps had a joggle (a short cylindrical extension that fits inside the cylindrical section) to facilitate welding. We estimated that the joggles plus the weld beads inside the vessel occupied approximately 130 cm³≈0.00043 $V_{vessel}$ in the vessel interior.

The vessel's walls were penetrated by 7 ports. At each port, the manufacturer had welded a threaded fitting to the outside of the vessel. We used these ports to install acoustic transducers and microwave antennas, and we capped the unused ports with threaded brass plugs that were sealed with fluorocarbon tape. Each of the two largest ports was on the axis of an end cap and, when plugged, each had an internal volume of approximately 30 cm³. These ports were capped during the gas-expansion measurements, and their volumes were included in the total volume of the vessel. During the microwave measurements, one of these ports was connected to a gas-supply manifold. The internal volumes of the 5 smaller ports totaled 29 cm³. This total was included in the gas-expansion measurements but not in the models used to interpret the microwave measurements. Therefore, we included 29 cm³ in the uncertainty budget for the microwave measurements. During the gas expansion measurements, a pressure line (5 cm³) connected one port to a pressure sensor; however, we accounted for its volume with negligible uncertainty.

Estimated Volume from External Dimensions.

To measure the outside circumference of the vessel, we stretched a wire around the vessel and then measured its length. We used the measured circumference to calculate the outside diameter D=(0.5083±0.0010) m. We used a digital camera to photograph one of the vessel's end caps. We digitized the coordinates of 127 points on the photograph that traced the outside of the end cap. The photograph included a ruled steel scale that enabled us to correct the coordinates for the camera's magnification and parallax in both the horizontal and vertical directions. The corrected coordinates defined the profile of the outer surface of the end cap and yielded an outside diameter of D=(0.5080±0.0010) m. Using a steel scale, we measured the average distance between the centers of the weld beads and assumed that the result L=(1.3250±0.0010) m was the length of the cylindrical section of the vessel. We combined these dimensional measurements of the length, diameter, and profile with the thicknesses provided by the manufacturer to make two estimates of the vessel's volume: (1) $V_{vessel,dimension}$= (296.7±1.2) L using D from the wire measurement, and (2) $V_{vessel,dimension}$=(296.4±1.2) L using D from the photograph. These results are listed in rows 7 and 8 of Table 1. Within combined uncertainties, $V_{vessel,dimension}$ is consistent with the gas-expansion and microwave measurements discussed below; however, their relative uncertainty $u_r(V_{vessel,dimension})$=0.0041 is 20 times larger than the uncertainty of gas-expansion measurements.

Gas Expansion Measurements.

We determined the volume of the vessel $V_{vessel}$ at ambient temperature using a gas-expansion technique that requires a well-thermostatted, accurately known standard volume $V_{std}$. Initially, the vessel was filled with pure nitrogen at the measured pressure $p_{vessel,i}$ and at the temperature $T_{vessel,i}$ while the standard volume was evacuated to the low measured pressure $p_{std,i}$ at the temperature $T_{std,i}$. Then, a valve in a tube connecting the standard volume to the vessel was opened and both volumes were allowed to equilibrate. Finally, the pressure $p_f$ and temperatures $T_{std,f}$ and $T_{vessel,f}$ was measured. Conservation of the nitrogen's mass leads to the approximate relationship between $V_{vessel}$ and $V_{std}$ $$M_{N2} \approx \rho_{std,i} V_{std,i} + \rho_{tank,i} V_{tank,i} \approx \rho_{std,f} V_{std,f} + \rho_{tank,f} V_{tank,f} \qquad (2),$$

wherein the four densities were calculated from the corresponding temperature and pressure measurements using the virial equation of state for nitrogen $$p = \rho RT(1 + B\rho + \ldots). \qquad (3).$$

Here, R is the universal gas constant and B is the second density virial coefficient. We applied small corrections to Eqs. 1 and 2 to account for the gas in the tubing connecting the pressure gauges to $V_{vessel}$ and $V_{std}$, and for the volumes within the gauges.

For $V_{std}$, we used the collection volume of NIST's flow standard, $V_{std}$=(677.936±0.028) L when the pressure in the volume standard was either 50 kPa or 100 kPa and the temperature was 296.655 K. During the present measurements, the water bath that thermostats $V_{std}$ was always within ±0.004 K of 296.655 K.

The dominant contributor to the uncertainty of the gas-expansion method (up to 82%) is the resolution of the pressure sensor on $V_{vessel}$ (10 Pa). To estimate this contribution, it is useful to ignore the connecting volume and make the approximations $T_{vessel,i}=T_{vessel,f}=T_{std,i}=T_{std,f}$, and B=0. With these approximations, $$V_{tank} \approx (V_{std} p_f)/(p_i - p_f). \qquad (4)$$

In Eq. 4, the scale factor for the pressure transducer (which may be in error) cancels out of the ratio $p_f/(p_i-p_f)$, and we corrected the measurements for the small zero drift. For the full uncertainty analysis, we did not make simplifying assumptions. The uncertainty of $V_{vessel}$ includes contributions from the pressure uncertainty in the standard volume (<2 Pa from sensor non-linearity) and the uncertainty of the temperature change in the test vessel (0.017 K).

While conducting the gas expansion measurements, $(T_{vessel}-T_{std})<1$ K. Although errors in the laboratory temperature measurements largely cancel out of the ratio $V_{vessel}/V_{std}$, the ratio is sensitive to errors in the measurements of small temperature differences. We used six thermometers. Two monitored the temperature of the water bath surrounding $V_{std}$; they were mutually consistent within ±0.001 K. The remaining four thermometers monitored the temperatures at different locations on the vessel; when they were tested in the water bath, they were mutually consistent within ±0.003 K. One hour after the expansion, the temperatures indicated by these thermometers spanned, in the worst case, 0.060 K and had a standard deviation from their mean of 0.017 K. We used this standard deviation as an estimated uncertainty of the mean temperature of the gas inside the vessel. Thus, temperature measurements contributed approximately $(0.017 \text{ K})/(297 \text{ K})=6\times10^{-5}$ to the relative uncertainty $u_r(V_{vessel}/V_{std})$. For completeness, we note that the pressure changes during the expansions cause $V_{vessel}$ to decrease and $V_{std}$ to increase. However, these pressure-dependent volume changes are much smaller than other uncertainties of the expansion measurements. We estimate $(\partial V/\partial p)_T/V = 0.9 \times 10^{-3}$ MPa$^{-1}$.

Two gas expansions were conducted from 100 kPa to 30 kPa and two were conducted from 30 kPa to 10 kPa. The results $V_{vessel,i}$ and their estimated uncertainties $u(V_{vessel,i})$ are listed in rows 1 to 4 in Table 1. The mean of these four measurements is $V_{vessel} = 295.790$ L, weighted by $1/u(V_{vessel,i})^2$. A weighted mean is the best estimate of the volume because the uncertainties of the measurements for the two pressure ranges are very different. In addition, because the uncertainties of the four measurements are highly correlated, we did not account for multiple measurements in the estimate of the uncertainty of the weighted mean. Instead, we conservatively assumed that the uncertainty of the weighted mean was 0.052 L, the lowest uncertainty of the individual measurements.

TABLE 1

| Row | Method | Volume/liter |
|---|---|---|
| | Gas expansion | |
| 1 | 100 kPa to 30 kPa | 295.801 ± 0.052 |
| 2 | 100 kPa to 30 kPa | 295.788 ± 0.052 |
| 3 | 30 kPa to 10 kPa | 295.794 ± 0.157 |
| 4 | 30 kPa to 10 kPa | 295.699 ± 0.157 |
| | Microwaves | |
| 5 | photo + 3 param[a] | 295.73 ± 0.17 |
| 6 | spheroid; 3-param[a] | 295.66 ± 0.14 |
| | Dimensions | |
| 7 | diameter from wire | 296.7 ± 1.2 |
| 8 | diameter from photo | 296.4 ± 1.2 |

To summarize, the gas expansion measurements gave the result:

[a]The addition of two more parameters reduced the volumes by 0.03 L.

$$V_{tank,gas}(295.790 \pm 0.052)L \quad (5)$$

In Eq. 5, we added the subscript "gas" to emphasize that the gas-expansion measurement determined the total volume of the vessel that was accessible to the nitrogen gas. Therefore, $V_{vessel,gas}$ includes small volumes that were not included in the models used to interpret the microwave and acoustic measurements. As mentioned above, the internal volumes of the 5 smaller ports increased $V_{vessel,gas}$ by 29 cm$^3$ and the volume of the weld beads plus the joggles decreased $V_{vessel,gas}$ by approximately 130 cm$^3$.

Measuring Microwave Frequencies: Antennas for Microwave Transmitter and Receiver.

To measure microwave resonance frequencies, transmitting and receiving antennas were disposed in ports in the cylindrical section of the vessel. One antenna was disposed on the top of the vessel near its middle as shown in FIG. 5. The other antenna was disposed in a drain port near one end of the vessel (not visible in FIG. 5). Each port was sealed with a National Pipe Thread (NPT) threaded plug that had been drilled to accommodate a ceramic feed-through. A beryllium copper clamp was press-fit over the inner conductor of each feed-through. A straight copper wire was inserted in each clamp and held in place with a set screw. Each wire acted as an antenna coupling to the electric fields of the microwave modes.

We estimated the influence of the antennas on the measured frequencies $f_{meas}$ of the microwave resonances by using wires of three different lengths: $l_a \approx 85$ mm, ≈57 mm, and ≈35 mm. Because the seal on each port was approximately 16 mm outside the inner surface of the vessel these wires protruded a smaller distance ($l_a$−16 mm) into the cylindrical section of the vessel. Using the values of $f_{meas}$ obtained with the shortest wire ($l_a \approx 35$ mm) as a reference, we found the largest frequency shifts were $(f_{85\text{ }mm}-f_{35\text{ }mm})/f < 0.0013$ and $(f_{57\text{ }mm}-f_{35\text{ }mm})/f < 0.00014$ and the average frequency shifts were $<(f_{85\text{ }mm}-f_{35\text{ }mm})/f> = 0.0004$ and $<(f_{57\text{ }mm}-f_{35\text{ }mm})/f> = 0.00006$. These frequency shifts varied approximately as $(l_a-16 \text{ mm})^4$; therefore, we estimate the fractional frequency shifts for the 35 mm antenna were <0.00002, which is much less than other uncertainties. The amplitude of the resonances decreased as $(l_a-16 \text{ mm})^{5\pm1}$; therefore, shorter antennas could not be used. FE calculations predicted that the maximum fractional frequency perturbations are −0.00004, −0.00032, and −0.0014 for the 35 mm, 57 mm, and 85 mm antennas, respectively.

When we changed the antennas from $l_a=57$ mm to $l_a=35$ mm, the average value of the half-width $g_{exp}$ decreased by the factor 0.97 with standard deviation of 0.04.

Microwave Spectrum.

Figure 6:
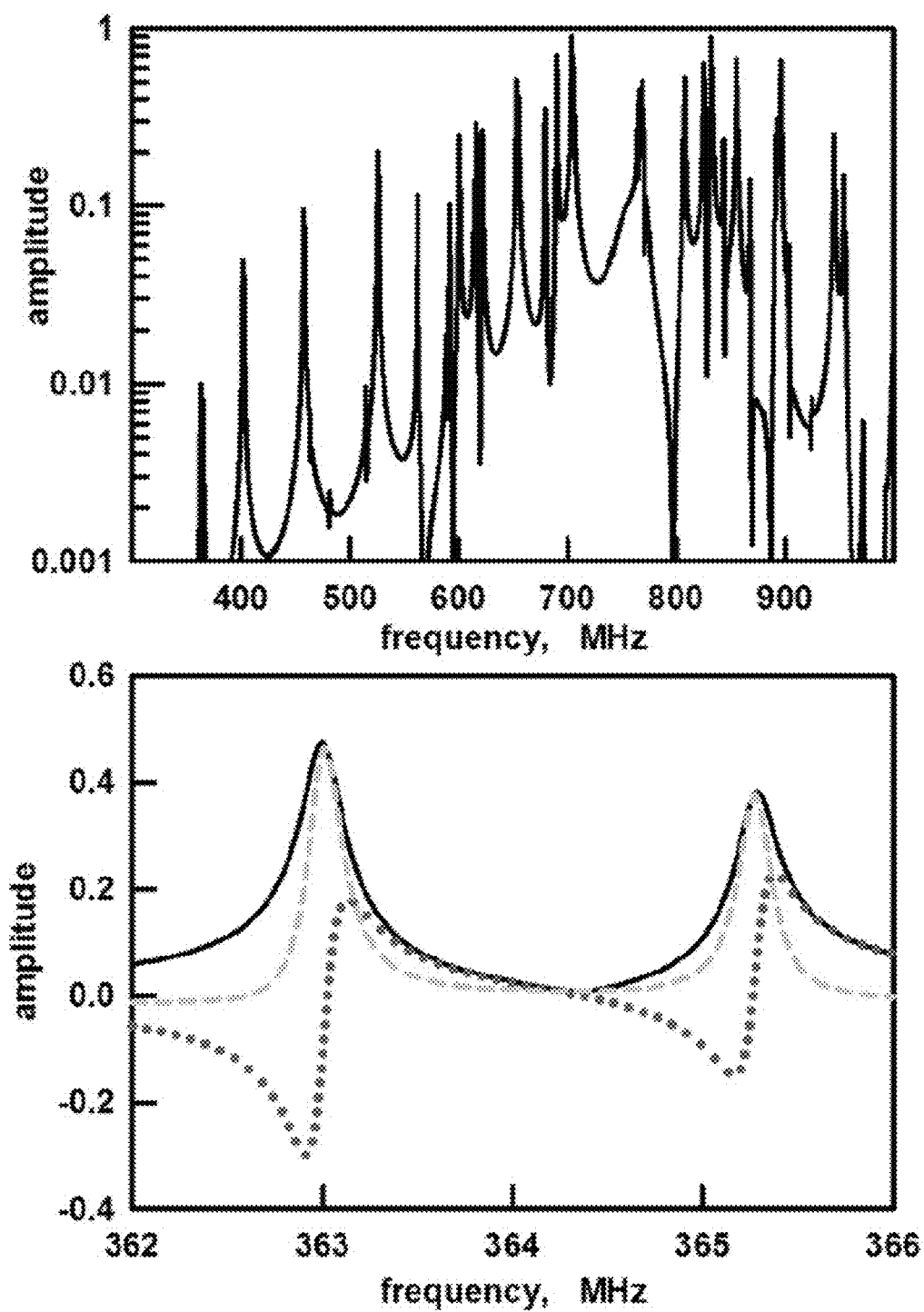
FIG. 6 shows a graph of an amplitude of a microwave signal versus frequency according to Example 1.

FIG. 6 displays the spectrum of the microwave resonances measured in the vessel shown in FIG. 5. This spectrum was measured while the vessel was filled with dry nitrogen at approximately 99 kPa and 22° C. Under these conditions, the square of the refractive index of the nitrogen was $n_g^2 = 1.00053$.

The lower-frequency resonances in the top panel of FIG. 6 was identified with the resonance modes of an ideal cylindrical cavity with flat ends. Here, we provide expressions for the frequencies and half-widths of such an ideal cavity with radius a and length L. These expressions guided our measurements and our interpretation of the results. We divided the resonance modes into two categories: transverse magnetic (TM) and transverse electric (TE), according to which field (magnetic or electric, respectively) had its axial component identically equal to zero. We imposed boundary conditions on the microwave fields assuming the walls of the vessel are perfectly conducting. For the TM mnl modes the resonance frequencies were:

$$(2\pi f_{mnl}^{TM})^2 = \frac{c^2}{n_g^2}\left(\frac{l^2\pi^2}{L^2} + \frac{\alpha_{mn}^2}{a^2}\right). \quad (6)$$

In Eq. 6, c is the speed of light in vacuum; $n_g$ is the refractive index of the gas in the cavity; $l \geq 0$ is an integer; $\alpha_{mn}$ is the nth root of $J_m(z)=0$; and $J_m$ is the Bessel function of the 1st kind of order m. Because the walls of a real cavity have a finite electrical conductivity $\sigma_s$ and a relative magnetic permeability $\mu_s$, the microwave fields within the walls decay exponentially with the decay length ("skin depth")

$$\delta_s = 1\sqrt{\pi\mu_0\mu_s\sigma_s f} \quad (7).$$

We use the subscript "s" to denote the properties of the carbon steel walls of the cavity. For the TM modes, the microwave fields within the skin depth reduce the resonance frequencies and increase the resonance half-widths by equal amounts g, where 2g is given by:

$$\frac{2g}{f} = \frac{1}{Q^{TM}} = \frac{\mu_s \delta_s}{a}\left[1 + (2-\delta_{l0})\frac{a}{L}\right], \quad (8)$$

wherein we have assumed the relative magnetic permeability of the gas $\mu_g = 1$. Here, the symbol $\delta_{l0}$ has the value 0 when $l \neq 0$ and the value 1 when $l = 0$. Equation 7 predicts $\delta_s = 1.2 \times 10^{-5}$ m when f=400 MHz, $\sigma_s = 4 \times 10^6$ S/m, and $\mu_s = 1$. The vacuum permeability $\mu_0 = 4\pi \times 10^{-7}$ N A$^{-2}$ is a fundamental constant. We show later that for all modes $g_{meas} \approx (8.00 \pm 0.23) \times g_{0s}$, where $g_{0s}$ was the value of g calculated from Eqs. 8 and 9 using $\sigma_s = 4 \times 10^6$ S/m and $\mu_s = 1$. The larger measured half-widths suggest that the ratio $\mu_s/\sigma_s$ is 64 times larger than the value we used to calculate $g_{s0}$. If we assume that the value we used for $\sigma_s$ is correct, then the measurements suggest that $\mu_s \approx 64$ and, therefore, $\delta_s = 1.5 \times 10^{-6}$ m at 400 MHz. A value of $\mu_s \gg 1$ at microwave frequencies is not surprising for the ferromagnetic steel used to construct the vessel.

Because the microwave fields extend into the vessel's walls a distance on the order of $\delta_s$, the microwave frequencies will overestimate the vessel's volume by a fraction of order $\delta_s A_{vessel}/V_{vessel} \approx 1.3 \times 10^{-5}$, where $A_{vessel}$ is the internal surface area of the vessel. We account for this overestimate by determining the dimensions of the vessel from the sum $(f_{meas} + g_{meas})$ instead of from $f_{meas}$. We estimate the uncertainty in the volume due to the skin depth as follows. The skin depth $\delta_s$ is proportional to g, so the relative uncertainty of the skin depth $u(\delta_s)/\delta_s = 0.23/8$ from the half-width measurements. Therefore, the relative uncertainty of the volume associated with the skin depth is $u(\delta_s)A_{vessel}/V_{vessel} = 4 \times 10^{-7}$, assuming $\sigma_s = 4 \times 10^6$ S/m and $\mu_s = 64$. However, we cannot rule out the possibility that the effective electrical conductivity is lower than the bulk value due to surface roughness. If we assume that $u(\sigma_s) = 0.5\sigma_s$ due to surface roughness and that the ratio $\mu_s/\sigma_s$ is correlated by the measured half-widths, then $u(\delta_s)A_{vessel}/V_{vessel}$ due to the uncertainty in the electrical conductivity is $1.3 \times 10^{-5}$ $u(\sigma_s)/\sigma_s = 6 \times 10^{-6}$, which appears in Table 3.

The resonance frequencies for the TEmnl modes of an ideal cylindrical cavity are $$(2\pi f_{mnl}^{TE})^2 = \frac{c^2}{n_g^2}\left(\frac{l^2\pi^2}{L^2} + \frac{\beta_{mn}^2}{a^2}\right). \quad (9)$$

In Eq. 9, $l \geq 1$ is an integer and $\beta_{mn}$ is the nth root of $dJ_m(z)/dz = 0$. For the TE modes, the skin depth reduces resonance frequencies and increases the resonance half-widths by equal amounts g, where 2g is given by:

$$\frac{2g}{f} = \frac{1}{Q^{TE}} = \frac{\mu_s \delta_s}{a} \frac{\left(\frac{\beta_{mn}}{a}\right)^2 + \frac{2a}{L}\left(\frac{\pi l}{L}\right)^2 + \left(1-\frac{2a}{L}\right)\left(\frac{\pi m l}{\beta_{mn}L}\right)^2}{\left[1-\left(\frac{m}{\beta_{mn}}\right)^2\right]\left[\left(\frac{\beta_{mn}}{a}\right)^2 + \left(\frac{\pi l}{L}\right)^2\right]}. \quad (10)$$

For an ideal cylindrical cavity, the TE and TM modes with m>0 can each have two independent orientations (about the cylinder axis) with exactly the same frequency; we say they are degenerate with multiplicity 2 or "doublets". Certain shape imperfections that spoil the axial symmetry may shift the frequency of one orientation with respect to the other. These nearly degenerate, overlapping resonance peaks may be unresolved if the imperfections are small, or they may be fully resolved if the frequency splitting is larger than the widths of the resonance peaks. Also, in an ideal cylindrical cavity, the TE011 modes are degenerate with the TM111 modes; thus, they would form a series of triplets (2 TM modes+1 TE mode). We did not measure the frequencies of these modes; we expect that shape imperfections would split the triplets into a singlet well separated from a doublet.

Shape Imperfections.

The lower panel of FIG. 6 displays an expanded view of the microwave spectrum near the TE111 mode as a function of frequency. We obtained the spectrum using a microwave vector analyzer, which measures values of $S_{12}$, the ratios of the in-phase u and quadrature voltages v at the detecting antenna to the same voltages at the driving antenna. FIG. 6 shows that the two-fold degenerate TE111 mode is split into two distinct resonance peaks, each with its own center frequency, denoted here as $f_{high}$ and $f_{low}$, and its own half-width, $g_{high}$ and $g_{low}$. The fractional separation between the TE111 components $(f_{high} - f_{low})/(f_{high} + f_{low}) = 0.0031$ was 10 times the scaled half-width of each component $(g_{high}/f_{high} \approx g_{low}/f_{low} = 0.00030)$; therefore, it was straight-forward to fit the vector analyzer data with a sum of two resonance formulas, $$u + iv = \sum_{i=high, low} \frac{ifA}{f^2 - (f_i + ig_i)^2} + B + C(f - \tilde{f}) + D(f - \tilde{f})^2. \quad (11)$$

In some cases, C and D were unnecessary. For numerical stability, $\tilde{f}$ is set to an arbitrary value within the range of the measurements. The fitted values of $f_{high}$, $f_{low}$, $g_{high}/f_{high}$ and $g_{low}/f_{low}$ had relative uncertainties $u_r(f) < 10^{-6}$ and $u_r(g/f) < 10^{-6}$. For the microwave determination of the volume $V_{micro}$, these uncertainties are insignificant compared with the uncertainty resulting from imperfect knowledge of the vessel's shape. Therefore, a satisfactory determination of $V_{micro}$ could be made using less-expensive instruments that determine the frequencies of the maximum amplitudes instead of fitting $S_{12}$ with Eq. 11.

Figure 7:
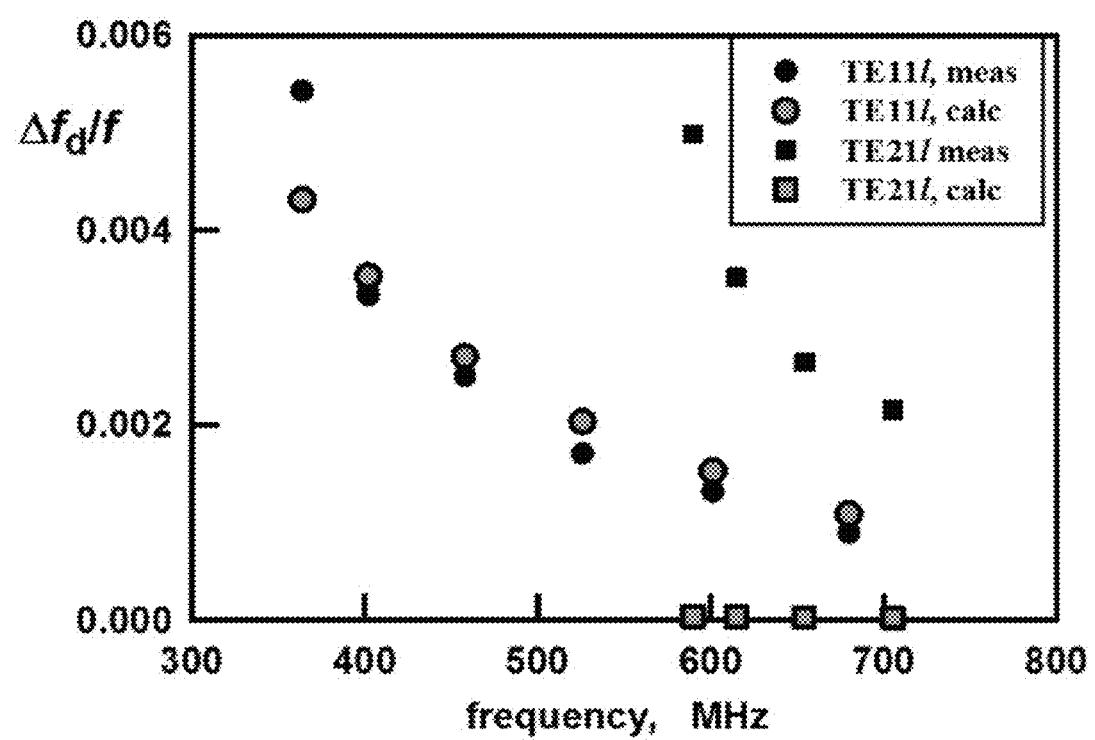
FIG. 7 shows a graph of measured and calculated frequency splittings of doublets versus frequency according to Example 1.
Figure 8:
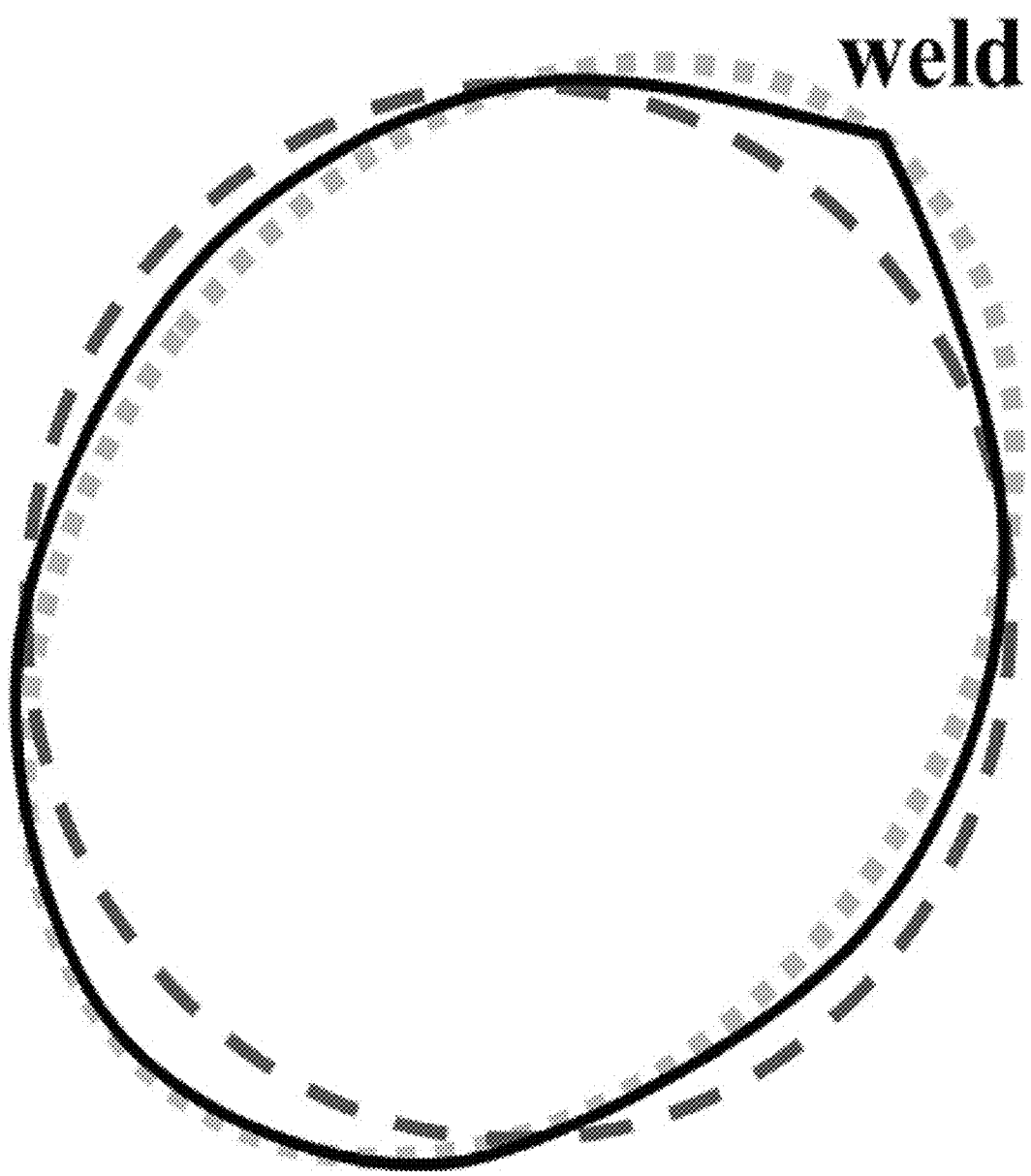
FIG. 8 shows possible deviations of a cross-section of a vessel according to Example 1.

The central, cylindrical section of the vessel in FIG. 5 had been formed by rolling a plate and welding its sides together; therefore, it is likely that the cross-section of the vessel will deviate from a circle. If the cross-section were elliptical with semimajor axis a(1+e) and semiminor axis a/(1+e), the cross-sectional area would be unchanged; however, the two-fold degenerate m=1 doublets would be split into two distinct components with a fractional separation $\Delta f_d/f \equiv (f_{high} - f_{low})/(f_{circle})$ on the order of e. FIG. 7 displays the measured and calculated splittings for the TE111 doublets for $1 \leq l \leq 6$ and the TE211 doublets for $1 \leq l \leq 4$. The calculations assumed an elliptical cross-section with $e = 2.6 \times 10^{-3}$. For the TE111 modes, $10^4[(\Delta f_d/f)_{meas} - (\Delta f_d/f)_{calc}] = 11, -2, -2, -3, -2,$ and $-2$ for $l = 1, 2, \ldots 6$, respectively. An elliptical cross-section does not split the TE211 doublets; however, these doublets had splittings as large as $2.7 \times 10^{-3}$. (FIG. 7) This discrepancy is evidence that the cross-section is more complicated than an ellipse. The ports on the top of the vessel are known, small complications that might split the TE211 doublets. Another plausible complication is a discontinuous slope at the weld, as represented by the solid black curve in FIG. 8.

Perturbation theory (see below) provided insight concerning the effects of smooth, general deviations from a circular cross-section. We considered a cylinder with radius a and a deviation function $\Delta a(\phi)$, where $\phi$ measured the angle about the cylinder's axis. If $\Delta a(\phi)$ has periodicity $\pi$, the deviation was described an ellipse, and it was used to fit the splittings of the TE111 doublets. If $\Delta a(\phi)$ had periodicity $\pi/2$, it was used to fit the splittings of the TE211 doublets. A simple alternative to finding the $\Delta a(\phi)$ that fitted all the measured doublets was to average the doublets. After averaging, any remaining effects of $\Delta a(\phi)$ was of order $e^2$. These effects could be calculated using second-order shape perturbation theory. Fortunately, for values of e~0.0026, the second-order perturbations were negligible compared with other errors.

We used the 16 lowest-frequency modes of the vessel to determine $V_{micro}$. Of these modes, 10 were nearly degenerate doublets and 6 were non-degenerate singlets spanning the range 363 MHz to 706 MHz. (See Table 2.) At higher frequencies, it became increasingly difficult to identify the measured frequencies with particular calculated frequencies because the density of modes increases as $f^2$. As the frequency increases, the widths of the modes increase as $f^{1/2}$; therefore, the chance of modes overlapping increases as $f^{5/2}$.

Determining the Shape from Microwave Frequencies.

We constructed two models for the shape of the cavity and calculated the resonance frequencies of each model using commercial, finite-element (FE) software. We chose the geometric parameters in each model to minimize $\Sigma[(f_{meas}+g_{meas}-f_{calc})/f]^2$ where the sum is over the 16 modes listed in Table 2. Here, $f_{calc}$ were the calculated frequencies of the microwave modes within a cavity with perfectly conducting walls (and, therefore, zero skin depth $\delta_s$). Then, we calculated the volume of each model cavity and estimated its uncertainty from the deviations between the measured and calculated frequencies and from other sources. The differences between the volumes of the two models were much smaller than the differences between either model and the data. This suggests that any additional uncertainty associated with the selection of a model was small.

Each model cavity had a central section that was a circular-cylindrical tube with length L and internal radius a. The models differed from each other by the shapes of the end caps as sketched in FIG. 8.

Model 1: Photograph-Based End Cap Shape.

Figure 9:
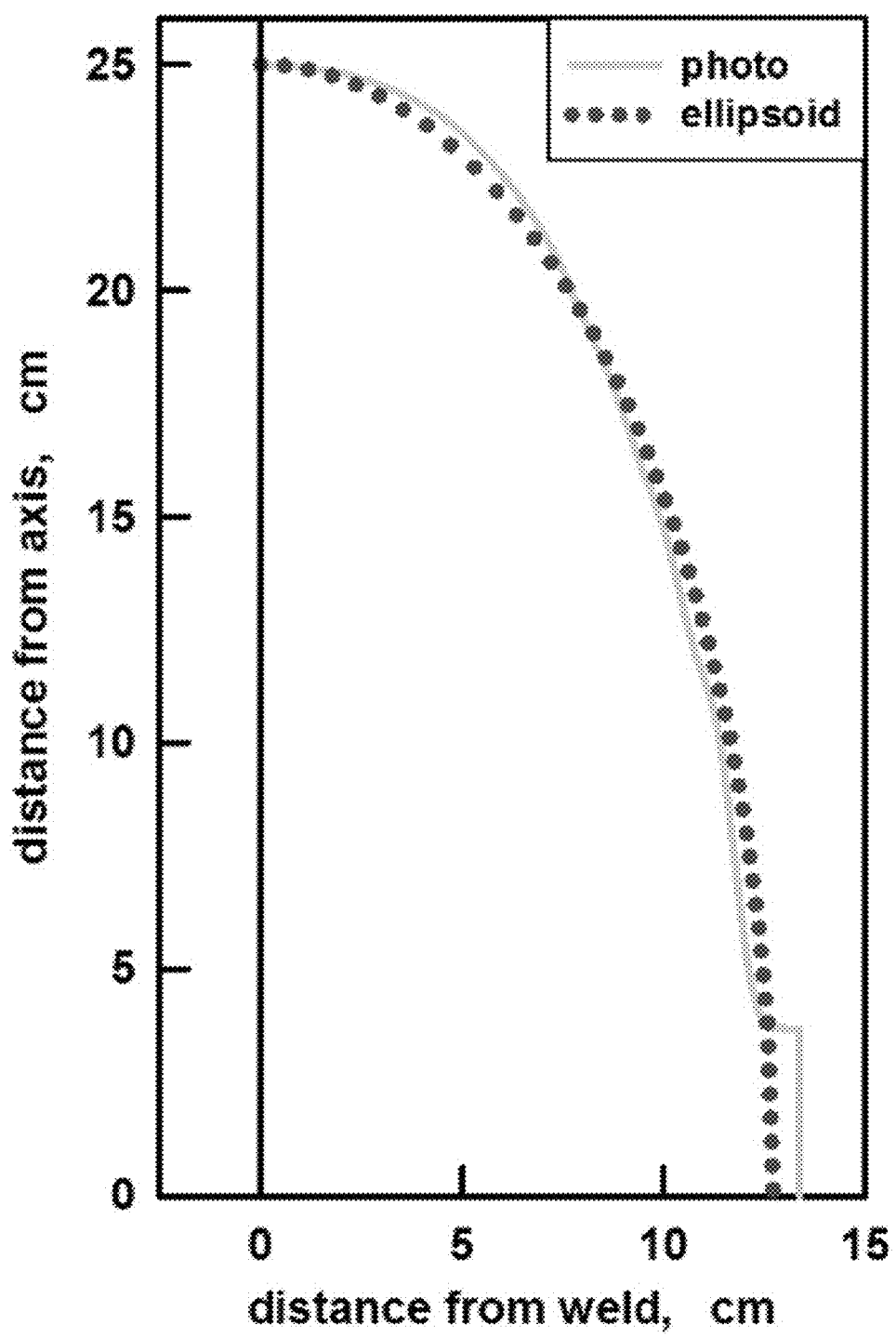
FIG. 9 shows shows a graph of distance from axis versus distance from weld according to Example 1.

Our most-realistic model for the shape of the end caps was generated by using a digital camera to photograph one of the end caps. The photograph included a vertical, graduated, steel scale with a horizontal width that we had measured. We digitized the photograph (including the scale) to generate values of $z_{cap}(i)$ and corrected these values for the 3.2 mm thickness of the end caps, as specified by the manufacturer. The corrected values of $z_{cap}(r)$ were fitted by cubic splines which were used to develop a mesh for a commercial, finite-element software package that computed the microwave frequencies. Here, r was the vertical distance measured from the cylindrical axis of the vessel, and $z_{cap}$ was a coordinate that measures the distance from the weld (where the central section of the vessel meets the end cap) to the outer surface of the end cap. The solid, red curve in FIG. 9 displays the top half of $z_{cap}(r)$. The values of $z_{cap}(r)$ are subject to errors from imperfections of the camera. Therefore, we did not use the digitized values directly. Instead, we scaled the vertical coordinates so that the inner radius of the end caps was equal to the inner radius of central section: $r_{max}=a$. (This assumption is consistent with our observations made using a borescope and using probes. A small difference between $r_{max}$ and a might be hidden by the welds inside the vessel where the end caps join the central section.) We treated the scale factor for the horizontal coordinates as an adjustable parameter $z_{end} \equiv z_{cap}(r=0)$. Thus, the photograph-based model has three parameters (L,a,$z_{end}$) that were fitted to the frequency data.

Figure 10:
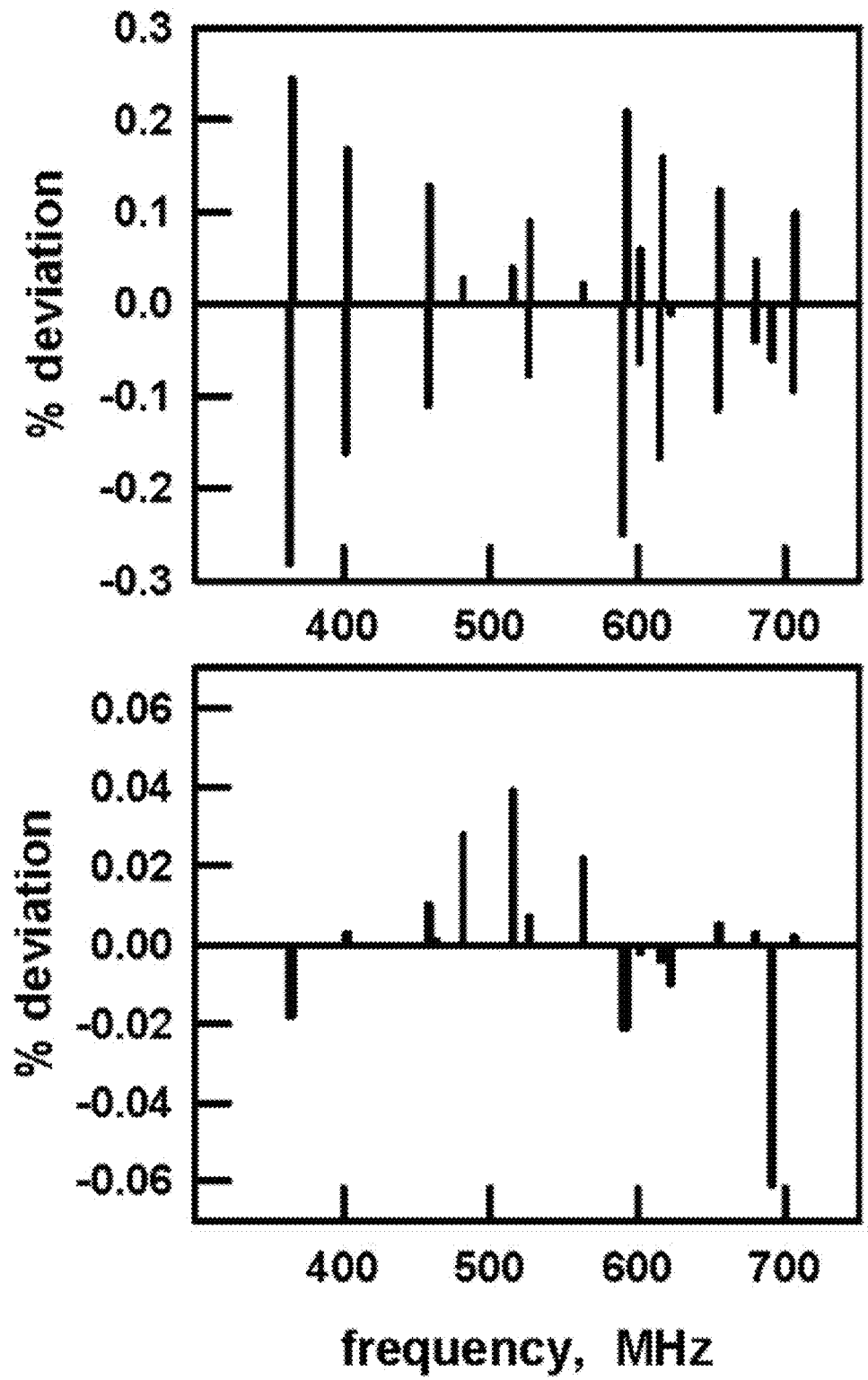
FIG. 10 shows a graph of percent deviation of a measured resonance frequencies from a best fit to a shape before (top panel) or after (bottom panel) averaging doublet frequencies versus frequency according to Example 1.

We tested two FE models based on the photographed end cap. The first model (Model 1A) had a circular cross-section and was used to fit 16 values of ($f_{meas}+g_{meas}$) that remain after the frequencies of all the doublets were averaged. For this model, the deviations are listed in Table 2 in the column "doublets averaged" and the deviations are plotted in the lower panel of FIG. 10. The best values of the parameters are L=1.3248 m, a=0.25021 m, and $z_{end}$=0.14144 m. The volume of the photograph-based, FE model is $V_{photo}$=295.73±0.17 L. We determined the standard uncertainty of $V_{photo}$ from the residuals of the fit $\Delta f \equiv (f_{meas}+g_{meas}-f_{calc})$. The fractional standard deviation of the residuals $\sigma(\Delta f/f)$ is a measure of the fractional uncertainty of each of the lengths (L, a, $z_{end}$); therefore, the fractional uncertainty of the volume is $3\sigma(\Delta f/f)$. The residuals of the resonance fit are the largest contributor to the microwave volume measurement (see Table 3).

To account for the observed frequency splittings, we modified the first photograph-based model so that the central section of the vessel had an elliptical cross-section with semimajor axis a(1+e), semiminor axis a/(1+e), and e=0.0026. (The end caps also had elliptical cross-sections.) This model (Model 1B) had the same values of L, a, $z_{end}$ and $V_{photo}$ as the model with circular cross-sections. The calculated frequency splittings are shown in FIG. 7. An elliptical cross-section splits the TE111 modes, but it does not split the TE211 doublets; however, these doublets had splittings as large as 0.0027. (FIG. 7) This discrepancy is evidence that that the cross-section is more complicated that an ellipse. In Table 2, under the heading "all frequencies", we list the deviations of the 26 values of ($f_{meas}+g_{meas}$) from the values of $f_{calc}$ obtained using the circular cross-section model. The deviations are also graphed in the top panel of FIG. 10.

Averaging the doublets before fitting the frequencies eliminated the parameter e from the FE model, greatly reducing the time for computing $f_{calc}$. Averaging also reduced the standard deviation $\sigma(\Delta f/f)$ by a factor of 7 from 0.00136 to 0.00019.

The standard deviation $\sigma(\Delta f/f)$ is a contribution to the relative uncertainty of the vessel's dimensions; the corresponding uncertainty in the vessel's volume is $3\sigma V$. For the "photo" model, this contribution is 0.17 L; for the "spheroid" model this contribution is 0.14 L. We note that $\sigma(\Delta f/f)$ did not come either from noise in measuring ($f_{meas}+g_{meas}$) or from noise in the environment (e.g., temperature fluctuations). When a measurement of $f_{meas}$ is repeated, the results reproduced within $10^{-6} f_{meas}$ or less. Thus, $\sigma(\Delta f/f)$ resulted from the imperfections of our model for the shape of the cavity. That is, $\sigma(\Delta f/f)$ was a measure of modeling errors, not noise.

In Table 2, the column $Q_{calc}/Q_{meas}$ compares the values of $Q_{meas} \equiv f_{meas}/(2g_{meas})$ with the values of Q calculated using finite element models, assuming the electrical conductivity of the steel is $\sigma_s = 4 \times 10^6$ S/m and that the relative magnetic permittivity of the steel at microwave frequencies $\mu_s$=1. The values of $Q_{calc}/Q_{meas}$ are independent of frequency; they have the average and the standard deviation ($Q_{calc}/Q_{meas}$)=8.00±0.23. The frequency independence of $Q_{calc}/$ $Q_{meas}$ is consistent with $Q_{meas}$ originating from the microwave skin depth [$\delta_s$ in Eqs. 7, 8, 10] and not, for example, in the cables or instruments used to measure $Q_{meas}$. The factor of 8 implies that the quantity ($\mu_s/\sigma_s$) is 64 times larger than that used to estimate $Q_{calc}$. The vessel was made of ferromagnetic steel; therefore, it is likely that $\mu_s \gg 1$ at microwave frequencies. The effective value of the electrical conductivity $\sigma_s$ could be reduced because the interior surfaces of the vessel are rough on the scale of the microwave skin depth $\delta_s$. The microwave fields extend into the vessel's steel walls; therefore, the microwave frequencies overestimate the vessel's volume by a fraction of order $\delta_s A_{vessel}/V_{vessel} \approx (1.3 \pm 0.6) \times 10^{-5}$, where $A_{vessel}$ is the internal surface area of the vessel. The uncertainty of this overestimate contributes an uncertainty 0.002 L to the volume of the vessel. We added this uncertainty in quadrature with $\sigma_f(\Delta f/f)$ to obtain the result $$V_{photo}(295.73 \pm 0.17)L. \tag{12}$$

Model 2: Hemispheroidal End Caps.

The second shape model assumed that the end caps are hemispheroids with a semiminor axis b and two semimajor axes of length a, where a is also the radius of the central section. Thus, the hemispheroidal model has three parameters (L,a,b) and the volume $V = \pi a^2(L + 4b/3)$. The best-fit values are L=1.34154 m, a=0.25021 m, b=0.12129 m and the standard deviation $\sigma_f(\Delta f/f)$ of the fit was $1.6\Delta 10^{-4}$. These values of L, a, lead to the volume $$V_{spheroid}(295.66 \pm 0.14)L, \tag{13}$$

where the k=1 uncertainty is $3\sigma(\Delta f/f)$. (See Table 3 for additional uncertainties.) Table 2 lists the scaled frequency deviations $\Delta f/f \equiv (f_{meas} + g_{meas} - f_{calc})/f$ for the hemispheroidal end caps in the column labelled "spheroid". The standard deviation $\sigma(\Delta f/f)$ for the hemispheroidal end caps is slightly smaller than the standard deviation for the photograph-based end caps (0.00016 compared with 0.00019). This is a small surprise. Both model shapes have three adjustable parameters; therefore, we expected that the photographed-based profile would fit the frequency measurements better than the semi-elliptical profile.

Comparing Eqs. 12 and 13, we find ($V_{photo}/V_{spheroid} - 1) = 0.00024$. This comparison shows that we could accurately model the volume within the vessel even if the information in the photograph were not available and/or if the thicknesses of the vessel's walls were unknown.

TABLE 2

| Mode | $f_{meas} + g_{meas}$ (MHZ) | $f_{calc}$ (MHz) photo | $10^3 \Delta f/f$ all frequencies | $10^3 \Delta f/f$ doublets Averaged photo | $10^3 \Delta f/f$ doublets Averaged spheroid | $Q_{meas}$ | $Q_{calc}/Q_{meas}$ |
|---|---|---|---|---|---|---|---|
| TE111 | 363.541 | 364.602 | −2.91 | −0.20 | −0.20 | 1690 | 8.23 |
| TE111 | 365.520 | 364.602 | 2.52 | −0.20 | −0.20 | 1690 | 8.23 |
| TE112 | 401.666 | 402.324 | −1.64 | 0.03 | 0.04 | 1980 | 8.13 |
| TE112 | 403.011 | 402.324 | 1.70 | 0.03 | 0.04 | 1996 | 8.06 |
| TE113 | 457.604 | 458.137 | −1.17 | 0.08 | 0.10 | 2372 | 8.11 |
| TE113 | 458.751 | 458.137 | 1.34 | 0.08 | 0.10 | 2372 | 8.11 |
| TM010 | 463.774 | 463.754 | 0.04 | 0.04 | −0.01 | 2694 | 7.58 |
| TM011 | 481.647 | 481.509 | 0.28 | 0.28 | 0.15 | 2481 | 7.83 |
| TM012 | 514.887 | 514.682 | 0.39 | 0.39 | 0.24 | 2334 | 8.21 |
| TE114 | 525.592 | 525.991 | −0.76 | 0.09 | 0.10 | 2850 | 7.98 |
| TE114 | 526.489 | 525.991 | 0.94 | 0.09 | 0.10 | 2866 | 7.94 |
| TM013 | 562.770 | 562.666 | 0.18 | 0.18 | 0.07 | 2507 | 7.79 |
| TE211 | 589.340 | 590.947 | −2.72 | −0.23 | −0.23 | 1694 | 8.19 |
| TE211 | 592.288 | 590.948 | 2.26 | −0.23 | −0.23 | 1694 | 8.19 |
| TE115 | 600.852 | 601.254 | −0.67 | −0.02 | −0.02 | 3281 | 7.94 |
| TE115 | 601.645 | 601.254 | 0.64 | −0.02 | −0.02 | 3309 | 7.88 |
| TE212 | 614.695 | 615.767 | −1.75 | 0.01 | 0.03 | 1818 | 8.09 |
| TE212 | 616.860 | 615.768 | 1.76 | 0.01 | 0.03 | 1827 | 8.05 |
| TM014 | 622.567 | 622.620 | −0.09 | −0.09 | −0.09 | 2637 | 7.71 |
| TE213 | 654.102 | 654.926 | −1.27 | 0.05 | 0.10 | 1967 | 8.13 |
| TE213 | 655.837 | 654.928 | 1.37 | 0.05 | 0.10 | 1958 | 8.16 |
| TE116 | 679.773 | 680.005 | −0.35 | 0.10 | −0.04 | 3561 | 7.84 |
| TE116 | 680.382 | 680.006 | 0.54 | 0.10 | −0.04 | 3607 | 7.73 |
| TM015 | 690.990 | 691.414 | −0.62 | −0.62 | −0.45 | 2881 | 7.38 |
| TE214 | 705.189 | 705.854 | −0.96 | 0.12 | 0.21 | 2101 | 8.37 |
| TE214 | 706.708 | 705.857 | 1.19 | 0.12 | 0.20 | 2180 | 8.06 |
| Average |  |  | 0.01 | 0.01 | 0.00 |  | 8.00 |
| Std. dev. |  |  | 1.43 | 0.19 | 0.16 |  | 0.23 |

Shape Perturbations of Models 1 and 2.

In an attempt to improve the models for the shape of the vessel, we used boundary perturbation theory to explore modifications of the shape of hemispheroidal caps and modifications of the cylindrical section of the vessel. A small deformation (perturbation) of the cavity's shape made by moving the boundary inward increases the frequency $f_N$ of the mode with indices N by $\Delta f_N$ $$\frac{\Delta f_N}{f_N} = \frac{\int_{\Delta V_{pert}} (\mu_0 |H_N|^2 - \varepsilon_0 |E_N|^2) dV}{\int_V (\mu_0 |H_N|^2 + \varepsilon_0 |E_N|^2) dV}, \tag{14}$$

where V is the volume of the original cavity, $\Delta V_{pert}$ is the decrease in the volume of the cavity, and $H_N$ and $E_N$ are the magnetic and electric fields of the mode before the boundary is modified. We used Eq. 14 to avoid time-consuming, FE calculations of $f_N$ every time a function or a parameter was changed. We considered functions of the form $$\Delta z(r) = \sum_n [d_n \cos(n\pi r/a) + e_n \sin(n\pi r/a)] \tag{15}$$

-continued
$$\Delta a(z) = \sum_n [d_n \cos(n\pi z/L) + e_n \sin(n\pi z/L)],$$

where $\Delta z(r)$ is the thickness of the volume removed from each end cap and $\Delta a(z)$ is the thickness of the volume removed from the cylindrical section in the range $-L/2 < z < L/2$. For each function, we considered n=0, 1, 2, and 3. The function $\Delta z(r)$ did not improve the fits to the frequency data nor did it change the volume significantly. However, the function $\Delta a(z)$ with $d_0 = (2.7 \pm 0.5) \times 10^{-4}$ and $d_1 = -(4.1 \pm 0.8) \times 10^{-4}$ reduced $\sigma(\Delta f/f)$ from 0.00016 to 0.00011 and decreased the microwave-determined volume of the vessel by $\Delta V_{pert} = -0.03$ L. The other terms in $\Delta z(r)$ contributed less to $\Delta V_{pert}$. Because $\Delta V_{pert}$ requires two additional parameters and decreases the volume by only $-0.00010 \times V_{micro}$ (which is $1/5^{th}$ of the uncertainty of $V_{micro}$), we treated $\Delta V_{pert}$ as an un-modelled volume similar to the volumes associated with the vessel's ports and welds. We ignored $\Delta V_{pert}$ when computing $V_{micro}$ and included $|\Delta V_{pert}|$ in the uncertainty of $V_{micro}$.

Determining the Microwave Volume and its Uncertainty.

We considered three models for the shape of the vessel: Model 1A assumed a cylindrical central section with photo-based end caps; Model 1B assumed elliptical central section with photo-based end caps; and Model 2 assumed a cylindrical central section with spheroidal end caps. Model 1A had 3 fitted lengths and many lengths implicit in the digitized profile; Model 1B had the parameters of Model 1A plus a 4th parameter fitted to the TE111 splittings; and Model 2 had only 3 fitted parameters. The photo-based models and the spheroid model yielded nearly identical results [$(V_{photo}/V_{spheriod} - 1) = 0.00024$], and all models fitted the values of $(f_{meas} + g_{meas})$ nearly equally well: $u_r(V_{photo}) = 0.00057$ and $u_r(V_{spheroid}) = 0.00048$. Adding parameters to the spheroid model did not improve its performance. Our best estimate of the vessel's volume from microwave measurements is the average $$V_{micro} = (V_{spheroid} + V_{photo})/2 = (295.69 \pm 0.18)L. \quad (16)$$

where the contributors to $u_r(V_{micro})$ are collected in Table 3. The largest contributor originates in the differences $\Delta f/f = (f_{meas} + g_{meas} - f_{calc})/f$. For the two models, these differences are highly correlated. (Compare the columns labeled "photo" and "spheroid" in Table 2.) The average and standard deviation of $\langle(\Delta f/f)_{spheroid} - (\Delta f/f)_{photo}\rangle = 0.00001 \pm 0.00008$. This correlation is not surprising, because both models represent the same vessel with mathematically smooth cavities. Because of this correlation, the models are not fully independent. Therefore, Table 3 and Eq. 16 assumed that the smallest uncertainty of the two models (0.00048) applies to the average. In Table 3, the un-modeled volumes of the vessel's welds and ports have opposite signs; their sum was used as an estimate of the uncertainty.

TABLE 3

| Phenomenon | Estimate | Value |
|---|---|---|
| Microwave antennas | | 0.00002 |
| Ports (+29 cm³) and weld beads (−130 cm³) | un-modeled volume value | 0.00034 |
| Elliptical cross-section | $e^2$ | 0.000007 |
| Differences ($f_{meas} + g_{meas} - f_{calc}$) | $3\sigma_f(\Delta f/f)$ | 0.00048 |
| Perturbations to shape | | 0.00010 |
| Penetration of microwaves into steel | $u(\delta_s)A_{vessel}/V_{vessel}$ | 0.000006 |
| Measurement and fit of resonance frequency | fit residuals | 0.000001 |
| Root Sum of Squares | | 0.00060 |

All of the contributions to $u_r(V_{micro})$ in Table 3 are measures of our incomplete understanding; instrumental uncertainties are much smaller.

Measuring the Thermal and Pressure Expansion of the Vessel: Thermal Expansion.

We estimated the thermal expansion of the vessel from the values of $(f_{meas} + g_{meas})$ for 11 microwave modes while the thermostat in the laboratory was set at two different temperatures: $T_1 \approx 19°$ C. and $T_2 \approx 22°$ C. For the modes listed in Table 4 we computed the ratios $$\Re = (f+g)_{T1}/(f+g)_{T2} \quad (17)$$

For the doublets, the values of $(f_{meas} + g_{meas})$ were averaged before calculating $\Re$. Giving equal weight to each mode in Table 4, the average and standard deviation is $\Re = 1 + (34.44 \pm 0.19) \times 10^{-6}$. Remarkably, the values of $\Re$ are the same for TE and TM modes and they have no detectable frequency-dependence. The observations imply that the thermal expansion of the vessel was isotropic, a result that is expected because the vessel was made entirely from one alloy. [Note: in contrast with the ratios $(f+g)_{T1}/(f+g)_{T2}$, the ratios $f_{T1}/f_{T2}$ have a small frequency dependence because the temperature dependences of $\mu_s$ and $\sigma_s$ in Eq. 7 lead to a temperature-dependent microwave skin-depth $\delta_s$. The temperature dependence of $\delta_s$ is not related to the thermal expansion of the vessel.]

During the thermal expansion measurements, the vessel was evacuated and the change in the vessel's temperature was inferred from three thermometers that we calibrated. A thermistor taped to the top quarter of the vessel indicated a change of 3.09 K; a thermistor taped to the bottom quarter of the vessel indicated a change of 2.77 K; and, a commercially manufactured temperature probe inserted into a port on the top of the vessel indicated a change of 3.05 K. For computing the thermal expansion, we assumed that the temperature change was the average of the thermistor readings (2.93±0.16) K, where the k=1 uncertainty was chosen because ±0.16 K was the range spanned by the three thermometers. With these assumptions and the observed isotropy, the linear coefficient of thermal expansion is $\alpha_T = (11.75 \pm 0.64) \times 10^{-6}$ K$^{-1}$ and the thermal expansion coefficient of the volume was $$(\partial V/\partial T)_p/V = 3\alpha_T = (35.3 \pm 1.9) \times 10^{-6} K^{-1}. \quad (18)$$

Our result for $\alpha_T$ agrees with the value $11.5 \times 10^{-6}$ K$^{-1}$ reported for carbon steel SA414-G.

TABLE 4

| Mode | f/MHz | $10^6(\Re - 1)$ |
|---|---|---|
| TE111 | 365 | 34.33 |
| TE112 | 403 | 34.11 |
| TE113 | 458 | 34.21 |
| TM011 | 482 | 34.63 |
| TM012 | 515 | 34.52 |
| TE114 | 526 | 34.36 |
| TM013 | 562 | 34.32 |
| TE115 | 601 | 33.96 |
| TE212 | 614 | 34.24 |
| TM014 | 622 | 34.44 |
| TE116 | 680 | 34.44 |

TABLE 4-continued

| Mode | f/MHz | $10^6(\Re - 1)$ |
|------|-------|-----------------|
| Mean |       | 34.44           |
| Std. Dev. |   | 0.19            |

Measuring the Thermal and Pressure Expansion of the Vessel: Pressure Expansion.

Assuming the walls of the vessel have a uniform thickness t, we expect that the pressure expansion of the vessel will be greater than that of a thin-walled spherical shell and less than that of a long, thin-walled cylindrical shell $$\frac{3(2a)}{4tE}(1-v) < \frac{1}{V}\frac{dV}{dp} < \frac{(2a)}{4tE}(5-4v) \quad (19)$$

or $$0.35 < \frac{10^6 \text{ kPa}}{V}\frac{dV}{dp} < 0.62$$

wherein 2a=0.5 m was the shell's diameter, t=3.9 mm was the thickness of the cylindrical section of the vessel, E=2×$10^{11}$ Pa was Young's modulus for the hot-rolled carbon steel alloy SA414-G, and v=0.28 was a typical value of Poisson's ratio for steels.

We attempted to measure the pressure expansion of the vessel; however, the results led to an unsolved puzzle. We measured $[f_N(p, T)+g_N(p, T)]$ for the 15 microwave modes listed in Table 5 and tried to interpret the results using the 3-parameter model for the vessel (a cylinder of length L and radius a with hemispheroid caps, each with semi-axes a, a, and b.).

TABLE 5

| Mode | f (MHz) | $10^6(\partial f/\partial p)/f$ (k/Pa) |
|------|---------|-----------------------------------------|
| TE111 | 364 | -0.274 |
| TE112 | 402 | -0.276 |
| TE113 | 457 | -0.269 |
| TE114 | 525 | -0.288 |
| TE211 | 589 | -0.341 |
| TE115 | 600 | -0.295 |
| TE212 | 615 | -0.286 |
| TE213 | 653 | -0.276 |
| TE116 | 679 | -0.334 |
| TM010 | 463 | -0.300 |
| TM011 | 481 | -0.182 |
| TM012 | 514 | -0.144 |
| TM013 | 562 | -0.121 |
| TM014 | 621 | -0.131 |
| TM015 | 689 | -0.171 |

Here, the subscript "N" represents all of the mode indices. The measurements were conducted while the vessel was near 22° C. and filled with argon at pressures near 0 kPa, 206 kPa, and 390 kPa. First, we averaged the frequencies of each doublet; then, we removed the effect of the refractive index of the argon by multiplying $(f_N+g_N)$ by $[\in(p, T)]^{1/2}$, where $\in(p, T)$ is the dielectric constant of argon; and then we formed the ratio $$\Im_N \equiv \frac{[f_N(p, T) + g_N(p, T)][\varepsilon(p, T)]^{1/2}}{[f_N(0, T_{ref}) + g_N(p, T_{ref})]}[1 - \alpha_T(T - T_{ref})] \quad (20)$$

to account for the thermal expansion of the vessel from an arbitrary reference temperature $T_{ref}$. We fitted the values of $\Im_N$ at 0 kPa, 206 kPa and 390 kPa to obtain 15 values of $(df_N/dp)f_N$ listed in Table 5. (The results of preliminary measurements taken at higher pressures are consistent with Table 5.) If the pressure expansion were isotropic, we would expect $(dV/dp)/V \approx -3 \times (df_N/dp)/f_N$. For the TE modes in Table 5, the average and standard deviation $-10^6(df_N/dp)/f_N = -0.293 \pm 0.026$ kPa$^{-1}$, which implies the pressure expansion $10^6$ kPa×$(dV/dp)/V = 0.88 \pm 0.08$ is somewhat larger than that of a long cylinder, as estimated using Eq. 19. However, the values of $-10^6(df_N/dp)/f_N$ for the TM modes span a factor of 2.4. We considered the possibility that the pressure expansion, unlike the temperature expansion, is anisotropic. To do so, we used the FE software to calculate the partial derivatives of the frequencies $f_N(L,a,b)$ with respect to the three lengths L, a, and b of the model vessel with spheroidal end caps. We used these derivatives, together with the 15 values of $(df_N/dp)/f_N$ to obtain 15 equations of the form, $$\frac{df_N}{dp} = \frac{\partial f_N}{\partial L}\frac{\partial L}{\partial p} + \frac{\partial f_N}{\partial a}\frac{\partial a}{\partial p} + \frac{\partial f_N}{\partial b}\frac{\partial b}{\partial p}, \quad (21)$$

each with three unknowns, $\partial L/\partial p$, $\partial a/\partial p$, and $\partial b/\partial p$. However, a least-squares estimate of the unknowns yielded $10^6 \partial L/\partial p = -0.54$ m/kPa, $10^6 \partial a/\partial p = 0.30$ m/kPa, and $10^6 \partial b/\partial p = 4.91$ m/kPa. The negative value of $\partial L/\partial p$ is puzzling, and we do not understand why the measured values of $(df_N/dp)/f_N$ for TM modes differ from the values for the TE modes.

The estimate $(1/V)(dV/dp) = 0.62 \times 10^{-6}$ kPa$^{-1}$ for a cylinder [Eq. 19w] predicts the fractional increase in vessel's volume at its maximum working pressure (1.38 MPa) is $\Delta V/V = 0.00086$. Therefore, the volume that we determined while the vessel was evacuated was a good approximation to the volume at any pressure up to the maximum working pressure. (The same volume change, $\Delta V/V = 0.00086$, would occur if the temperature of the vessel were increased by 24 K.)

We used microwaves to determine the volume of a commercially manufactured vessel with an estimated k=1 uncertainty $u_r(V_{micro}) = 0.00060$. The largest contributor to $u_r(V_{micro})$ are the differences $\Delta f/f = (f_{meas} + g_{meas} - f_{calc})/f$. Two models for the end caps gave similar differences; the differences were not reduced by adding parameters to these models. This suggested that reducing the uncertainties requires better models for the rest of the vessel. Consistent with this suggestion, a two-parameter perturbation $\Delta V_{pert}$ to the cylindrical section of the vessel reduced $\Delta f/f$, however, $\Delta V_{pert}$ was only $\frac{1}{5}^{th}$ of $u_r(V_{micro})$.

We treated the quantity $(\mu_s/\sigma_s)$ as a parameter to fit the values of $Q_{meas}$. We could improve $Q_{meas}$ by determining $(\mu_s/\sigma_s)$ from measurements of $f_{micro}$ and $g_{micro}$ using a small cavity with an accurately known, simple shape and with finely polished interior surfaces of carbon steel SA414-G.

Because $V_{micro}$ and $V_{vessel,gas}$ agree within their combined uncertainties, it was unlikely that the microwave technique was subject to large unknown errors. No difficulty exists for determining $V_{micro}$ for much larger vessels with uncertainties less than 0.1%.

We achieved the small uncertainty $u_r(V_{vessel,gas}) = 0.00018$ because the vessel was in a well-thermostatted laboratory that made it possible to measure the changes of the vessel's average temperature (and the temperature of the gas within it) with an uncertainty of 0.02 K after waiting a few hours for thermal equilibration. In contrast, the microwaves can be used to measure the volume of an un-thermostatted vessel located outdoors. Even if the average temperature of an outdoor vessel had an uncertainty of 10 K, this uncertainty would contribute only 0.00035 to the relative uncertainty of $V_{micro}$. This estimate uses the measured thermal expansion $[(\partial V/\partial T)_p/V=(35.3\pm1.9)\times 10^{-6}\ K^{-1}]$ which is also consistent with the thermal expansion of the steel used to make the vessel.

Example 2

Determining a Mass of a Gas in a Vessel with Microwave and Acoustic Resonances

We determined mass M of argon gas contained within a 0.3 m³ commercially manufactured vessel ("vessel") with a relative standard uncertainty of $u_r(M)=0.0016$ at 0.6 MPa by combining the measured argon pressure and the measured microwave and acoustic resonance frequencies within the vessel with an accurate equation of state for argon. (All stated uncertainties correspond to the 68% confidence level.) Here, we show that the microwave results accurately predict the wavenumbers $k_{calc}$ of the four lowest-frequency acoustic modes of the gas. When we compared $k_{calc}$ to the measured wavenumbers $k_{meas}$, which included corrections for known perturbations, such as the vessel's calculated pressure-dependent center-of-mass motion (but not the vessel's vibrational modes), the inconsistency of the ratio $k_{meas}/k_{calc}$ among the modes was the largest component of $u_r(M)$. Because the resonance frequencies $f_{calc}$ of the acoustic modes depend on the average speed of sound (and therefore the average temperature) of the gas in the vessel, first-order perturbation theory predicts that $f_{calc}$ for a rigid cylindrical cavity is independent of linear temperature gradients. Consistent with this prediction, the average of $f_{meas}$ for the 3 lowest-frequency, non-degenerate longitudinal modes changed only $\Delta f_{meas}/f_{meas}=(0.2\pm1.3)\times 10^{-4}$ when, near ambient temperature, we heated the vessel's top 13 K warmer than its bottom. However, we observed a linear dependence on $\Delta T$ for the average of $f_{meas}$ for the nearly-degenerate doublet modes, which the rigid cylinder theory does not predict. We argue that the linear dependence on $\Delta T$ was caused by anisotropic changes in the vessel's shape in response to the applied temperature gradient. We conclude that resonance frequencies can be used to "weigh" the compressed gas in much larger vessels, which are possibly made from ferromagnetic steel and possibly at high pressures in un-thermostatted environments; therefore, resonance measurements will have many applications in gas metrology.

Figure 11:
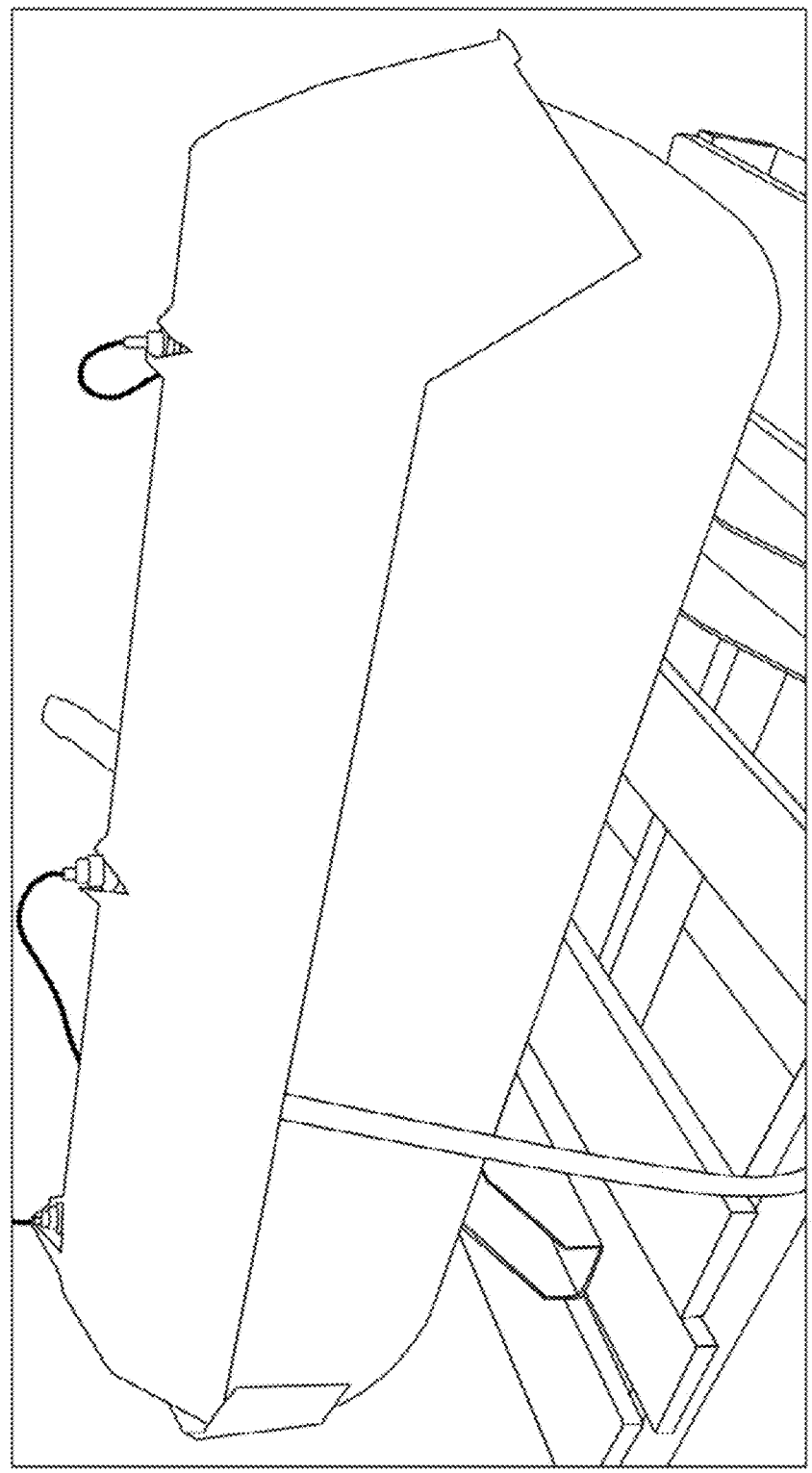
FIG. 11 shows a photograph of a vessel according to Example 2.

As mentioned, we measured the frequencies of the acoustic resonances in argon within a 0.3 m³-volume of a commercially manufactured, un-thermostatted vessel ("vessel") made of ferromagnetic steel. A photograph of the vessel is shown in FIG. 11. Here, we combined the acoustic frequencies and a model shape to determine the average speed of sound (and the average temperature) of the argon within the vessel. As shown schematically in FIG. 12, the speed of sound, together with the measured pressure and an accurate equation of state for argon determined the average mass density $\langle\rho\rangle$ of the argon. The product $\langle\rho\rangle V_{vessel}=M$ was the mass of the argon in the vessel; its relative uncertainty was $u_r(M)=0.0016$, as estimated from the standard deviation of 4 values of M obtained with 4 low-frequency acoustic modes at a pressure near 0.6 MPa. The largest contributor to $u_r(M)$ was the unmodeled interaction between the acoustic modes of the gas and the frequency-dependent compliance of the vessel's walls.

To gain insight into the present determination of M, it is convenient to combine the virial expansion for the equation of state $p(\rho, T)$ with the pressure expansion of the speed of sound $u^2(p, T)$ to obtain the relation $$M = \frac{\gamma_0 p V_{tank}}{u^2}\left[1 + (\beta_a - B)\frac{p}{RT} + \dots\right], \quad (22)$$

wherein p is the pressure, u is the speed of sound, $\gamma_0 \equiv C_p/C_V$ is the zero-pressure heat-capacity ratio, and $\beta_a$ and B are the acoustic and the density virial coefficients, respectively. Because the temperature appears only in the correction terms in equation 22, we replaced the difficult problem of accurately measuring the average temperature of a large volume of gas with the easier problem of accurately measuring the average speed-of-sound in the gas. The acoustic wavenumbers of a resonant cavity are insensitive to linear temperature gradients (in the first order of perturbation theory); therefore, resonance determinations of the speed of sound are only weakly dependent on temperature gradients in the gas. [Heating the vessel's top 13 K warmer than the vessel's bottom increased the acoustic frequencies of the lowest three non-degenerate modes by $\Delta f_{meas}/f_{meas}=(0.2\pm1.3)\times 10^{-4}$. See column "meas" in Table 7.] The acoustic and microwave techniques that we used were scalable to very large volumes. Our resonance techniques can be used to weigh compressed gas in much larger vessels, at higher pressures, and in un-thermostatted environments. Such a large vessel could be used as a gas source or a gas collector during the calibration of large gas-flow meters and also in in large-scale gas metrology.

The vessel had a complicated shape that required fitting at least 3 lengths to determine the volume $V_{vessel}$ with the relative uncertainty $u_r(V_{vessel})=0.0006$. The vessel was made of ferromagnetic steel that reduced the Qs of the microwave modes by a factor of 8. For the vessel, a ratio: (radius)/(side walls thickness) was ≈64 so that perturbations of the acoustic frequencies from the elasticity of the vessel's walls dominated the uncertainty of the present determination of the mass of the gas in the vessel.

The Vessel and the Measurement Techniques.

Here, we describe the vessel using information provided by the manufacturer, together with the volume and shape information that we deduced from microwave measurements.

Construction of the Vessel.

The vessel was commercially manufactured for use as an air receiver with a maximum operating pressure of 1.38 MPa (Silvan Industries, Inc., Marinette, Wis., USA, Part Number A10031). The manufacturer stated that it was designed and built to comply with ASME Code, Section VIII, Div. 1, 20th Edition. As shown in FIG. 11, the vessel was a horizontal, approximately circular cylinder with hemispheroidal "end caps" (called "heads") welded to each end of the cylinder. The manufacturer's drawings indicate that the cylindrical section has a length of 1.3 m, a diameter of 0.51 m, and a wall thickness of 3.9 mm. The cylindrical section had been manufactured from a plate, and it had a weld bead along its entire length on both its outside and inside surfaces. The end caps were "2:1 semielliptical heads." Their shapes were approximately oblate hemispheroids (that is, half of an ellipse of revolution) with a 0.12 m semiminor axis and a 3.2 mm wall thickness. The end caps had a joggle (a short cylindrical extension that fit inside the cylindrical section) to facilitate welding. We estimated that the joggles plus the weld beads inside the vessel occupied approximately 130 cm$^3 \approx 0.00043$ V$_{vessel}$ in the vessel interior. We did not modify the vessel for this research.

The vessel's walls were penetrated by 7 ports. At each port, the manufacturer had welded a threaded fitting to the outside of the vessel. We inserted the acoustic transducers into the two ports near either end of the top surface of the vessel. Microwave antennas were installed in two other ports and a thermometer was installed in a fifth port. We capped the remaining two ports, located on the axis of each end cap, with threaded brass plugs that were sealed with polytetrafluoroethylene (PTFE) tape. One port was unused, and the other was connected to the argon source. They were the largest ports and, when capped, each had an internal volume of approximately 30 cm$^3$. The internal volumes of the 5 smaller ports totaled 29 cm3.

The vessel was manufactured from the ferromagnetic, hot-rolled carbon steel alloy SA414-G. The measured half-widths of the microwave modes were 8 times larger than those expected for the modes in a vessel made out of a non-magnetic metal ($\mu_s=1$) that had the electrical conductivity ($\sigma_s=4\times10^6$ S/m) of the alloy SA414-G. [We use the subscript "s" to denote the properties of the steel walls of the cavity and $\mu_s$ is the relative magnetic permeability.] If the factor of 8 resulted solely from ferromagnetism, $\mu_s \approx 64$ and the microwave fields would decay within the vessel's walls with the characteristic length $\delta_s=1.5\times10^{-6}$ m at 400 MHz.

Non-Circular Cross-Section of Vessel.

The external appearance of the vessel (FIG. 11) suggested that it had an axis of rotational symmetry. In cavities with an axis of rotational symmetry, many of the microwave modes and many of the acoustic modes are doubly degenerate; that is, they occur in overlapping pairs. The doubly degenerate microwave modes of this vessel were split into easily resolved components; the same was true for the acoustic modes. To account for these splittings, we considered modeling the vessel's cross section as a cylinder with radius a and with a deviation function $\Delta a(\phi)$, where $\phi$ measures the angle about the cylinder's axis. If $\Delta a(\phi)$ has periodicity $\pi$, the deviation can describe an ellipse and it can be used to fit the splittings of the TE111 doublets. The splitting of the TE111 doublets was consistent with an elliptical cross section with semi-major axis a(1+e), semi-minor axis a/(1+e), and e≈0.0026. However, the splittings of other doublets provided evidence that the cross section was more complicated than elliptical. Known complications include the ports on the top of the vessel; another plausible complication is a discontinuity of the derivative d[$\Delta a(\phi)$]/d$\phi$ at the weld parallel to the vessel's axis that sealed the rolled plate into a cylindrical shape. Instead of searching for a function $\Delta a(\phi)$ that could fit all the measured doublets, we averaged the measured doublet frequencies before fitting them by models with circular cross sections. After averaging, any remaining effects of $\Delta a(\phi)$ will be of order e$^2$. In principle, these effects could be calculated using second-order shape perturbation theory. Fortunately, for values of e~0.0026, the second-order perturbations will be negligible compared with other errors.

Volume and Shape of the Vessel from Microwave Frequencies: Literature Results for Mathematical Cavities.

The problem of determining the shape of a cavity from its resonance frequencies has a long history in mathematical physics but does not have a general solution that achieves the small uncertainties. A frequently-discussed "solution" is Weyl's formula for N(f), the number of resonance frequencies less than f $$N(f)=a_V V(f/c)^3+a_A A(f/c)^2+a_L L(f/c). \quad (23)$$

(This version applies to smooth-walled cavities in 3 dimensions.) In Weyl's formula, V is the volume of the cavity; A is the surface area of the cavity; L is a characteristic length; and c is the speed of sound for acoustic waves or the speed of light for microwaves. In equation 23, the coefficient $a_V=4\pi/3$ for acoustic modes and $a_V=8\pi/3$ for microwave modes. Although the values of $a_V$ are independent of the cavity's shape, the coefficients $a_A$ and $a_L$ depend on the cavity's shape and must be regarded as unknowns. We estimated the volume of an ideal rectangular cavity with dimensions 7 m×9 m×11 m by assuming the velocity of sound was 345 m/s (appropriate for dry air at ambient conditions) and by counting the 73895 acoustic modes of the cavity between 0 Hz and 1000 Hz. Using only the cubic term in equation 23, the estimated volume of the cavity has an uncertainty on the order of 5%. When $a_A$ was fitted to the counted N(f), the uncertainty of the estimated volume was reduced to 0.1%. Because N(f) increases as f$^3$, the separation between the frequencies decreases as f$^{-2}$. Near 1000 Hz, the average spacing of the frequencies is 0.014 Hz. The modes of a real cavity have non-zero half-widths and their frequencies will fluctuate with temperature and pressure.

Numerical results for the volume and shape of this vessel.

We correlated the measured spectrum of microwave resonances using several models for the shape of the vessel. From the microwave measurements we concluded that V$_{vessel,micro}$=295.66×(1±0.0006) L, where the largest component of the uncertainty of the volume was 3$\sigma_f$($\Delta$f/f=0.00048. Here $\sigma_f$ is the standard deviation of the fractional differences between the measured and calculated microwave frequencies. We also measured the internal volume of the vessel using an accurate gas-expansion method and obtained the result V$_{vessel,gas}$=295.771×(1±0.00017) L, where the uncertainty was dominated by imperfect pressure and temperature measurements. Thus, the microwave measurements and the more-accurate gas expansion measurements, which shared neither theory nor instruments, yielded consistent results within combined uncertainties. The gas-expansion measurement of V$_{vessel,gas}$ required careful measurements of temperature differences; in contrast, the temperature entered into the microwave measurement of V$_{vessel,micro}$ only through the vessel's thermal expansion: ($\partial$V/$\partial$T)$_p$/V=(35.3±1.9)×10$^{-6}$ K$^{-1}$. Therefore the microwave measurement of V$_{vessel,micro}$ could tolerate a temperature uncertainty of 10 K without significantly increasing the uncertainty of Vvessel$_{,micro}$.

After averaging the doublets, the simplest shape that was consistent with the microwave frequencies was a vessel with a cylindrical center section of length L and hemispheroidal end caps with a semiminor axis b and two semimajor axes of length a, where a is also the radius of the central section. This model has three parameters (L,a,b) and the volume V=$\pi$a$^2$(L+4b/3). The best-fit values were L=1.34154 m, a=0.25021 m, b=0.12129 m. We used this model shape as an input to commercial, finite-element (FE) software to calculate the acoustic resonance frequencies of the vessel. We used a digitized photograph of one end cap to develop a different model shape for the vessel. The photograph-based model had a nearly identical volume and nearly identical microwave and acoustic frequencies as the spheroidal model.

Description of Acoustic Transducers.

We used parts from a commercially manufactured buzzer (Radio Shack, 273-0060) as an acoustic transmitter (106 in FIG. 2). The transmitter was a 27 mm diameter metal diaphragm (156) driven by an attached piezoceramic disk (158). Using flexible silicone caulk, we sealed the diaphragm into a recess that we had machined in the male thread end (150) of a brass pipe fitting (1"×¾" NPT reducer 154, 1" NPT male thread 166). We drilled a pressure release hole (155) (1 mm diameter) through the side of the male thread (166) to allow the pressure across the diaphragm (156) to equalize. The space behind the diaphragm (160) was filled with glass wool (168) to dampen the Helmholtz resonance. We soldered the source's signal lead (164) to the center contact (172) and soldered the ground lead (162) to the shield contact (174) of a commercially-manufactured (MPF Products, A0660-1-W) hermetic, grounded, coaxial SMA feed-through (152) with a coaxial contact (176). We silver-soldered the shield contact (174) to a ¾" NPT cored plug (153). We used PTFE tape to seal the threads of the two pipe fittings when assembled.

The acoustic receiver (108 in FIG. 3) was a commercially manufactured (Knowles, MD9765ASZ-0), 9.7 mm diameter×6.5 mm thick electret condenser microphone (180). After removing the Helmholtz chamber from the front of the microphone's diaphragm, we mounted the microphone in a cavity that had been machined in a PTFE insulator disk (182) so the diaphragm was flush with the disk's surface. We press-fit the PTFE disk into the male-threaded end (150) of a brass pipe fitting (1"×¾" NPT reducer 154); the compressed PTFE held the microphone in place. The pipe fitting was sealed to a smaller brass pipe fitting (¾"×½" NPT reducer 153) with PTFE tape. We silver soldered the smaller pipe fitting to the welding lip (175) of a commercially-manufactured (MPF Products, A1980-2-W) hermetic SMA feedthrough (152) that had a floating shield (174), ceramic insulator (176), and coaxial contact (177). The microphone's low signal lead (186) and high signal lead (188) passed through a small hole drilled through the back of the PTFE disk (182), and then they were soldered to the feed-through contacts (172) and (174). Three holes (0.4 mm diameter) drilled through the PTFE disk equalized the outside pressure with the gas volume (184) behind the microphone (180).

Spectrum of Acoustic Resonance Frequencies.

As a first approximation, we calculated the acoustic spectrum using a right circular cylindrical cavity with radius a=25 cm and length L=150.34 cm; the length was chosen to make the volume of the cylinder equal to the volume of the vessel. This cylindrical approximation provided: (1) a notation that identifies the lower-frequency acoustic modes, (2) estimate of the half-widths of the acoustic modes, (3) a model for calculating the dependence of the frequencies on temperature gradients, and (4) exact results that we used to test our implementation of the finite element (FE) software packages. Here, we discuss the cylindrical model and then the results of the FE calculations.

Theoretical Spectrum of a Cylindrical Cavity in a Cylindrical Shell.

We calculated the unperturbed resonance frequency $f_{lmn}^{(0)}$ of each acoustic mode of a gas in an ideal, perfectly-cylindrical cavity surrounded by a rigid shell (the vessel's walls) using:

$$\left(\frac{2\pi f_{lmn}^{(0)}}{u}\right)^2 = K_{lmn}^2 \equiv \left(\frac{l\pi}{L}\right)^2 + \left(\frac{\beta_{mn}}{a}\right)^2. \quad (24)$$

In equation 24 u is the speed of sound in the gas; $K_{lmn}$ is an acoustic eigenvalue (wavenumber); $\beta_{mn}$ is the $n^{th}$ root to $dJ_m(z)/dz=0$ counting the first root with n=0, and where $J_m(z)$ is the $m^{th}$ order Bessel function; and l, m, and n, are non-negative integers. Equation 24 neglects the non-zero thermal conductivity κ and the non-zero shear viscosity η of the gas. These transport properties lead to well-understood energy losses at the gas-shell boundary that generate a thermal contribution $g_T$ and a viscous contribution $g_v$ to the half-widths of the resonances $g_{lmn}$. They also reduce the resonance frequency $f_{lmn}$ by $g_T+g_v$. We define the thermal penetration length $\delta_T \equiv [\kappa/(\rho C_p \pi f)]^{1/2}$ and the viscous penetration length $\delta_v \equiv [\eta/(\rho \pi f)]^{1/2}$, where ρ is the gas's mass density and $\rho C_p$ is the gas's constant-pressure heat capacity per volume. For a cylindrical cavity the thermal contribution to the half-width is:

$$g_T = \frac{f(\gamma-1)\delta_T}{2a(1-m^2/\beta_{mn}^2)}\left[1+\frac{a}{L}\left(1-\frac{m^2}{\beta_{mn}^2}\right)(2-\delta_{l0})\right], \quad (25)$$

where $\gamma \equiv C_p/C_V$ is the heat capacity ratio, and the viscous contribution is $$g_v = \frac{f\delta_v}{2a(1-m^2/\beta_{mn}^2)}\left[1-\left[1-\frac{a}{L}(2-\delta_{l0})\right]\frac{(\beta_{mn}^2-m^2)}{K_{lmn}^2 a^2}\right], \quad (26)$$

where the Kronecker delta symbol $\delta_{l0}$ equals 1 when l=0 and equals 0 when l≠0. In equations 25 and 26, we neglected several terms that are small at the pressures explored here (200 kPa to 600 kPa). The neglected terms include the contribution to $g_T$ from the penetration of the thermal wave into the steel walls, energy dissipation throughout the volume of the gas and contributions to the frequency from imperfect thermal and viscous accommodation at the gas-wall boundary.

The assumption of a rigid shell can be relaxed by developing a model for the elastic recoil of a thick-walled, cylindrical shell in response to the acoustic oscillations of argon gas enclosed within the cavity. Such a relaxed model considered two classes of shell deformations: (1) stretching deformations of the cylindrical shell that are axially symmetric (independent of the azimuthal angle θ) and (2) bending deformations of the endplates. The relaxed model can be to estimate the effect of recoil on the resonance frequencies of the longitudinal modes of the gas in their resonator. Such predicted provided that the radial and axial stretching deformations of the shell decrease the resonance frequencies of the gas by a sum of terms in the form:

$$\frac{\Delta f_{stretch}}{f_{lmn}^{(0)}} \approx \frac{(\rho u^2)_{gas}}{(\rho u^2)_{shell}}\left(\frac{a}{h}\right)\sum_i \frac{s_{i,lmn}}{1-(f_{lmn}^{(0)}/f_{s,i})^2}, \quad (27)$$

wherein the dimensionless mode-dependent parameters $s_{i,lmn}$ are on the order of unity; h is the thickness of the shell, and the frequencies $f_{s,i}$ are the resonance frequencies of the empty shell. Bending deformations of the flat endplates of their resonator can be considered, but we do not expect such an endplate model to describe the hemispheroidal endcaps on our vessel. If we apply the estimate in equation 27 to our vessel, then the prefactor of the sum is approximately $5\times10^{-4}$ when the gas is argon at 1 MPa and $(\rho u^2)_{shell}=220$ GPa. Because the present data span the range p≤0.6 MPa; we expect the perturbation $\Delta f_{strech}/f_{lmn}^{(0)}$ to be negligible except near the shell's resonance frequencies $f_{s,i}$. The vessel had a comparatively large ratio: a/h≈64; therefore, the walls of the vessel had many low-frequency bending modes. In view of these circumstances, we treated the elastic response of the shell as an empirical frequency perturbation $\Delta f_{recoil}$ that is proportional to $(\rho u^2)_{gas}$ such that the coefficient of proportionality might have a complicated frequency dependence.

When a gas-filled spherical shell is considered to be a free body, the center-of-mass (CM) of the system {shell+gas} will not move during the acoustic oscillations; however, the CM of the shell will oscillate out of phase with the gas for gas modes that lack spherical symmetry. Similarly, for a gas-filled cylindrical cavity surrounded by a cylindrical shell, CM oscillations increase the frequencies of the longitudinal acoustic modes (l00) by an amount $$\frac{\Delta f_{CM,1}}{f_{l00}^{(0)}} = \frac{4}{l^2\pi^2}\frac{M_{gas}}{M_{shell}}\delta_{l,odd}\delta_{m0} \quad (28)$$

for modes with odd reflection symmetry about the plane bisecting the cylinder's length, i.e., l is an odd integer; however, the frequencies of the even symmetry (l00) modes, where l is an even integer, are unchanged. During the present measurements, our vessel was loosely fastened to a wooden shipping pallet (FIG. 11); therefore, it oscillated as a free body when driven by the acoustic oscillations of the gas within it. [The free-body approximation would fail if $M_{pallet}$ were comparable to or larger than $M_{shell}$ and if the attachment of the vessel to the pallet were so strong that the resonance frequencies associated with the relative motion of the vessel and the pallet were comparable to the acoustic frequencies.]

The reasoning that leads to equation 28 also predicts that CM motion will increase the acoustic resonance frequencies of transverse modes with m=1 by $$\frac{\Delta f_{CM,2}}{f_{01n}^{(0)}} = \frac{M_{gas}}{M_{shell}(\beta_{1n}^2 - 1)}\delta_{l0}\delta_{m1}. \quad (29)$$

The resonance frequencies for transverse modes with m>1 will be unchanged. For mixed modes with lodd and m=1, the acoustic oscillations of the gas will generate torques that will tend to rotate the vessel about an axis perpendicular to the gas's motion. This rotation will increase the acoustic resonance frequencies in proportion to $I_{gas}/I_{shell}$, the ratio of the moments of inertia about the rotation axis. We have not estimated this effect.

When the vessel was at ambient temperature and filled with argon at 0.6 MPa, the ratio $M_{gas}/M_{shell}$ was 0.03710; under these conditions, the relative frequency increases predicted by equations 28 and 29 for the (1,0,0), (3,0,0), and (0,1,0) gas modes in a rigid cylindrical shell are 0.0150, 0.00167, and 0.0155, respectively. For comparison, we calculated $\Delta f_{CM,1}/f_{l00}^{(0)}$ and $\Delta f_{CM,2}/f_{010}^{(0)}$ numerically with finite-element software (COMSOL 3D, FlexPDE) using the ellipsoidal end-cap model for the vessel's shape that we determined from microwave measurements; the numerical calculations predict increases of 0.0151, 0.00172, and 0.0154 for the (1,0,0), (3,0,0), and (0,1,0) modes, respectively, which are remarkably close to the analytic predictions for a perfect cylinder.

The effects CM,1 and CM,2 [equations 28 and 29] as well as $\Delta f_{recoil}$ are proportional to the density of the gas; hence they are nearly proportional to the pressure. We combine the listed perturbations to obtain an expression for the measured frequencies $f_{lmn,meas}$ $$f_{lmn,meas} = f_{lmn}^{(0)} - g_T - g_v + \Delta f_{recoil} + \Delta f_{CM,1} + \Delta f_{CM,2} \quad (30)$$

When applying equations 28 and 29, we used the value $M_{shell}$≈86 kg, which was provided by the manufacturer and includes the 10 cm high "saddle legs" welded to the vessel. A comparison of FIG. 16 (both panels) shows that equations 28 and 29 account for nearly all the pressure-dependence of the frequencies of the (100), (300), and (010) modes.

Finite-Element Calculations of the Acoustic Spectra of Gas-Filled Model Vessels.

We calculated the acoustic eigenvalues of gas modes in the vessel's cavity using two different numerical methods. We also found nearly identical results for two differently-shaped cavities. The differences between the results from these calculations are much smaller than other uncertainties.

We used the FlexPDE software to calculate the acoustic wavenumbers of two model cavities to analyze the microwave frequencies. Both model cavities had cylindrical center sections; one had spheroidal end caps and the second had axi-symmetric end caps with shapes deduced from a photograph. (See Table 6.) The wavenumbers calculated using the FlexPDE software for these 2D axisymmetric models differed by no more than 0.02% for values of the wavenumber $k_{lmn} = 2\pi f_{lmn}/u$ spanning the range from 2 m$^{-1}$ to 11 m$^{-1}$. (These values of k correspond to 100 Hz<$f_{lmn}$<600 Hz when the vessel was filled with argon at 20° C. and 100 kPa.) We also used the COMSOL software to calculate the wavenumbers for the photo-based profile using a full three-dimensional model formulation. For the nine lowest-frequency modes, the COMSOL 3D wavenumbers averaged 0.001% higher than the 2D FlexPDE wavenumbers. This excellent agreement gave us confidence in the accuracy of the wavenumbers calculated using the FE software. (Both numerical methods assume that the walls of the vessel are rigid and neither method includes the perturbations from the viscosity and thermal conductivity of the gas.)

TABLE 6

| | | $10^4 (k/k_{ref} - 1)$ | | | | |
| | $k_{ref}/m^{-1}$ | | | Measured | | $Q_{cyl}$ |
| Mode | spheroidal | Photo | Cylinder | 0 MPa | 0.6 MPa | 0.2 MPa |
|---|---|---|---|---|---|---|
| 1, 0, 0 | 2.08924 | −2.7 | −8.6 | 0.7 | 2.2 | 829 |
| 2, 0, 0 | 4.17465 | −2.6 | 0.5 | −3.8 | −10.5 | 1172 |
| 3, 0, 0 | 6.25178 | −2.5 | 17 | −10.7 | −13.2 | 1435 |
| 0, 1, 0 | 7.44209 | −0.8 | −104 | 2.6 | −22.4 | 1726 |
| 1, 1, 0 | 7.83464 | −1.8 | −230 | −1.5 | 74.2 | 1483 |
| 4, 0, 0 | 8.31446 | −2.5 | 42 | | | 1657 |
| 2, 1, 0 | 8.67212 | −2.0 | −238 | −17.0 | −23.2 | 1485 |
| 3, 1, 0 | 9.88584 | −1.6 | −221 | | | 1512 |
| 5, 0, 0 | 10.3523 | −3.0 | 82 | | | 1853 |
| 4, 1, 0 | 11.3578 | −0.6 | −197 | | | 1562 |
| 0, 2, 0 | 12.2865 | −1.3 | −57 | 9.6 | 57.2 | 1684 |

Table 6 summarizes many of the results of this section. For comparisons, the column $k_{ref}$ lists the 11 smallest wavenumbers calculated for the cylindrical cavity with spheroidal end caps. The column "photo" compares $k_{ref}$ with the wavenumbers for a cylindrical cavity with end cap shapes determined from a photograph. The column "cylinder" compares $k_{ref}$ with the wavenumbers of a cylindrical cavity with the same volume. The column "$Q_{cyl}$" lists the values of Q=$f_{calc}$/

$[2(g_v+g_T)]$ a calculated using equations 24, 25, and 26 for an ideal cylinder at 0.2 MPa and 296 K. For the present measurements, a useful approximation is $Q_{calc}=Q_{cyl}\times(p/0.2 \text{ MPa})^{1/2}\times(T/296 \text{ K})^{-2/3}$.

Theory of the Effects of a Temperature Gradient.

When the temperature T is a function of position within the volume of gas in the vessel, the speed of sound u in the gas will be a function of position as well. Sound waves will travel faster in warmer regions of the vessel and slower in cooler regions. This variation in the speed of sound affects the distance that sound waves travel as they propagate through the volume, and thereby changes the frequencies at which resonance occurs. The change of the resonance frequency depends on the symmetry of the mode and on the symmetry of the temperature field. Moreover, if the temperature gradient breaks the symmetry of a degenerate mode, then the degeneracy will be lifted, and components of the multiplet will change by different amounts. We set up a first-order perturbation theory calculation of the effects of temperature gradients on the resonance frequencies of a gas in a rigid, perfectly cylindrical cavity. Then, we state the results obtained with a model temperature gradient that resembles the gradient generated in the laboratory. (The perturbation calculation ignores the thermal expansion and contraction of different parts of the shell that change the shape of a real cavity.) Finally, we present generally applicable insights.

Figure 13:
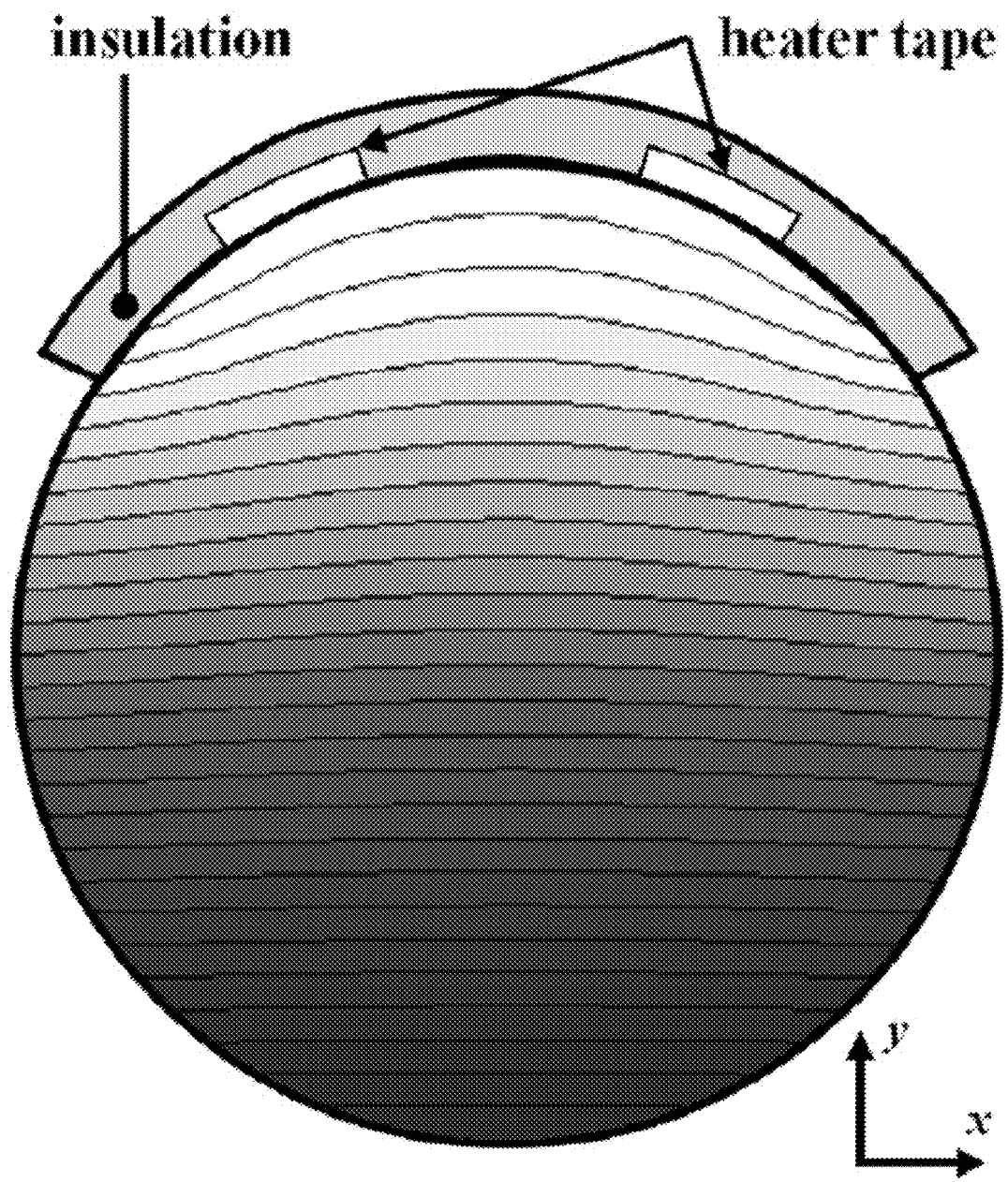
FIG. 13 shows isotherms in a cross-section of a vessel having a top-to-bottom temperature gradient according to Example 2.

As an illustrative example, we chose a temperature profile $T_w(r_w)$ at the wall of the cavity that was independent of the axial coordinate z and was a linear function of the height measured from the center of the cavity (a sin θ), except for a 90° sector at the vessel's top where the temperature was constant. (See FIG. 13.) (The angle θ is measured from the horizontal.) The temperature T(r) in the interior of the cavity was determined from the Laplace equation $\nabla^2 T(r)=0$, subject to the Dirichlet boundary condition $T(r)=T_w(r_w)$ at the wall $r=r_w$. We denote the average temperature over the volume of the gas as $T_0=\langle T(r)\rangle$. We expand the dimensionless temperature deviation, defined as $\tilde{\tau}(r)\equiv(T(r)-T_0)/T_0$, in the series $$\tilde{\tau}(r,\theta) = \tilde{\tau}_0 \sum_{j\geq 1} C_j \left(\frac{r}{a}\right)^j \cos\left[j\left(\theta - \frac{\pi}{2}\right)\right] \equiv \tilde{\tau}_0 \mathcal{J}(r,\theta) \quad (31)$$

where $\tilde{\tau}_0$ is a dimensionless scale factor and the Fourier coefficients $C_j$ can be calculated from the assumed boundary temperature distribution. FIG. 13 shows the isotherms (solid lines) for this temperature field. If the temperature difference between the top and bottom of the cavity is ΔT, then the scale factor is $\tilde{\tau}_0=(2-\sqrt{2})\Delta T/T_0$. For $T_0=296$ K, then $\tilde{\tau}_0$ has the values 0.014 and 0.026 when ΔT=7 K and 13 K, respectively.

In the reference state for the perturbation calculations, the gas in the cavity has a uniform temperature $T_0$, therefore the speed of sound $u_0=u(T_0)$ is independent of position; an acoustic mode is characterized by its velocity potential $\varphi_N(r)$ that is a solution of the Helmholtz equation $$\nabla^2 \varphi_N + \left(\frac{\omega_N^{(0)}}{u_0}\right)^2 \varphi_N = 0, \quad (32)$$

subject to the Neumann boundary condition $\hat{n}\cdot\nabla\varphi(r_w)=0$. The mode's resonance frequency $f_N^{(0)}=\omega_N^{(0)}/(2\pi)$ is given by equation 24. Here, the subscript N=(l,m,n,s) represents all the indices needed to identify an acoustic mode, and the superscript (0) indicates the unperturbed value. A convenient choice for the velocity potential is $$\varphi_{\ell mns} = J_m\left(\frac{\beta_{mn}r}{a}\right) \quad (33)$$
$$(\delta_{s1}\cos m\theta + \delta_{s2}\sin m\theta)\left[\delta_{\ell 0} + \delta_{\ell,even}\cos\left(\frac{\ell\pi z}{L}\right) + \delta_{\ell,odd}\sin\left(\frac{\ell\pi z}{L}\right)\right]$$

where $-L/2\leq z\leq L/2$, and the index s=1 or 2 selects one member of the doublet when m≠0. For nondegenerate modes (m=0), the index s is unnecessary and is therefore omitted because the sine function vanishes.

When the gas's temperature depends upon position according to equation 31, the Helmholtz equation including the non-uniform speed of sound is, for an ideal gas, $$\nabla^2 \Phi_N + \tilde{\tau}_0 \mathcal{J}(r)\nabla^2 \Phi_N + \frac{\omega_N^2}{u_0^2}\Phi_N = 0 \quad (34)$$

where $\Phi_N$ and $f_N=\omega_N/(2\pi)$ are the velocity potential and resonance frequency for the mode N when the perturbation $\tilde{\tau}_0 \mathcal{J}(r)\nabla^2\Phi_N$ is present. First-order perturbation theory predicts that the model gradient in equation 31 changes the resonance frequency $f_N$ from the unperturbed value $f_N^{(0)}$ by the fractional amount $$\frac{f_N - f_N^{(0)}}{f_N^{(0)}} = \frac{\tilde{\tau}_0}{2k_N^2 \Lambda_N V}\int_V \varphi_N \mathcal{J}\nabla^2\varphi_N\, dV + O(\tilde{\tau}_0^2), \quad (35)$$

where $\Lambda_N V \equiv \int_V \varphi_N^2\, dV$. Equation 35 is valid for degenerate and non-degenerate modes because the orientation of the doublet axes for the potential in equation 33 exploits symmetry of our model temperature gradient in equation 31. The angular integral for our model gradient in equation 35 vanishes for m=0, i.e. for all non-degenerate modes (l,0,n). For the degenerate modes (m>0), the angular integral in equation 35 is nonzero only for the Fourier component j=2m in equation 31. Therefore, equation 35 predicts, for m≥1, $$(s=1)\frac{f_{\ell mn} - f_{\ell mn}^{(0)}}{f_{\ell mn}^{(0)}} = \frac{(-1)^m \tilde{\tau}_0 C_{2m} W_{mn;mn}^{[2m]}}{2(1-m^2/\beta_{mn}^2)[J_m(\beta_{mn})]^2} \quad (36)$$

$$(s=2)\frac{f_{\ell mn} - f_{\ell mn}^{(0)}}{f_{\ell mn}^{(0)}} = -\frac{(-1)^m \tilde{\tau}_0 C_{2m} W_{mn;mn}^{[2m]}}{2(1-m^2/\beta_{mn}^2)[J_m(\beta_{mn})]^2} \quad (37)$$

where $$W_{mn}^{[2m]} \equiv \int_0^1 [J_m(\beta_{mn}\rho)]^2 \rho^{2m+1}\, d\rho, \quad (38)$$

and the coefficients $C_{2,m}$ are $\sqrt{2}(6\pi)$ for m=1 and $-\sqrt{2}(15\pi)$ for m=2. Equations 36 and 37 show that the components of a doublet are changed equal amounts but with opposite signs; thus the average change is zero. The second and third columns in table 2 list the fractional frequency changes multiplied by $10^4$, as predicted by equation 35 for 7 modes with the temperature differences ΔT=7 K and 13 K that were used in our measurements.

We now assert results from first-order perturbation theory that apply to any temperature field $\tilde{\tau}$ in an ideal cylindrical cavity without heat sources, provided that $\tilde{\tau}$ is a solution of Laplace's equation and $\langle\tilde{\tau}\rangle=0$, as follows: (1) $\Delta f_{lmn}/f_{lmn}^{(0)}$ from equation 35 vanishes for linear gradients, whether longitudinal or transverse; (2) $\Delta f_{lmn}/f_{lmn}^{(0)}$ vanishes for any mode unless $\tilde{\tau}$ is an even function of z about the mid-plane bisecting the cylinder's length; (3) for non-degenerate modes (m=0), $\Delta f_{l0n}/f_{l0n}^{(0)}$ vanishes unless $\tilde{\tau}$ has a Fourier component that is axially symmetric (independent of θ); (4) for degenerate modes (m>0), Fourier components of $\tilde{\tau}$ that are axially symmetric will shift but not split the doublet frequencies, whereas Fourier components of $\tilde{\tau}$ that are proportional to cos(2mθ) split the doublets equally upward and downward in frequency, so that the average frequency change is zero to first order.

Non-degenerate modes are a good choice because they are not changed by a temperature gradient (to first order) unless the gradient is axially symmetric and an even function of z, which is unlikely. Even if the temperature gradient is axially symmetric, which is more likely if the vessel is vertical, then non-degenerate modes are still the best because the z-dependence is not likely to be an even function of z. If degenerate modes are used, measure both members of the doublet and average their resonance frequencies.

Below, we discuss measurements of frequency changes generated by temperature gradients. The results are listed in the right-most column in Table 7. For the non-degenerate (1,0,0), (2,0,0) and (3,0,0) modes, the measured frequency changes are small and irregular: $|\Delta f_{meas}/f_{meas}| \leq 1.3 \times 10^{-4}$. For these three modes at $\Delta T=13$ K, the average and standard deviation of the frequency changes were $\Delta f_{meas}/f_{meas} = (0.2 \pm 1.3) \times 10^{-4}$ K. This null result is consistent with the perturbation calculation result that the first-order frequency change is zero.

TABLE 7

| Mode lMN | 1, $1^{ST}$ | 2, $1^{ST}$ | 1, $2^{ND}$ | 2, $2^{ND}$ | Meas |
|---|---|---|---|---|---|
| $\Delta T = 7$ K | | | | | |
| 1, 0, 0 | 0 | — | −0.19 | — | 0.6 |
| 2, 0, 0 | 0 | — | −0.23 | — | −0.3 |
| 3, 0, 0 | 0 | — | −0.17 | — | 0.8 |
| 0, 1, 0 | 1.6 | −1.6 | −0.17 | −0.22 | 5.9[a] |
| 1, 1, 0 | 1.6 | −1.6 | −0.19 | −0.21 | 7.4[a] |
| 2, 1, 0 | 1.6 | −1.6 | −0.19 | −0.19 | 4.5[a] |
| 0, 2, 0 | −0.5 | 0.5 | −0.20 | −0.20 | 2.1[a] |
| $\Delta T = 13$ K | | | | | |
| 1, 0, 0 | 0 | — | −0.65 | — | 1.1 |
| 2, 0, 0 | 0 | — | −0.79 | — | −1.3 |
| 3, 0, 0 | 0 | — | −1.03 | — | 0.8 |
| 0, 1, 0 | 3.0 | −3.0 | −0.58 | −0.76 | 11.4[a] |
| 1, 1, 0 | 3.0 | −3.0 | −0.59 | −0.74 | 13.8[a] |
| 2, 1, 0 | 3.0 | −3.0 | −0.65 | −0.65 | 8.6[a] |
| 0, 2, 0 | −1.0 | 1.0 | −0.71 | −0.71 | 4.7[a] |

[a]average for doublet

For the degenerate modes, the values of $\Delta f_{meas}/f_{meas}$ in Table 7 are as large as $14 \times 10^{-4}$ and they are consistent with the linear dependence $\Delta f_{meas}/f_{meas} \propto \Delta T$. The large magnitude and the unexpected linear dependence on $\Delta T$ led us to make $2^{nd}$ order calculations of the effect of a temperature gradient that is a linear function of the height in an ideal cylindrical vessel. The results of the $2^{nd}$ order calculation are also listed in table 2 in the columns labeled "1, $2^{nd}$" and "2, $2^{nd}$". As expected, the calculated $2^{nd}$ order values $\Delta f_{calc}/f_{calc}$ are smaller than the $1^{st}$ order values and do not explain the large magnitude of some $\Delta f_{meas}/f_{meas}$ values. Below, we present evidence that the measured linear dependence of $\Delta f_{meas}/f_{meas}$ on $\Delta T$ for the doublets resulted from a change in the shape of the vessel that was produced by the asymmetric heating.

Isothermal Measurements of Shell Resonances and Gas Resonances.

We used wide-range isothermal scans of the acoustic spectra to identify the resonance modes of the empty vessel (the "shell") and the resonance modes of the gas. The frequencies of the shell modes have a strong pressure-dependence; therefore, many will "cross" the frequencies of gas modes. For frequencies near mode crossings (known as "avoided crossings" in optical spectroscopy), the shell and the gas interact strongly. Because we lack an accurate theory for the complicated shell motion, modes that have such crossings cannot be used for gas metrology. After the overview, we discuss accurate measurements of the frequencies $f_{meas}$ and half-widths $g_{meas}$ of the acoustic (gas) modes at 0.2 MPa, 0.4 MPa, and 0.6 MPa. For many gas modes, the differences between $f_{meas}$ and the FE-calculated frequencies $f_{calc}$ ale tend to zero as the pressure tends to zero. For the three lowest-frequency gas modes, $|f_{meas}/f_{calc}-1|<1.4\times10^{-3}$ between 0 MPa and 0.6 MPa, provided that the center-of-mass frequency corrections, equations 28 and 29, are made. Any one of these modes could determine the mass of the gas in the cavity with a relative uncertainty on the order of $2.8\times10^{-3}$. The remaining gas modes had large, unmodeled pressure-dependencies which limit their usefulness for gas metrology.

Figure 14:
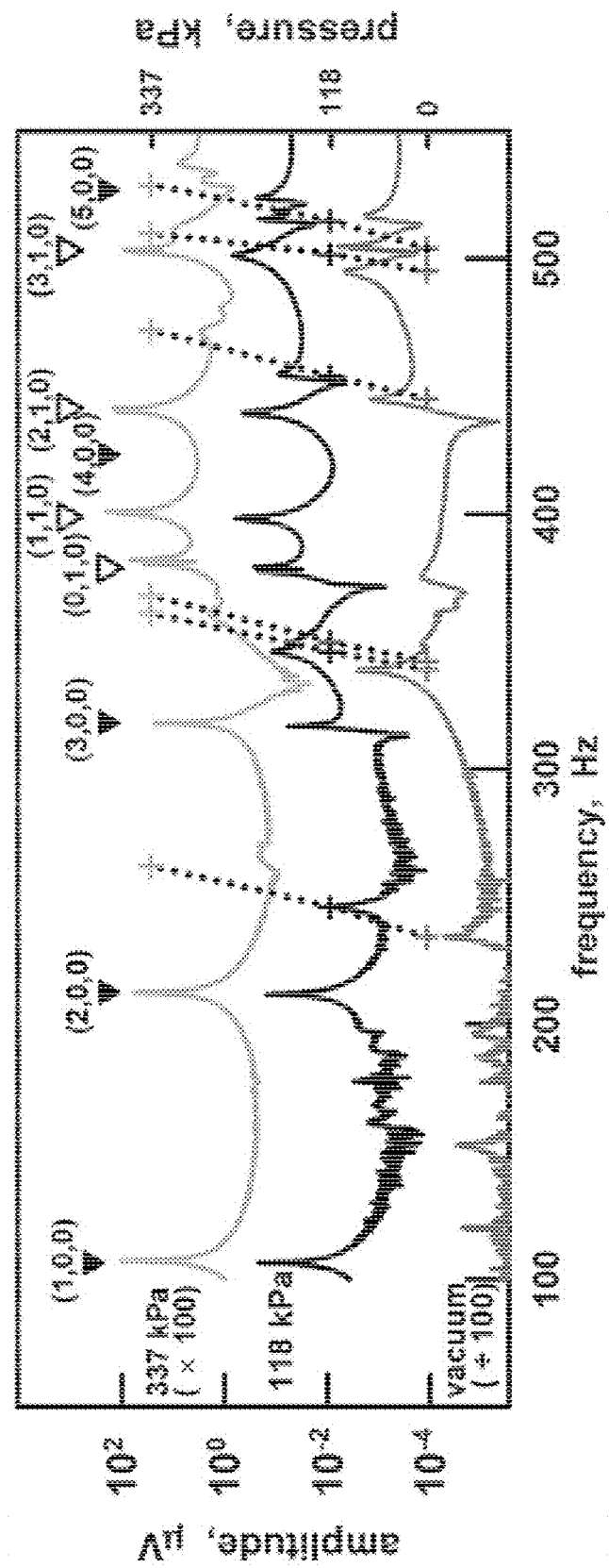
FIG. 14 shows a graph of amplitude of an acoustic signal (left-hand y-axis) and locations of acoustic modes at three pressures versus frequency and a pressure dependence (right-hand y-axis) of several shell modes (dotted lines and plus symbols) versus frequency according to Example 2.

FIG. 14 is a scan of the vessel's acoustic spectrum measured under three different conditions: (1) evacuated with a mechanical pump, (2) filled with argon at 19° C. and 118 kPa, and, (3) filled with argon at 21° C. and 337 kPa. (To avoid overlapping curves, the amplitude of the vacuum spectrum was divided by 100 and the amplitude of the 337 kPa spectrum was multiplied by 100.)

As indicated in FIG. 14, all of the acoustic modes were detected near the frequencies predicted by the FE models, except for the (4,0,0) mode. To understand the absence of the (4,0,0) mode, we calculated the ratio of the amplitudes $A_{4,0,0}/A_{3,0,0} \approx 0.0036$, where $A_{l,m,n}=(\varphi(r,z)^2/Q)_{l,m,n}$ and $\varphi(r,z)$ is the amplitude of the acoustic eigenfunction at the position of the transducer. The spheroidal FE model predicts $|\varphi(r,z)|_{4,0,0}/|\varphi(r,z)|_{3,0,0}=0.056$ and the cylinder model predicts $Q_{4,0,0}/Q_{3,0,0}=1.15$. We conclude that the signal from the (4,0,0) mode was too small to detect because the transducers happened to be located near pressure nodes of that mode. We note that the estimate $A_{4,0,0}/A_{3,0,0} \approx 0.0036$ ignores the frequency-dependences of the sensitivity of the acoustic transducers.

The vacuum scan in FIG. 14 has high-Q resonances at 234 Hz, 339 Hz, 342 Hz, 445 Hz, 495 Hz, 504 Hz, 560 Hz, and at other frequencies. We identify these resonances as shell resonances and we indicate them in FIG. 14 by plotting blue "+" characters, either just above or just below the vacuum scan. When the pressure in the shell is increased from 0 kPa to 118 kPa and then to 337 kPa, the lower-frequency shell resonances change to higher frequencies and lower Qs. In FIG. 14, this frequency change is indicated by dotted lines connecting the "+" characters. We argue that the increase of the shell resonance frequencies with pressure occurred because the pressure-induced tension in the shell made a significant contribution to the "spring constant" for these modes. Between 0 MPa and 0.6 MPa, the frequency of the first shell mode (FIG. 15) increased by 20% from 234 Hz.

Figure 15:
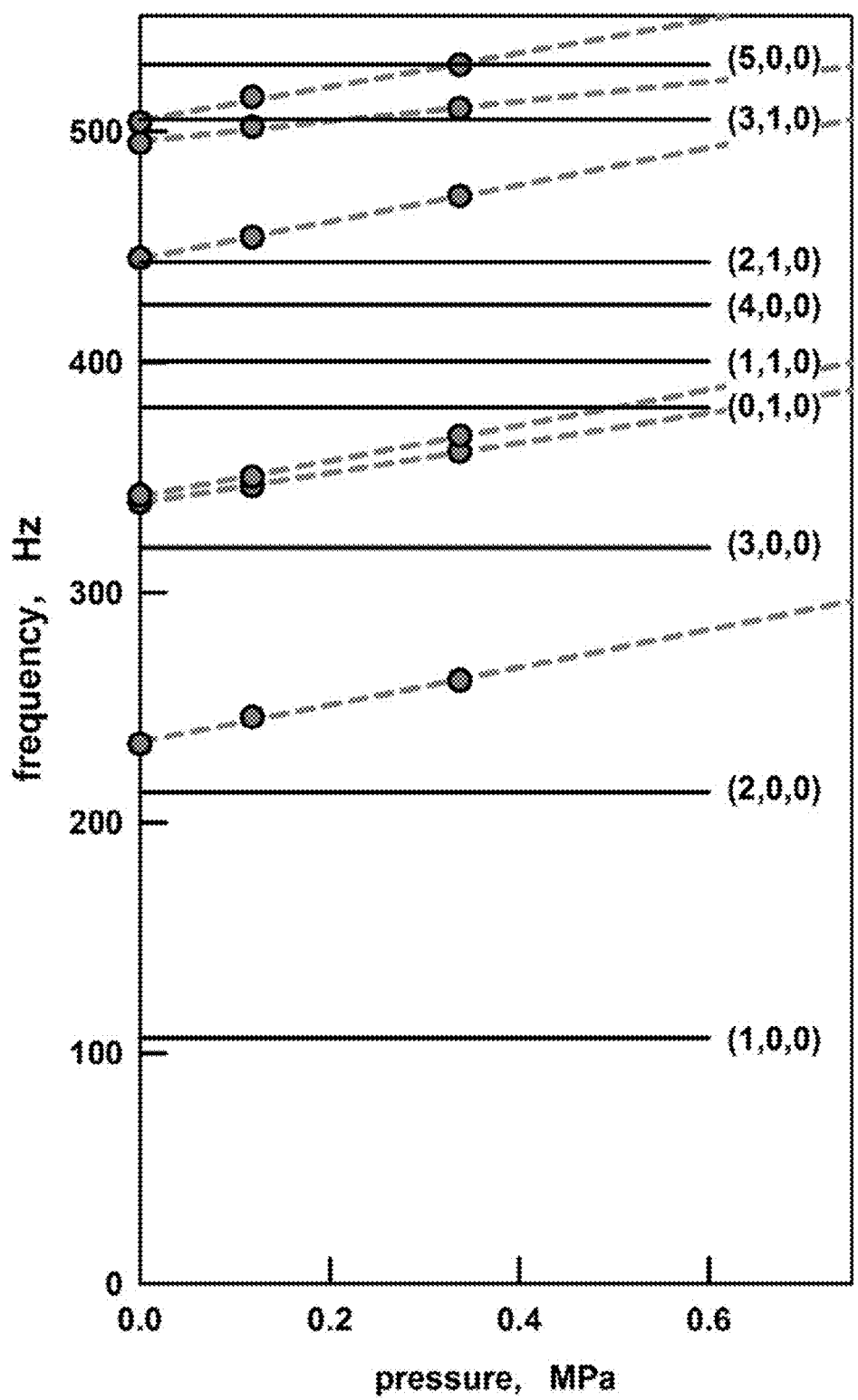
FIG. 15 shows a graph of frequencies of shell modes (symbols and dashed lines) and acoustic modes (solid lines) versus pressure according to Example 2.

We suspect that the resonances of the shell influence the resonances of the gas. FIG. 15 shows that, as the pressure increases, the shell modes will cross the gas modes. At low pressures, the 445 Hz shell resonance approaches the (2,1,0) gas resonance. The "avoided crossing" of these two modes "pushes" the gas resonance to lower frequencies, as shown in greater detail in FIG. 17 below.

For the higher-frequency shell modes (e.g., fshell=504 Hz), the slopes of the dotted curves in FIG. 14 and FIG. 15 might differ from $dp/df_{shell}$ if we made an error in associating a particular peak in the scan at p=337 kPa with the shell resonance at p=0, $f_{shell}$=504 Hz.

Precise Isothermal Measurements of Acoustic Frequencies and Half-widths.

We measured the frequencies $f_{meas}$ and half-widths $g_{meas}$ of 7 gas modes at 0.2 MPa, 0.4 MPa, and 0.6 MPa while the vessel was on a pallet in a thermostatted laboratory, as shown in FIG. 11. This set of measurements took two days. Each measurement of $f_{meas}$ and $g_{meas}$ included stepping the frequency of the sound generator up and down through a resonance (or through a doublet) and then fitting resonance functions to the in-phase and quadrature voltages generated by the sound detector. The tabulated data are available from the authors upon request. During these measurements, we recorded the temperatures indicated by two, calibrated, thermistor thermometers. One thermometer was fastened to the top of the vessel; the other was fastened to the bottom of the vessel. The average of the two thermometers varied slowly between 20.9° C. and 21.9° C.; the temperature difference, $T_{top}-T_{bottom}$ ranged from 0.08 K to −0.04 K.

To compare the measured frequencies $f_{meas}$ with the values of the wavenumbers $k_{calc}$ predicted by the FE models, we formed the ratio $\Re$;

$$\Re = k_{meas}/k_{calc} = 2\pi(f_{meas}-\Delta f_{calc})/[u(p,T)k_{calc}], \quad (39)$$

which has the value $\Re=1$ when measurements and calculations agree perfectly. In equation 39, we used values for the speed of sound of argon u(p, T). The frequency-correction term $\Delta f_{calc}$ in equation 39 always includes the thermoacoustic boundary correction $\Delta f_{calc}=-g_{calc}$, where $g_{calc} \equiv g_T + g_v$ is the half-width. In the cylinder model, this correction was small; its maximum value $g_{calc}/f_{meas}$=0.0006 occurs for the (1,0,0) mode at 200 kPa and the values decrease as $(pf)^{-1/2}$. Because the correction was small, we estimated it using the cylinder model calculation of $g_{calc}$.

Figure 16:
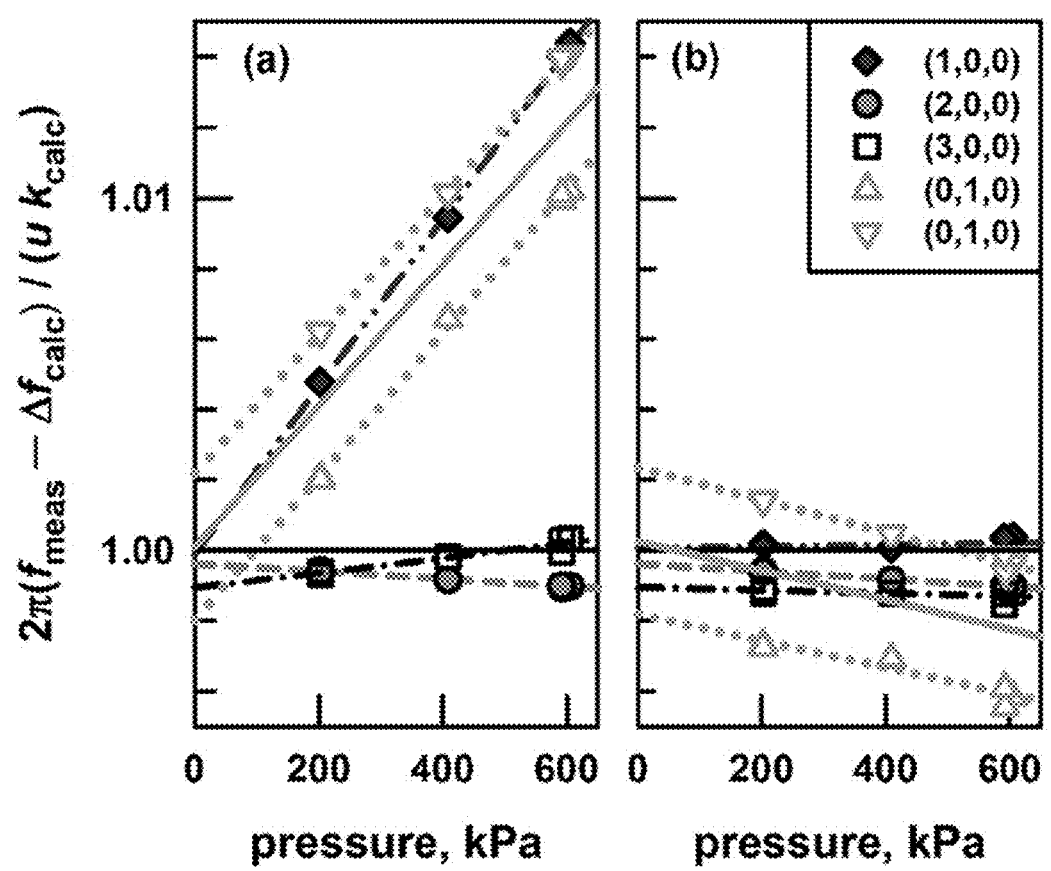
FIG. 16 shows graphs of corrected, measured frequencies divided by calculated frequencies versus pressure: (left) frequencies are corrected for the thermoacoustic boundary layer, (right) frequencies are corrected for the thermoacoustic boundary layer and center-of-mass motion according to Example 2.

FIG. 16 is a plot of the ratio $\Re(p, T)$ defined by equation 39 for the 4 lowest-frequency modes that illustrates the effect of the CM corrections in equations 28 and 29. For all the data, we first applied the correction $\Delta f_{calc}=g_{calc}$, which is always small: $g_{calc}/f_{meas} \leq 0.0006$. The data plotted in the left panel omit the CM corrections while the data plotted in the right panel include the CM terms: $\Delta f_{CM,1}+\Delta f_{CM,2}$, where the term CM,1 applies to the modes (1,0,0) and (3,0,0) and the term CM,2 applies to the (0,1,0) doublet. The right panel shows that the CM terms account for nearly all the pressure-dependence visible in the left panel.

FIG. 16 also displays the utility of averaging the two components of the (0,1,0) doublet. As p→0, the average of the two components (solid red line) extrapolates to $\Re$=1.00026, which is much closer to the theoretical value $\Re$=1 than the extrapolation of either component.

Figure 17:
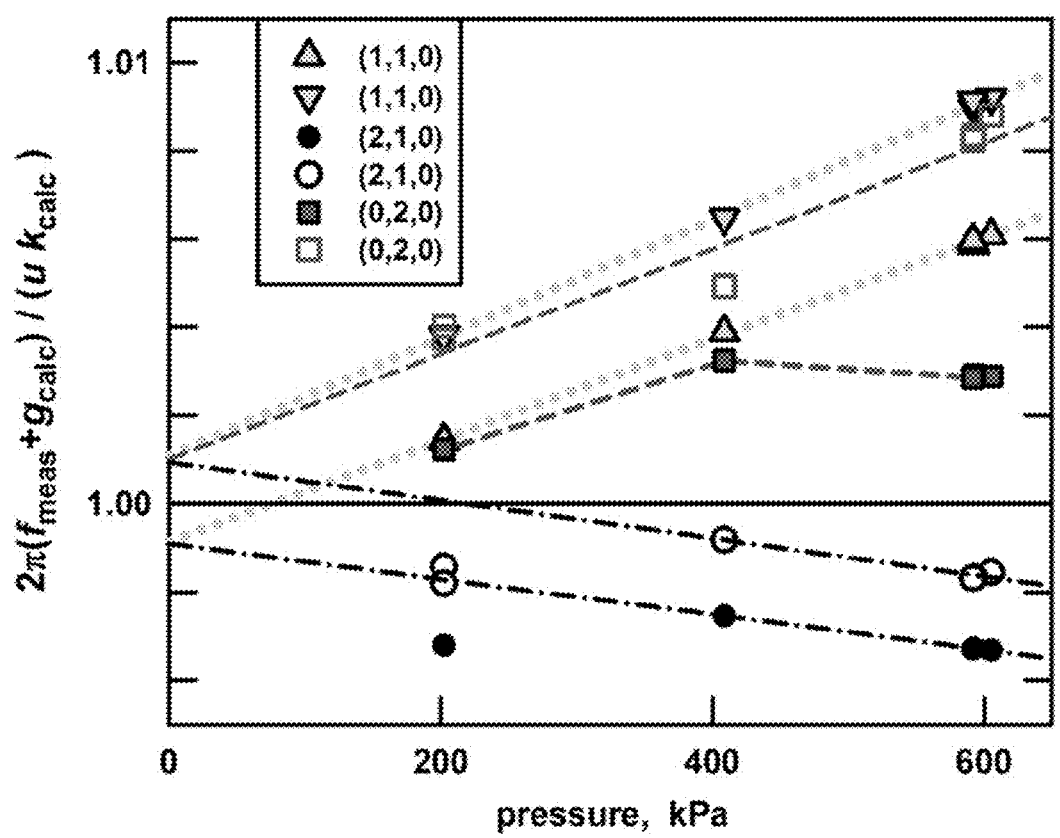
FIG. 17 shows an inconsistency between corrected, measured frequencies of various transverse and mixed acoustic modes due to gas-shell interactions as a function of pressure according to Example 2.

FIG. 17 displays typical difficulties encountered when trying to use the higher-frequency acoustic modes for gas metrology. The (1,1,0) doublet has the pressure dependence (df/dp)/p=0.012 MPa$^{-1}$. Therefore, this pressure-dependence could be calibrated if this mode was used to determine the speed of sound of a gas in a vessel with a percentage uncertainty much smaller than 1% at 600 kPa. If the vessel was too large to be thermostatted, calibration may be difficult.

Although the data for the (2,1,0) doublet in FIG. 17 could have had the smaller slope (df/dp)/p=−0.0042 MPa$^{-1}$, they exhibit a different problem at the low pressure 200 kPa. The average frequencies of the (2,1,0) doublet at 400 kPa and 600 kPa extrapolate to the calculated value $2\pi/(uk_{calc})$, as expected; however, the data at 200 kPa are inconsistent with the extrapolation. We speculate that the inconsistency is a consequence of the near crossing of the (2,1,0) mode with the shell mode at 445 Hz and p=0 kPa. (See FIG. 15.) Finally, the data for the lower-frequency component of the (0,2,0) doublet have a jog between 400 kPa and 600 kPa at 627 Hz. (The jog was present in two sets of data taken 3 hours apart.)

Figure 18:
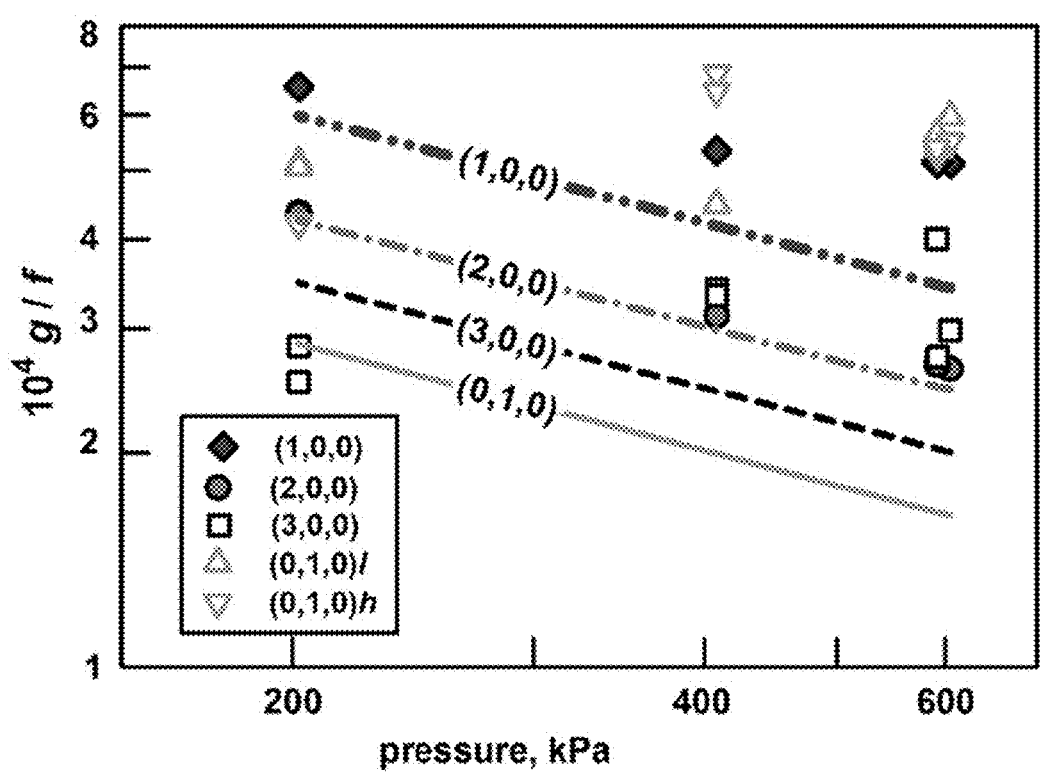
FIG. 18 shows a graph comparing the measured half-widths (symbols) and calculated half-widths (lines) versus pressure according to Example 2.

FIG. 18 compares the measured half-widths with the half-widths calculated using the cylinder model for the four lowest-frequency acoustic modes. For all the modes we studied, $g_{meas} \leq 7 \times 10^4 f_{meas}$. For the (3,0,0) mode at 200 kPa, $g_{meas}<g_{calc}$. We have no explanation for this anomalous result.

Summary of Isothermal Results.

Figure 19:
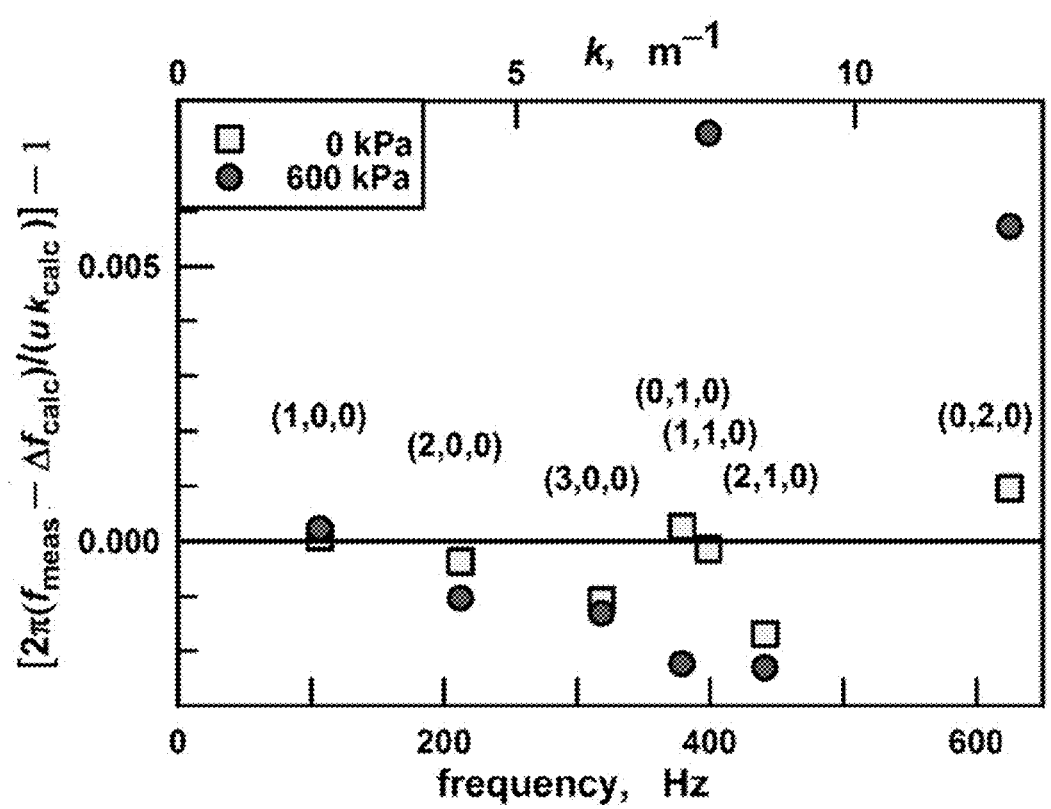
FIG. 19 shows a graph of fractional differences between the measured and calculated wavenumers for 7 modes at 600 kPa and extrapolated to zero pressure versus frequency according to Example 2.

For 7 low-frequency modes, FIG. 19 and Table 6 compare the ratio of calculated frequencies (or, equivalently, wavenumbers) to the measured, corrected frequencies at 600 kPa and when extrapolated to zero pressure. The plotted values were determined by averaging the frequencies of the measured doublets and then fitting the averaged frequencies of doublets (and of the singlets) with straight lines, such as those shown in FIG. 16 and FIG. 17. For the 4 lowest-frequency acoustic modes, the average of the zero-pressure values of $\langle k_{meas}/k_{calc}\rangle-1=(-0.00028\pm 0.00059)$, where the uncertainty is one standard deviation. On the scale of FIG. 19, the FE results for the spheroidal end-cap model and photo-based model are indistinguishable.

At 600 kPa, the acoustic results for the (1,1,0) and (0,2,0) modes differ by more than 0.5% from the models; therefore, these modes of the vessel are not suitable for gas metrology. It is plausible that the anomalous behavior of these modes results from the shell modes that occur at 339 Hz and 342 Hz under vacuum and extrapolate to higher frequencies as the pressure is raised. (See FIG. 15.)

The average for the 4 lowest-frequency acoustic modes in FIG. 19 is $\langle k_{meas}/k_{calc}\rangle-1=(-0.00110\pm 0.00102)$ at 600 kPa. This implies that these modes, or a subset of them, could be used to determine the speed of sound u in a gas inside the vessel with an uncertainty on the order of 0.1% by calibrating the vessel with microwaves alone. From equation 1, the gas's density (and mass) vary as $u^{-2}$, and their uncertainties will be at least twice the uncertainty of the speed of sound. Remarkably, the lowest-three acoustic modes have no unexplained pressure-dependence: $\langle k_{meas}/k_{calc}\rangle_{600\ kPa}/\langle k_{meas}/k_{calc}\rangle_{0\ kPa}-1=(0.00026\pm 0.00041)$. These modes are least subject to perturbations from shell resonances.

Weighing the Gas in the Vessel.

In this section, we simulate using the vessel as the "bucket" of a "bucket and stopwatch" gas flow standard. Using only microwave calibration data and then {microwave+acoustic} calibration data, we determine the mass of argon in the vessel. We consider the effects of temperature gradients and the uncertainty of the collected mass.

Weighing the Collected Gas—No Temperature Gradient.

The vessel was evacuated before the calibration began. To begin a calibration, the operator establishes a steady gas flow through the meter under test into a pipe that bypasses the collection vessel. After a steady flow is established, a timer ("stopwatch") is started and, simultaneously, valves are actuated to redirect the flow from the bypass into the collection vessel. These operations define the start of the calibration interval $\Delta t$. At the end of the interval $\Delta t$, the timer is stopped and the valves are actuated to direct the flow back into the bypass pipe. After a much longer interval that allows the collected gas to come into a steady state, the mass M of the collected gas is determined from pressure and temperature measurements and a prior calibration of the vessel's volume. Finally, the mass flow rate $Q=M/\Delta t$ is computed.

Our simulation assumed that (1) the mass of the vessel is known, (2) the microwave measurements and model have been completed, (3) after the collection is completed, the acoustic resonance frequencies and the pressure are measured, (4) the thermophysical properties of argon are accurately known, and (5), in this case, the collected gas was at a pressure of 0.6 MPa. In the simulation, we did not attempt to correct for the unmodeled pressure-dependence of the resonance frequencies that we observed under nearly isothermal conditions. However, guided by our observation that shell modes and the gas modes interact, we used only the lowest-frequency acoustic modes.

Figure 12:
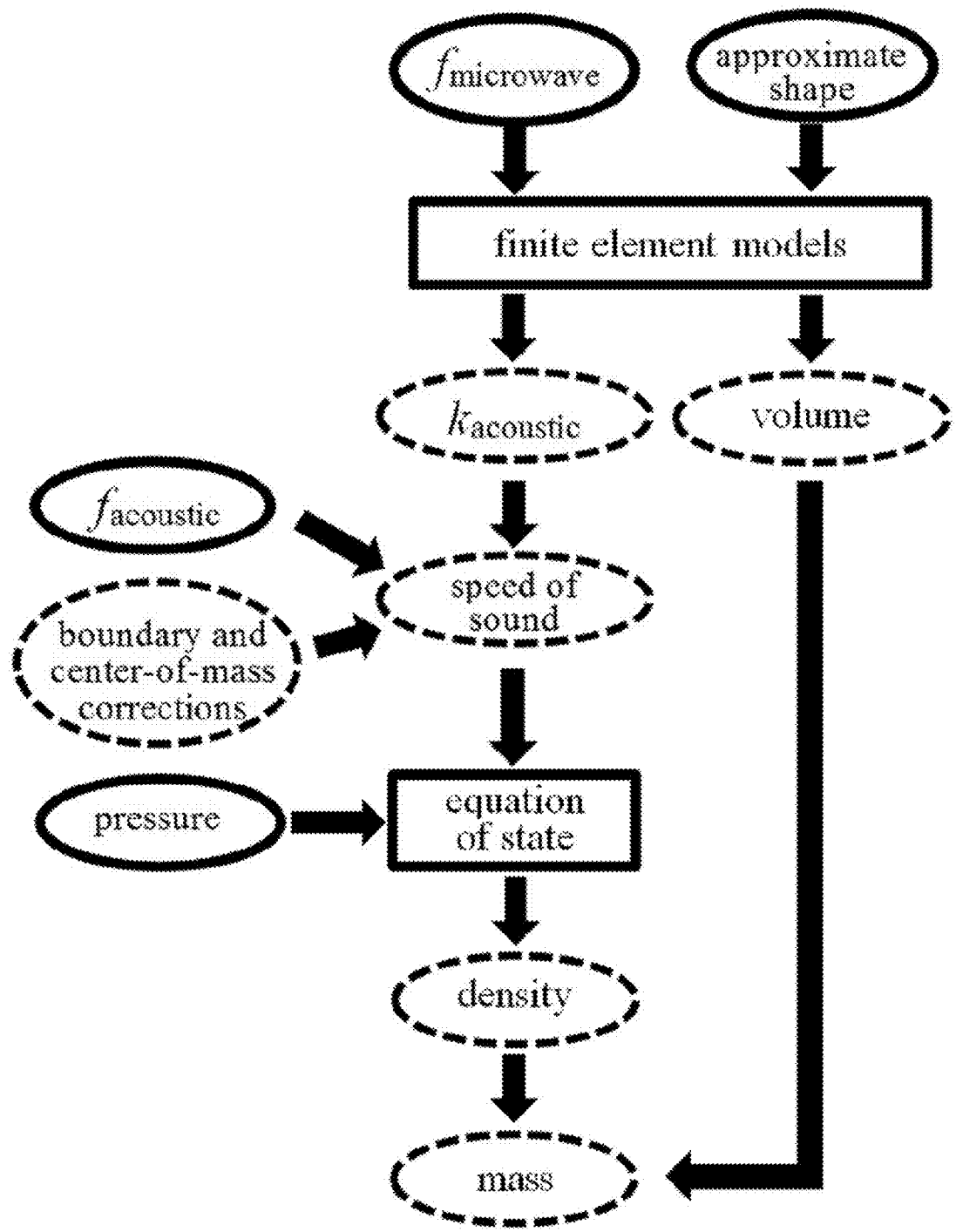
FIG. 12 shows a flowchart for determining a mass of a gas disposed in a vessel according to Example 2.
Figure 20:
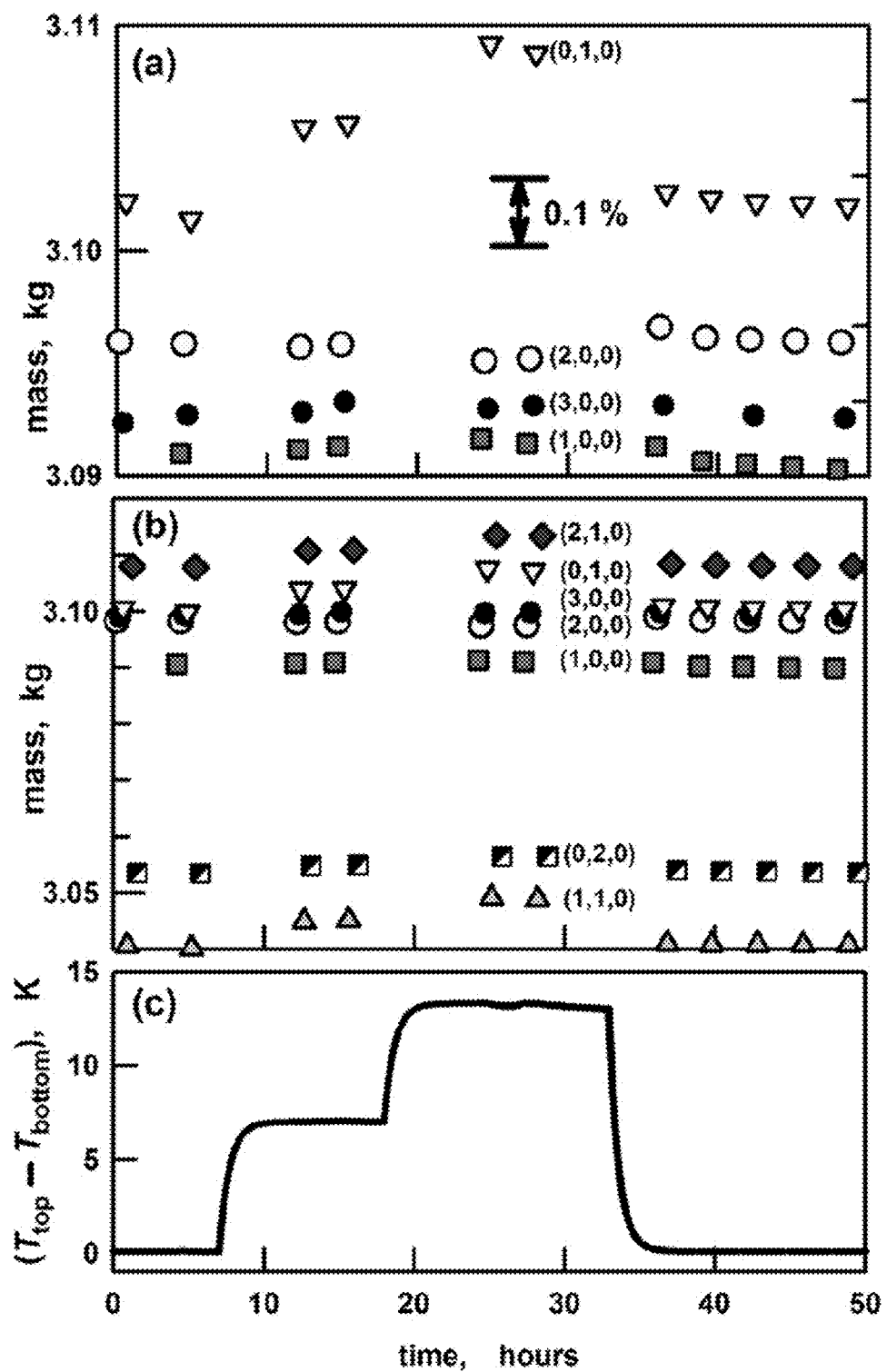
FIG. 20 shows a graphs of mass versus time and a graph of temperature gradient versus time according to Example 2.

The center panel of FIG. 20 displays the mass M of argon in the vessel deduced from the pressure and from frequencies of the various acoustic modes, as outlined in FIG. 12. The calculations used the thermophysical property data for argon. In the absence of a temperature gradient, the mean and standard deviation of the density for the 4 lowest-frequency acoustic modes was: $\langle\langle\rho\rangle\rangle_{4modes}=10.478\times(1\pm0.0014)$ kg/m$^3$. Using the volume determined from the microwave measurements, we found the mass of argon in the vessel $M=\langle\langle\rho\rangle\rangle_{4modes} V_{vessel}=3.0979\times(1\pm0.0016)$ kg, where the uncertainty includes all the terms in Table 8.

In FIG. 20, the upper-most panel displays the same data as the middle panel of FIG. 20; however, the analysis used the wavenumbers that we deduced from the isothermal acoustic measurements instead of the wavenumbers calculated from the microwave measurements. If this kind of calibration (using an isothermal reference gas, such as argon) were available and if only the lowest three acoustic modes were used, the fractional standard deviation of M for the test gas would be reduced from 0.0016 to 0.0007, even if the measurements were made with a temperature gradient.

Effects of a Temperature Gradient.

Within a few minutes after the collection stops, bouyancy-driven convection stratifies the gas in the collection vessel so that the warmer gas is near the top of the vessel and cooler gas is near the bottom of the vessel. Subsequent temperature changes can take hours.

As shown in the photograph (FIG. 11) and schematically in FIG. 13, the top quarter of the vessel was covered with an insulating blanket. Beneath the blanket, we had taped a heater to the top of the vessel and a thermistor that was used to estimate the temperature $T_{top}$. A second thermistor taped to the bottom of the vessel estimated $T_{bottom}$. FIG. 20 (bottom panel) displays the time-dependence of the temperature difference $\Delta T=(T_{top}-T_{bottom})$. During hours 7 to 17 we applied 120 W to the heater. This generated an approximately-vertical, non-uniform, temperature gradient in the vessel such that $T_{top}=30.8°$ C., $T_{bottom}=23.8°$ C., and the average temperature acoustic temperature $\langle T_{acoust}\rangle=26.5°$ C. During hours 17 and 30, we applied 240 W to the heater and generated a nearly-steady-state with $T_{top}=39.7°$ C., $T_{bottom}=26.4°$ C., and $\langle T_{acoust}\rangle=31.8°$ C. The maximum measured temperature difference was, fractionally, $\Delta T/T\approx 0.043$; however, there could have been larger temperature differences between locations on the vessel that were not detected by the two thermometers. During the 50 h spanned by FIG. 20, the temperature of the laboratory varied by approximately $\pm 0.5$ K.

Table 7 compares the measured frequency changes caused by the heater with the changes predicted by the cylinder model using first-order perturbation theory. Independent of any model, it is remarkable that a temperature gradient on the order of $\Delta T/T\approx 0.043$ which changes the speed of sound in argon by $\Delta u/(u)\approx 0.043/2$ generated a resonance frequency change $|\Delta f/f|\le 0.00126$ in the worst case. For the non-degenerate longitudinal modes, (1,0,0), (2,0,0), and (3,0,0), the measured frequency changes were compartively small and noisy:$10^4|\Delta f/f|\le 2.4$. Thus, these changes are on the order of $(\Delta T/T)^2$. For the averaged doublets, the frequency changes were as large as $10^4|\Delta f/f|\le 12.6$ and consistent with a linear dependence on the temperature difference. A $1^{st}$ order model predicts $\Delta f/f=0$ for the non-degenrate modes and for the averaged doublets. The $2^{nd}$ order model also predicts $\Delta f/f=0$ for the non-degenerate modes and $\Delta f/f\propto (\Delta T)^2$ with very small coefficients of proportionality for the doublets. The inconsistency between the measurements and the model led us to examine the effect of the temperature gradient on the shape of the cavity, as estimated from the microwave frequencies and from a FE model of a long cylinder.

Figure 21:
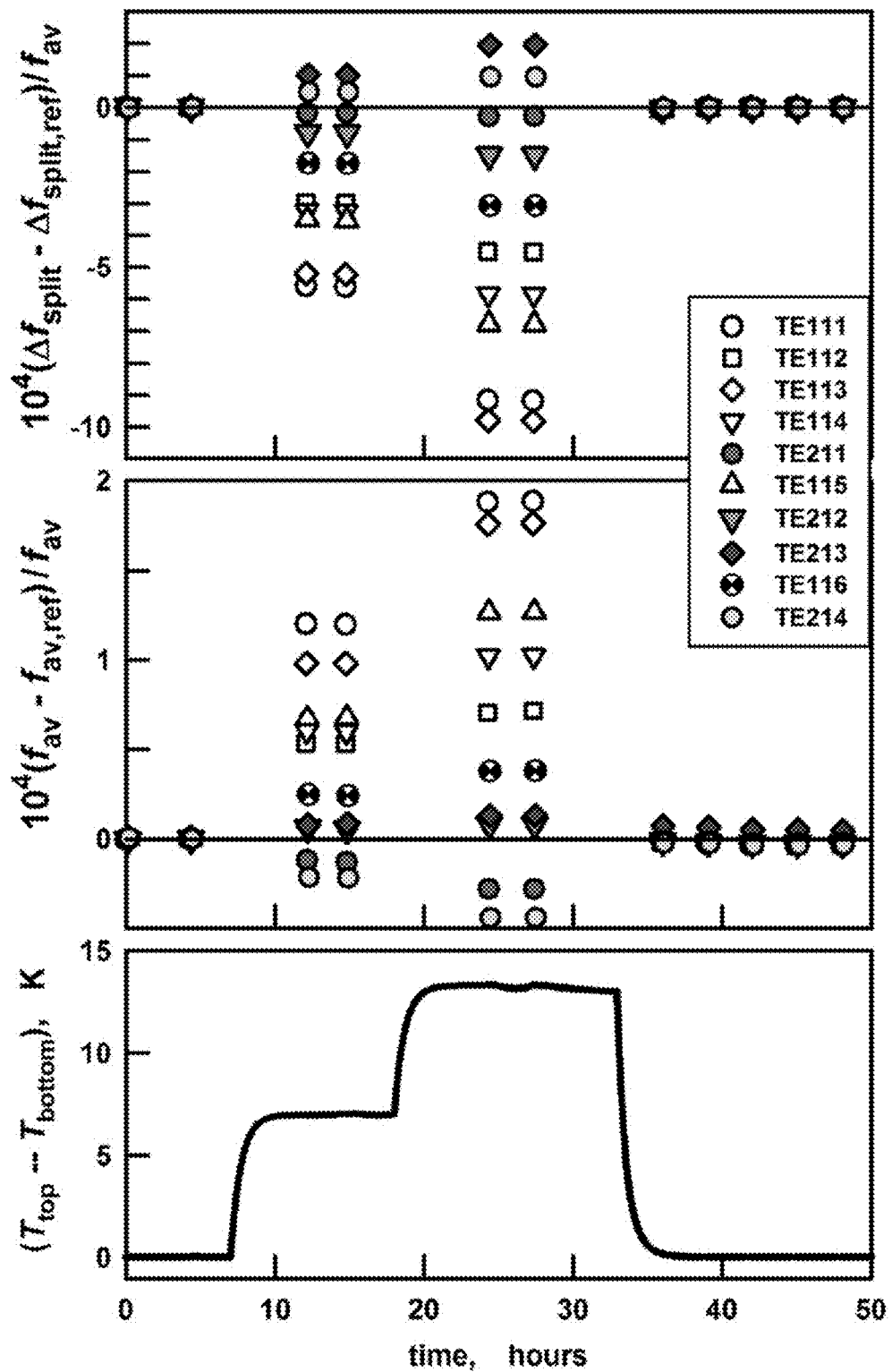
FIG. 21 shows a graph of a change in splitting of doublets versus time, a graph of fractional frequency change first time, and a graph of temperature difference versus time according to Example 2.

For 10 microwave doublets, FIG. 21 displays the changes of the average frequencies and the frequency splittings from reference values when the temperature gradient was imposed. The reference values were measured during the interval from 3 h to 4 h, while the temperature of the vessel was $T_{ref}=21.2°$ C. and the heater power was zero. Before plotting, the averaged frequencies $f_{av}$ were reduced by $\alpha_T[(T_{top}+T_{bottom})/2-T_{ref}]$ to account for the linear coefficient of thermal expansion of the vessel. The data for the averaged doublets (middle panel of FIG. 21) have the mean value and standard deviation $\langle(f_{av}-f_{av,ref})/f_{av}\rangle=2.6\times 10^{-5}$ and $\sigma[(f_{av}-f_{av,ref})/f_{av}]=8.1\times 10^{-5}$, when $\Delta T=(T_{top}-T_{bottom})=13$ K. They are consistent with the linear relation $(f_{av}-f_{av,ref})/f_{av}\propto\Delta T$ with coefficients of proportionality ranging from $-3.3\times 10^{-6}$ K$^{-1}$ to $1.5\times 10^{-5}$ K$^{-1}$. The data for the splitting of the doublets (top panel of FIG. 21) are also consistent with the linear relation $(f_{split}-f_{split,ref})/f_{av}\propto\Delta T$ with much larger coefficients of proportionality ranging from $-7.4\times 10^{-5}$ K$^{-1}$ to $1.5\times 10^{-5}$ K$^{-1}$. We now argue that these data cannot be explained by redistribution of the argon caused by temperature gradients.

During the measurements shown in FIG. 21, the refractive index of the argon was $n\approx 1+3A_\in\rho\approx 1.00163$, where $A_\in=4.142$ cm$^3$ mol$^{-1}$ is the dielectric polarizability of argon. The largest temperature difference, $\Delta T/T\approx 0.043$, redistributed the argon within the vessel and changed the refractive index locally by, at most, $\Delta n\approx(n-1)\Delta\rho/\rho\approx(n-1)(-\Delta T/T)\approx -7\times 10^{-5}$. The microwave frequencies, similar to the acoustic frequencies discussed in Section 3.3, depend upon volume averages of the density; therefore, we expected the frequency changes $(\Delta f/f)_{micro}$ to be much less than $7\times 10^{-5}$. Furthermore, the temperature-gradient-driven changes of $(\Delta f/f)_{micro}$ for the averaged doublets are expected to vary as $(\Delta T/T)^2$, not as $(\Delta T/T)$.

We used a FlexPDE script for thermoelasticity problems to estimate the effects of a uniform, vertical temperature gradient on a long, horizontal, cylindrical shell with unconstrained boundaries and with the properties: inner radius 0.25 m, thickness 3.9 mm, Young's modulus 197 GPa, Poisson ratio 0.297, and linear coefficient of thermal expansion $12\times 10^{-6}$K$^{-1}$. As a measure of the effect of a temperature difference $\Delta T=T_{top}-T_{bottom}$, we used the ratio $l_v/l_h$, where $l_v$ and $l_h$ are the lengths of the semi-major vertical and horizontal axes of the cylinder's cross-section. This FE model predicts $l_v/l_h = 1 + 6.1 \times 10^{-6} (\Delta T/K)$. For $\Delta T = 13$ K, $l_v/l_h = 1.000079$, which is on the order of the values of $(\Delta f/f)_{microwave}$ in FIG. 21. This order-of-magnitude agreement supports the idea that the imposed temperature gradient changes the shape of the vessel and the shape change leads to the linear relation $(\Delta f/f)_{microwave} \propto (\Delta T/T)$.

Uncertainties.

Table 8 summarizes the contributions to the uncertainty of the present determination of the mass of argon in the vessel in the presence of a temperature gradient.

TABLE 8

| Phenomenon | Value |
|---|---|
| Volume of empty vessel | 0.0006 |
| Volume increase between 0 MPa and 0.6 MPa | 0.0002 |
| Inconsistent acoustic modes at 0.6 MPa | 0.0015 |
| Speed of sound in argon at 0.6 MPa | 0.00014 |
| Pressure | 0.0001 |
| Unmodeled shape change at $(T_{top} - T_{bottom}) = 13$ K | 0.00008 |
| Root Sum of Squares | 0.0016 |

We do not have a model for shape changes induced by temperature gradients; therefore, such changes contribute to the uncertainty of the mass measurement. We estimate this contribution by using equation 1 and neglecting the real-gas corrections: $M \propto V_{tank}/u^2 \propto f_{micro}^3/f_{acoust}^2$. On the average, the unmodeled shape change affects the acoustic and microwave frequencies (or, equivalently, wavenumbers) by the same fraction; therefore, we use the standard deviation $\sigma[(\Delta f/f)_{micro}] = 8.1 \times 10^5$ when $(T_{top} - T_{bottom}) = 13$ K as a measure of this uncertainty contribution.

As the pressure inside the vessel was increased, the expansion of $V_{vessel}$ was not isotropic; however, we did not develop a quantitative model for the expansion. Instead, we argued that the pressure expansion was greater than that of a thin-walled spherical shell and less than that of a long, thin-walled, cylindrical shell to arrive at the lower and upper bounds: $3.5 \times 10^{-4}$ MPa$^{-1}$ < $(\partial V/\partial p)_T/V$ < $6.2 \times 10^{-4}$ MPa$^{-1}$. For a pressure change of 0.6 MPa, the difference between these two bounds is $2 \times 10^{-4}$, which we take as the fractional uncertainty of $V_{vessel}$ upon increasing the internal pressure.

We obtained the thermodynamic data for argon from the Helmholtz energy surface. The surface produced accurate speed-of-sound data with a fractional uncertainty $u_r(u) = 7 \times 10^{-5}$ or less, over a wide range of conditions including those encountered here. The mass of argon in the vessel is calculated from $u^2$; therefore, we estimate the thermodynamic contribution to $u_r(M)$ as $2 \times u_r(u) = 1.4 \times 10^{-4}$. This uncertainty could be reduced if the argon data were re-analyzed using the density and acoustic virial coefficients deduced from ab initio theory.

During the present measurements, we used two pressure gauges. Based on the manufacturer's specifications and our experience with these gauges, we estimated $u_r(p) = 0.0001$ near 0.6 MPa.

Discussion of a Large Flow Standard.

We simulated a "bucket and stopwatch" flow calibration using a collection vessel with a volume that was determined (while evacuated) from measurements of the frequencies of its microwave resonances. We determined the mass of argon in the vessel by measuring the pressure and the frequencies of the acoustic resonances in the argon. The relative uncertainty of the collected mass was $u_r(M) = 0.0016$, where the uncertainty was dominated by inconsistent results from the three lowest-frequency acoustic modes. The value of the collected mass, determined acoustically, was only weakly sensitive to temperature gradients imposed on the collection vessel. We now discuss strategies for reducing the uncertainty, problems that might arise upon increasing $V_{vessel}$ by a factor of 10 to 100, and problems that might arise when using the collection vessel as part of a dynamic flow standard: that is, a standard that measures the collected mass while gas is flowing into the vessel.

Inconsistencies among the acoustic wavenumbers might have resulted from the effects of unmodeled shell resonances that were detected during the vacuum measurements in FIG. 14. We determined experimental values of the acoustic wavenumbers by assuming, for each mode, the values of $(f_{meas} + g_{calc})_{lmn}$ are linear functions of the pressure and we extrapolated these values to zero pressure. This procedure has worked remarkably well for thick shells when the frequencies of the shell resonances are nearly constant over the relevant pressure range. However, the resonance frequencies of thin-walled shells are stronger functions of pressure; therefore, the assumption of linearity is questionable. More accurate wavenumbers might be obtained by using a better model for extrapolating to zero pressure and/or by using a thicker shell. In this context, a spherical shell is advantageous because it is approximately twice as stiff as a cylindrical shell with the same thickness-to-radius ratio.

If the volume of the collection vessel were increased by a factor of 10 to 100, the cost of a well-characterized test gas, such as pure argon, might be significant. If less-well-characterized test gases were used, (for example, a natural gas with, possibly, varying composition), it is contemplated that measurement include the speed of sound of the test gas using a small, auxiliary, thermostatted acoustic resonator under conditions encountered in the flow standard. If the auxiliary resonator were a suitably-designed Helmholtz resonator, it could operate in the same frequency range as the collection vessel.

To achieve similar signal-to-noise ratios using the lower-frequency modes of a 10× to 100× larger volume vessel, the microwave power and acoustic power would have to be increased by factors of approximately 10× to 100×. (Here, we neglect the size-dependence of the Qs.) Fortunately, the accuracy of the present mass determination was not limited by the signal-to-noise ratio of either the microwave or acoustic measurements; therefore, sufficient accuracy may be obtained from larger vessels without scaling the power.

While we conducted our acoustic measurements, all of the vessel's ports were closed. It might be desirable to conduct "dynamic" calibrations, that is, calibrations conducted while gas flowed through a duct, either into or out of the collection vessel. In the absence of flow, such ducts would have only small effects on the acoustic resonance frequencies of modes that had pressure nodes where the ducts connected to the vessel. However, the effects of flow on the resonance frequencies should be a subject for future research.

Dynamic calibrations can include the time to accurately measure an acoustic resonance frequency. When a sound generator operating at a frequency near a cavity resonance $f_N$ is turned on at the time t=0, the acoustic pressure approaches a steady-state value as $\exp(-2\pi g_N t)$, where $g_N$ is the half-width of the resonance. If we apply the conservative criterion, $\exp(-2\pi g_N t) < 10^{-4}$, $g_{(1,0,0)} \approx g_{(2,0,0)} \approx 0.06$ Hz, a wait of t=24 s is required before each amplitude measurement. In this work, we used a very conservative protocol that determined $f_N$ and $g_N$ by fitting 22 amplitudes. The amplitudes were measured at 11 frequencies starting at $f_N - g_N$ and ending at $f_N+g_N$ with steps of $g_N/5$. Then, the frequency sweep was reversed, starting at $f_N+g_N$ and ending at $f_N-g_N$ with steps of $-g_N/5$. This protocol includes 528 s for a mode such as (1,0,0) with $g_{1,0,0}=0.06$ Hz. Other protocols can be devised; however, the characteristic time $(2\pi g_N)^{-1}$ is included in a resonance method.

Example 3

Detecting a Leak in a Gas-Filled Vessel Using an Acoustic Resonance

In this example, we describe a leak from a large, unthermostatted vessel into ambient air was detected an order of magnitude more effectively by measuring the time dependence of the ratio $p/f^2$ than by measuring the ratio $p/T$. Here f is the resonance frequency of an acoustic mode of the gas inside the vessel; p is the pressure of the gas, and T is the kelvin temperature measured at one point in the gas. In general, the resonance frequencies are determined by a mode-dependent, weighted average of the square of the speed-of-sound throughout the volume of the gas. However, the weighting usually has a weak dependence on likely temperature gradients in the gas inside a large vessel. Using the ratio $p/f^2$, we measured a gas leak $(dM/dt)/M \approx -1.3 \times 10^{-5}$ $h^{-1} = 0.11$ year$^{-1}$ from a 300-liter vessel filled with argon at 450 kPa that was exposed to sunshine-driven temperature and pressure fluctuations as large as $(dT/dt)T \approx (dp/dt)/p \approx 5 \times 10^{-2}$ h$^{-1}$ using a 24-hour data record. This leak could not be detected in a 72-hour record of $p/T$. (Here M is the mass of the gas in the vessel and t is time.)

In a gas, the speed of sound u is a function of temperature. The time for a free-traveling sound wave to propagate a distance is determined by an average temperature of the gas along the traveled path. Likewise, the frequency of an acoustic resonance in a closed cavity is determined by a mode-dependent average of temperature over the volume of the cavity. Conversely, the average temperature of a gas in a cavity can be deduced from measurements of the frequencies of gas resonances.

In prior examples herein, we showed that the mass M of gas within a vessel was provided from measurements of the gas pressure and the frequencies of the microwave and acoustic resonances within the vessel. The microwave frequencies were determined by the shape and volume of the vessel. The acoustic measurements were performed in an absence of multiple thermometers to obtain an average temperature with sufficient accuracy for flow metrology. Acoustic measurements were advantageous when it was impractical to install many calibrated thermometers throughout a large, gas-filled volume. Using this technique, we also showed that the apparent value of M did not change when we imposed a time-independent temperature gradient such that the gas in a vessel was heated on the top and cooled on the bottom. The time-independent temperature gradient simulated the gradient that resulted from a gas flowing through a meter being calibrated and then into a large collection vessel. During this earlier work, the vessel's temperature was well-controlled. We noticed that the gas pressure decreased slowly, and we attributed the decrease to a leak from the vessel into the ambient air. The leak was unavoidable; therefore, the data were corrected to account for the leak. In this example, we show that the leak was detected easily, even in the presence of large temperature fluctuations, by measuring the decrease of the ratio $p/f^2$ with time. Here f is the resonance frequency of an acoustic mode of the gas inside the vessel; p is the pressure of the gas, and T is the kelvin temperature measured at one point in the gas. To first order, the resonance frequencies are determined by a mode-dependent, weighted average of the square of the speed-of-sound u throughout the volume of the gas, i.e. $f^2 \propto \langle u^2 \rangle$, where $$\langle u^2 \rangle = \frac{\int_V u^2 |\varphi|^2 dV}{\int_V |\varphi|^2 dV}. \tag{40}$$

The acoustic velocity potential $\varphi$ is proportional to the local acoustic pressure in the standing wave when the temperature is uniform. Regions where $\varphi=0$, i.e. pressure nodes, do not contribute to the weighted average. The weighted average in Eq. 40 has a weak dependence on temperature gradients that are likely to form in the gas inside a large vessel.

We placed the 0.3 m$^3$ gas-filled (argon at 0.45 MPa) vessel as used in Example 2 in direct sunlight that generated time-dependent temperature and pressure variations in the gas as large as $(dT/dt)/T \approx (dp/dt)/p \approx 5 \times 10^{-2}$ h$^{-1}$. (Here, "t" denotes time and T is the kelvin temperature measured at one location in the gas.) The sunlight-driven variations obscured a gas leak of $(dM/dt)/M \approx -1.3 \times 10^{-5}$ h$^{-1}$ out of the vessel into ambient air, even when the pressure data were averaged over 3 days. However, the leak rate was deduced with an uncertainty of about ±30% from measurements of $p/f^2$ averaged over just 1 day, where f is the resonance frequency of a single acoustic mode. (Throughout this paper, we report the statistical, standard uncertainty corresponding to a 68% confidence level.) Thus, measurements of the pressure and a resonance frequency can efficiently detect a leak from large, unthermostatted volumes, such as an air lock, or a vessel designed to contain a hazardous process gas, or a vessel used to store liquids or gases outdoors, or a large subterranean cavern with distinct resonances.

Acoustic Resonances and the Mass of Gas in an Isothermal Cavity.

The ratio $p/f^2$ was proportional to the mass M of the gas in a vessel when temperature of the gas is uniform. Therefore, a leak that generates negative values of $dM/dt$ can be detected by measuring a decrease of $p/f^2$ with time.

The molar density $\rho_m$ of the gas in a vessel is related to the pressure p and the speed of sound u in the gas by combining the virial equation of state $$p = \rho_m RT(1 + B\rho_m + \dots) \tag{41}$$

with the analogous equation for the square of the speed of sound $$u^2 = \frac{\gamma_0 RT}{M_m}\left(1 + \frac{\beta_a p}{RT} + \dots\right). \tag{42}$$

We then obtain an expression for the mass $M = \rho_m M_m V_{vessel}$ of the gas in the vessel $$M = \frac{\gamma_0 p V_{tank}}{u^2}\left[1 + (\beta_a - B)\frac{p}{RT} + \dots\right], \tag{43}$$

In Eqs. 41, 42, and 43, $M_m$ is the average molar mass of the gas; $V_{vessel}$ is the volume of the vessel; R is the universal gas constant; $\gamma_0 = C_p/C_V$ is the gas's zero-pressure heat-capacity ratio; and, $\beta_a$ and B are the gas's acoustic and the density second virial coefficients, respectively.

The speed of sound u in the gas inside the vessel is well-approximated by $u=f_N L_N$ where $f_N$ is the resonance frequency of the acoustic mode of the gas identified by the subscript N, and $L_N$ is a characteristic length that depends upon the mode N. For cavities with special geometries (e.g. right circular cylinder, sphere, and the like), $L_N$ can be calculated analytically. For vessels with complicated shapes (such as the vessel in FIG. 22), $L_N$ can be accurately calculated using numerical methods, provided that the shape of the vessel is known or is fitted to microwave resonance frequency measurements. For a vessel that does not contain obstructions and has rigid, non-porous walls, the fractional corrections to $u=f_N L_N$ are on the order of $g_N/f_N$, where $g_N$ is the half-width of the acoustic resonance with frequency $f_N$. Throughout the range of the present measurements, $g_N/f_N 3\times 10^{-4}$ and changes in $g_N/f_N$ are less than $10^{-5}$; therefore, we ignored corrections resulting from $g_N/f_N$. We also ignored the small change of $V_{vessel}$ that occurred when the pressure varied by approximately 8% in the range 427 kPa<p<463 kPa.

We were concerned with detecting small changes in M resulting from a leak; therefore, accurate values of $L_N$ and $V_{vessel}$ are unnecessary. However, our sensitivity to detect small leaks in the presence of large temperature changes is improved by approximately a factor of two if we account for the thermal expansion of $L_N$ and $V_{vessel}$ by using the expressions $L_N = L_{N,0}[1+\alpha_T(T_{vessel}-T_0)]$ and $V_{vessel}=V_{vessel,0}[1+3\alpha_T(T_{vessel}-T_0)]$. Here $T_{vessel}$ is the average temperature indicated by two thermistors attached to the top and bottom of vessel; $T_0$ is an arbitrary reference temperature and $\alpha_T$ is the coefficient of linear thermal expansion of the metal comprising the vessel. (For $T_0$ we used the first value of T in a series of measurements and we used $\alpha_T=11.7\times 10^{-6}$ K$^{-1}$.) Substituting $u=f_N L_N$ and the above expressions for $L_N$ and $V_{vessel}$ into Eq. 43, the thermal expansion correction is $[1+3\alpha_T(T_{vessel}-T_0)]/[1+\alpha_T(T_{vessel}-T_0)]^2 \approx 1+\alpha_T(T_{vessel}-T_0)$, to first order, assuming the expansion is isotropic. The small term $(\beta_a-B)p/(RT)$ in Eq. 43 contains the difficult-to-measure average gas temperature T. It is convenient to eliminate T by using the approximation $T/T_1 \approx (f_N/f_{N,1})^2$, where $f_{N,1}$ is the acoustic resonance frequency at the temperature $T_1$. During the night, there were no heat sources (e.g. sunlight) on our vessel; therefore, the average temperature of the vessel's wall and the average temperature of the gas approached a common value: $T_{vessel} \approx T \equiv T_1$. This expectation is consistent with the near agreement (±0.4 K) between temperature sensors that we had taped to points on of the top and bottom surfaces of the vessel. Therefore, at night the small correction term $(\beta_a-B)p/(RT)$ can be accurately evaluated using frequency measurements as a surrogate for the gas temperature.

After accounting for the thermal expansion and for measuring a frequency instead of measuring the speed of sound, Eq. 43 becomes:

$$M_{p/f^2,c} = \frac{\gamma_0 V_{tank,0}}{L_{N,0}^2} \frac{p}{f_N^2}\left[1 + \alpha_T(T_{tank}-T_0) + (\beta_a-B)\frac{p}{RT_1}\frac{f_{N,1}^2}{f_N^2}\right], \quad (44)$$

wherein we neglected higher-order terms and introduced the subscript "p/f$^2$, c" to emphasize that this calculation of M depends upon frequency measurements and includes the correction terms in square brackets.

For many common gases including dry air, accurate values of the temperature-dependent quantities $\gamma_0$, $\beta_a$ and B are available in publically accessible databases. The gas temperature ranged from 20° C. to 45° C.; a typical pressure was 450 kPa; and, the test gas was argon for which $\gamma_0=5/3$. Under these limited conditions, the virial coefficient term in square brackets in Eq. 44 changes by only ¼ as much as the changes in the thermal expansion term. Specifically, when the temperature increases from 20° C. to 45° C., the term $(\beta_a-B)p/(RT)$ increases by 0.000068 (from 0.004707 to 0.004775). In the same range, $\alpha_T(T-T_0)$ increases by 0.00029. If we had used dry air instead of argon, the change in the virial coefficient term in Eq. 44 would be 78% of the change in the thermal expansion term.

Conventionally, leaks from large vessels are detected without measuring acoustic resonance frequencies. For example, one could monitor the gas pressure to detect a leak. This approach is greatly improved by monitoring the ratio p/T, where T is the temperature of the gas measured at some point inside the vessel. Similar to the acoustic method, monitoring the pressure can be refined by accounting for the thermal expansion of $V_{vessel}$ and accounting for the virial corrections to the ideal gas law. With these refinements, an expression for the mass of gas in a vessel as a function of the measured temperature and pressure is:

$$M_{p/T,c} = \frac{V_{tank,0} M_m}{R} \frac{p}{T}\left[1 + 3\alpha_T(T_{tank}-T_0) - B\frac{p}{RT} + \ldots\right], \quad (45)$$

where the symbol $M_{p/T,c}$ emphasizes that this calculation of the mass of gas in the vessel depends upon the ratio p/T and includes corrections to the same order as Eq. 44. The complexity of Eq. 45 is comparable to that of Eq. 44. However, at each level of complexity, $M_{p/f_2,c}$ computed by Eq. 44 leads to more sensitive leak detection than $M_{p/T,c}$ computed from Eq. 45.

Resonance Frequencies were Insensitive to Linear Temperature Gradient.

Figure 23:
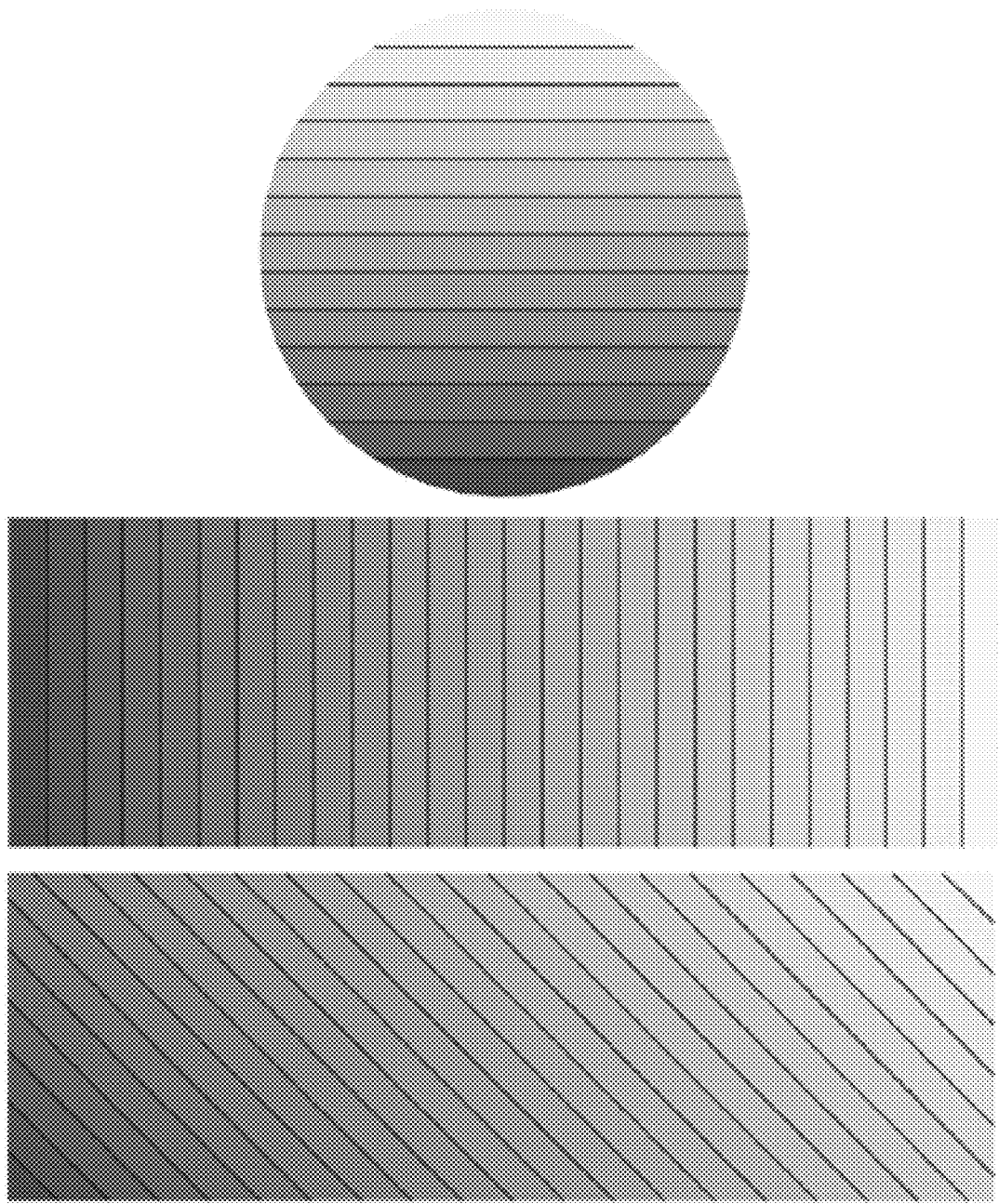
FIG. 23 shows temperature gradients in a cylindrical vessel according to Example 3.

We expected that measurements of p/f$^2$ would be useful because of the remarkable prediction that a linear temperature gradient (such as the gradients illustrated in FIG. 23) will change the resonance frequencies $f_N$ by a fraction proportional to the square of the gradient, provided that the gradient is not too large. In this work, we detected sun-generated, vertical temperature differences as large as $\Delta T \equiv (T_{top}-T_{bottom})=15$ K near the average temperature $T_{ave}=300$ K. If this measured temperature difference occurred when the temperature was a time-independent, linear function of depth in the vessel, the predicted frequency shifts are $\Delta f_N/f_N \propto [\Delta T/(2T_{ave})]^2 \approx 6\times 10^{-4}$. Because the measured values of $\Delta f_N/f_N$ were smaller than $6\times 10^{-4}$, we speculate that $\Delta T<15$ K inside most of the vessel.

The effects of a temperature gradient on the acoustic resonance frequencies of a model "vessel" that was a right circular cylindrical cavity (with inner radius a, length L, and interior volume V) oriented with its symmetry axis horizontal can be modelled as filled with a compressible, thermally conducting fluid that supported sound waves but was otherwise stationary (i.e. no convection). The cylindrical shell was mechanically rigid, and its position was fixed in space. The shell was not isothermal; its temperature $T_w(a,\theta,z)$ was a specified function of position. (The z-axis is oriented horizontally along the cylinder's symmetry axis.) The steady-state temperature T(r) of the gas in the cavity was expressed as $T(r)=T_0[1+\tau_0 \Im(r)]$, where $T_0$ is the average gas temperature over the cavity volume; $\tilde{\tau}_0$ is a dimensionless scale factor much smaller than 1; and the profile function $\Im(r)$ is determined from the Laplace equation $\nabla^2 \Im = 0$, subject to the Dirichlet boundary condition $\tilde{\tau}_0 \Im (a, \theta, z) = [T_w(a, \theta, z) - T_0]/T_0$ at the wall. They used first-order perturbation theory to solve the Helmholtz equation with a spatially varying speed of sound $u^2 = u_0^2 [1 + \tilde{\tau}_0 \Im(r)]$ and compared the resonance frequencies of the gas with and without the small perturbation $\tilde{\tau}_0 \Im(r)$. For a gas-filled cylindrical cavity containing no heat sources or sinks, they concluded that if $\Im(r)$ is a linear function of distance, then the acoustic resonance frequency for any mode depends upon $\tilde{\tau}_0^2$, but not upon $\tilde{\tau}_0$ provided that $\Im(r)$ is a solution to the Laplace equation and $\langle \Im \rangle = 0$. This result is intuitive because a standing wave in the cavity may be decomposed into counter-propagating traveling waves, whose round-trip travel times through a linear temperature gradient will be the same and unchanged from the uniform case to first order.

Description of the Vessel.

Figure 22:
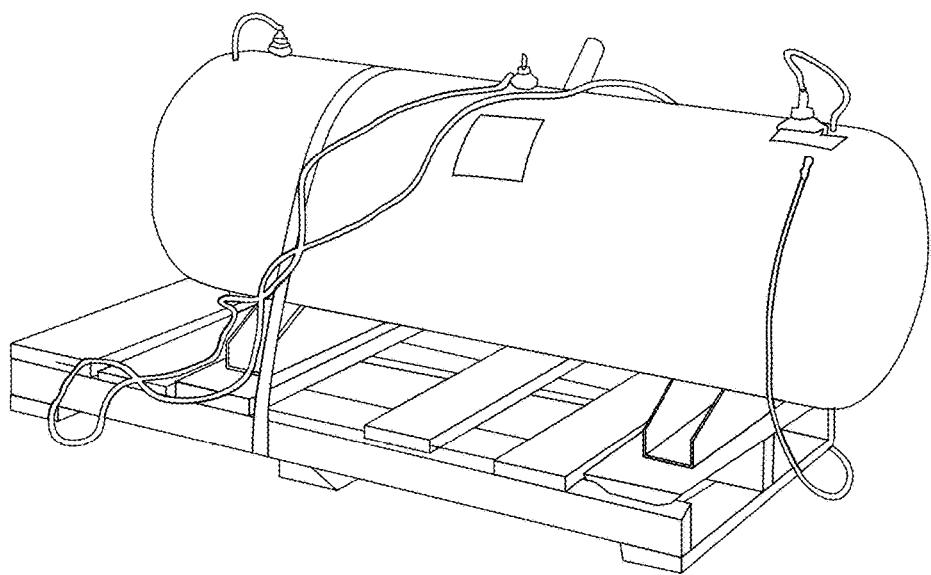
FIG. 22 shows a photograph of a vessel according to Example 3.

The vessel was a vessel that was commercially manufactured for use as an air receiver with a maximum operating pressure of 1.38 MPa (Silvan Industries, Inc., Marinette, Wis., USA, Part Number A10031). The manufacturer stated that it was designed and built to comply with ASME Code, Section VIII, Div. 1, 20$^{th}$ Edition. As shown in FIG. 22, the vessel was a horizontal, approximately circular cylinder with hemispheroidal "heads" welded to each end of the cylinder. The cylindrical section had a length of 1.34 m, an internal diameter of 0.50 m, and a wall thickness of 3.9 mm. The heads were approximately oblate hemispheroids (that is, half of an ellipse of revolution) with a 0.12 m semi-minor axis and a 3.2 mm wall thickness. We did not modify the vessel for this example.

Seven ports penetrated the vessel's walls. At each port, the manufacturer had welded a threaded fitting to the outside of the vessel. The manufacturer provided threaded caps that matched each port. Before sealing the caps to the ports, we re-tapped all the threads and wrapped the male threads with polytetrafluoroethylene (PTFE) tape. We detected leaks through these threaded seals by painting them with soapy water and looking for bubbles. We reduced the leaks by tightening the seals until bubbles were no longer observed. As shown below, the vessel continued to leak at an average rate $(dM/dt)/M \approx -1.3 \times 10^{-5}$ h$^{-1}$ which corresponds to a bubble rate of approximately 1 mm$^3$/s. This residual appeared to increase slightly during the 3 days of measurements. See FIG. 24, lower-most panel. A month after the data in FIG. 24 were acquired, the leak increased to $-2.4 \times 10^{-5}$ h$^{-1}$.

Materials, Instruments, and Measurements.

We used technical grade argon (molar fraction of argon=99.996%) as the test gas. Also, we used a calibrated thermometer-probe to measure the temperature of the gas $T_{probe}$ at a single point inside the vessel. The probe passed through a hermetic seal in one of the manufacturer's ports and was sensitive to the temperature approximately 1 cm below the top surface of the vessel. Two thermistors were taped to the outside of the vessel and covered with aluminum foil. One thermistor indicated $T_{top}$, the temperature of the metal at one point on the top of the vessel; the second thermistor indicated $T_{bottom}$. The read-out electronics for this thermometer-probe and for both the thermistors were located in an air-conditioned laboratory. The pressure gauge was also located in the laboratory; a tube connected the gauge to a fitting that had been soldered into one of the ports in the vessel. The data in FIG. 24 span the pressure range 426.7 kPa<p<462.7 kPa and the temperature range 20.8° C.<$T_{probe}$<45.3° C.

The acoustic resonances in the gas were driven using a home-made acoustic source and detected using a home-made acoustic detector shown in FIG. 3. These transducers were built into pipe fittings that were screwed into the ports located near the ends of the top surface of the vessel. Because the vessel was unthermostatted and exposed to time-dependent heating by the sun, the drifting resonance frequency could not be determined from a carefully measured resonance line shape. Fortunately, the resonance line shape is unnecessary to detect and quantify a leak from a large vessel. Instead, we tracked the resonance frequency using a computer-controlled PID (proportional-integral-differential) algorithm and the quadrature component of the microphone signal, measured with a lock-in amplifier, as a null detector. The phase of the lock-in was set beforehand so that the quadrature signal was zero at the resonance frequency. The lock-in time constant was 30 ms. Our frequency-tracking method used sophisticated, expensive laboratory instruments, but more economical yet effective methods exist. For example, it should be possible to detect leaks using an acoustic resonance in the gas as the frequency-determining element of an oscillator and measuring the oscillator's frequency (or period) with a counter-timer.

At intervals of 3 s, we measured the frequency of the 2$^{nd}$ longitudinal acoustic resonance of the gas in the vessel $f_{(2,0,0)}$. (We use the subscript (2,0,0) to identify the acoustic resonance of the argon-filled vessel with a corresponding mode of a perfect, closed, right circular cylindrical cavity.) In a perfect cylindrical cavity, the (2,0,0) gas oscillations are parallel to the cylinder's axis and form a standing wave whose pressure nodes and antinodes are planes perpendicular to the axis: an antinode at each end, an antinode midway between the ends, and a node midway between neighboring antinodes. The gas's center of mass does not move during (2,0,0) gas oscillations. The values of $f_{(2,0,0)}$ for our vessel spanned the range 212 Hz<$f_{(2,0,0)}$<221 Hz. The half-width of the (2,0,0) mode was $g_{(2,0,0)}$=0.067 Hz, and the quality factor $Q_{(2,0,0)} \approx 1600$. In our vessel, there were no gas or metal resonance frequencies close enough to $f_{(2,0,0)}$ to interfere with the tracking of $f_{(2,0,0)}$, even while the temperature changed rapidly. The lowest-frequency bending mode of the vessel's metal shell occurs near 272 Hz at 295 K and 450 kPa. At lower pressures, this bending mode might have been so close to $f_{(2,0,0)}$ to cause problems. In another test (not shown here), we obtained essentially the same leak rate from measurements of $f_{(1,0,0)}$ the frequency of the 1$^{st}$ longitudinal mode with 105.8 Hz<$f_{(1,0,0)}$<110.7 Hz and $g_{(1,0,0)}$=0.047 Hz.

Detection of a Leak.

Figure 24:
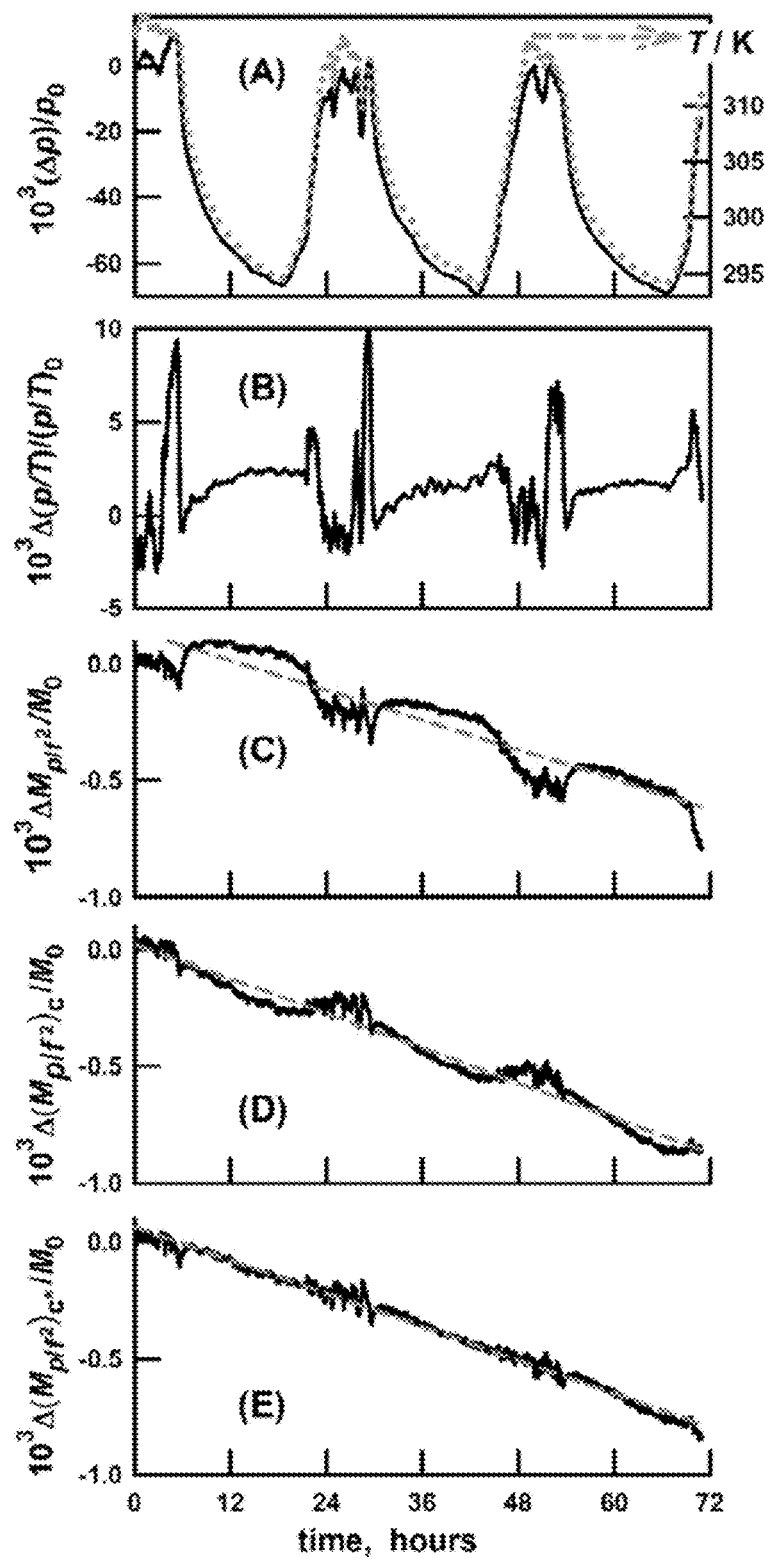
FIG. 24 shows (from top panel to bottom panel) a graph of fractional pressure deviation (solid curve, left-hand y-axis) and temperature (dotted curve, right-hand y-axis) versus time, a graph of fractional deviation of p/T versus time, a graph of fractional deviation of mass M (uncorrected) versus time; a graph of fractional deviation of mass M (corrected for non-ideal gas behavior and thermal expansion of vessel) versus time, and a graph of fractional deviation of mass M (corrected for non-ideal gas behavior and 60% of the thermal expansion used in the graph above) versus time according to Example 3.

FIG. 24 displays the time-dependence of the raw data, together with the results of processing the data using increasingly complex algorithms. The record starts at noon on Jul. 31, 2015 and extends for nearly three days. Top Panel (A) of FIG. 24 displays the fractional pressure deviation from the first pressure measurement (left scale), together with the temperature $T_{probe}$ (right scale). For brevity, we omit the subscript "probe". Each day, between midnight and noon, the pressure and the temperature increased by approximately 8%. Panel (B) of FIG. 24 displays the time dependence of $\Delta(p/T)/(p/T)_0$, where we use the definition $\Delta(p/T) \equiv (p/T) - (p/T)_0$ and the subscript "0" denotes the first measured value of $(p/T)$. The daily variation of $(p/T)$ was only ⅛ of the daily variations of p and of T, however, this variation was still so large that it obscured the leak.

Panel (C) of FIG. 24 displays the time dependence of the ratio $\Delta M/M_0 = \Delta(p/f^2)/(p/f^2)_0$. Here, we omit the subscript (2,0,0) on $f^2$. We use the definition $\Delta(p/f^2) \equiv (p/f^2) - (p/f^2)_0$, where the subscript "0" denotes the first measured value. Note: the vertical scale in Panel (C) is expanded by a factor of 15 compared to the vertical scale in Panel (B). In Panel (C), the slope of the dashed line corresponds to the leak rate $(dM/dt)/M = -1.07 \times 10^{-5}$ h$^{-1}$. The root-mean-square (RMS) deviation of $\Delta M/M_0$ from the dashed line is $\sigma_{RMS} = 7.2 \times 10^{-5}$. These deviations are approximately 0.005× the RMS deviation of p/T from its average value in Panel (B). Thus, replacing $T_{probe}$ with $f^2$ enabled us to detect the leakage of gas out of the vessel, even in the presence of large, sunlight-driven temperature variations.

Panel (D) of FIG. 24 displays the time dependence of the ratio $\Delta M_{p/f_2,c}/M_0$, where the subscript "c" indicates that $(p/f^2)$ is multiplied by the "correction" terms in the square brackets in Eq. 44. The terms account for the thermal expansion of the steel vessel and the $2^{nd}$ virial correction to the ideal-gas equation of state of argon. These corrections increased the apparent leak rate by 16% to $(dM/dt)/M = -1.24 \times 10^{-5}$ h$^{-1}$ and reduced the RMS deviation from a linear fit by a factor of 1.6 to $\sigma_{RMS} = 4.4 \times 10^{-5}$. However, the deviations from the linear fits in Panels (C) and (D) have a daily cycle.

The deviations in Panels (C) and (D) of FIG. 24 suggest that the corrections applied for the thermal expansion and $2^{nd}$ virial coefficient have the correct sign; however, the corrections are too large. In Panel E, we reduced the thermal expansion correction by replacing $\alpha_T(T_{vessel} - T_0)$ with $0.6 \times \alpha_T(T_{vessel} - T_0)$ in Eq. 44. The empirical factor 0.6 eliminated the daily cycle in the deviations from a linear fit and reduced the RMS deviation to a $\sigma_{RMS} = 2.3 \times 10^{-5}$. These improvements might be evidence that the thermal expansion of the vessel was not isotropic, as was assumed in the derivation of Eq. 44. Furthermore, the daily temperature variation averaged over the vessel's steel surface may have been different than the daily temperature variation averaged over the volume of argon within the vessel. In the next section, we speculate about reasons for this.

To summarize, FIG. 24 demonstrated that the ability to detect a leak was improved by a factor of $\approx 8$ by measuring $p/T_{probe}$ instead of measuring p alone. However, the effectiveness can be improved by a factor of $\approx 1000$ by measuring $p/f^2$. In hindsight, we speculate that if the temperature probe were located closer to the center of the vessel, the advantage of measuring $p/T_{probe}$ over measuring $p/f^2$ would be smaller.

Sunshine-Driven Temperature Gradients and Flows.

Convection, or buoyancy-driven flow, results from the fundamental coupling between heat transport and fluid motion in a gravitational field. Natural convection inside a container, resulting from a density gradient generated by uneven heating or cooling of the container wall, encompasses a wide range of complicated flow patterns. A horizontal density gradient, i.e., normal to the gravity vector, immediately leads to convection. A vertical density gradient with the heavier fluid above is unstable and usually leads to convection. A vertical density gradient with the lighter fluid above leads to stable density stratification. Depending on the conditions, a combination of all of these patterns may be present simultaneously. In this section, we describe the thermal environment of the vessel and then try to relate it to some of the results from the literature on convective heat transfer. Our objective is to understand why measuring $p/f^2$ is so effective in detecting a leak and what might limit its effectiveness. The ideas presented in this section are the subject of ongoing and future research.

We used the dimensionless temperature difference [the Rayleigh number: $Ra \equiv \beta g \Delta T a^3/(v\kappa)$] and the dimensionless ratio (viscous diffusivity)/(thermal diffusivity) which is the Prandtl number $Pr \equiv v/\kappa$. Here, $a = 0.5$ m is the radius of the cylinder and the temperature difference is $\Delta T = T_{hot} - T_{cold}$. For our argon-filled vessel (300 K, 0.45 MPa) we estimated $Ra \approx 4 \times 10^8$ ($\Delta T/K$) and $Pr = 0.67$ using the thermophysical properties of argon and the definitions: $\beta \equiv (\partial V/\partial T)_p/V \equiv$ coefficient of volumetric thermal expansion; g =gravitational acceleration; v=kinematic viscosity; and $\kappa \equiv$ thermal diffusivity.

The vessel was placed outside the southern wall of a building (FIG. 22) with its symmetry axis on a north-south line. Before 10 AM, the vessel was shaded by the building on the east (not visible in the photograph); however, the vessel was in direct sunshine from approximately 10 AM to 6 PM. At local solar noon, the temperature difference $T_{top} - T_{bottom}$ was as large as 15 K, where $T_{top}$ and $T_{bottom}$ are the temperatures indicated by thermistors taped to the outside of the vessel. At the same time, $T_{probe} - T_{bottom}$ was as large as 8 K. As one might expect, $T_{top} - T_{probe} \ll T_{probe} - T_{bottom}$. A naïve interpretation of these observations is: the density of the argon increased with depth and might be stably stratified (no convection), even though the Rayleigh number was $\sim 5 \times 10^9$. However, the heating was asymmetric and that probably prevented stratification. Between 10 AM and 6 PM, the southern end of the vessel was heated by the sun while the northern end was not heated. Furthermore, except at local solar noon, one side of the vessel was heated by sunlight more than the opposite side. During each night, the top of the vessel was 0.1 K to 0.5 K cooler than the bottom of the vessel; i.e. the vessel was cooled from the upper surfaces with $4 \times 10^7 < Ra < 2 \times 10^8$. As noted above, the sun heated the vessel from above with an asymmetry that varied throughout the day. At $Ra = 10^6$.

As will be appreciated by one skilled in the art, embodiments herein may be embodied as a system, method or computer program product. Accordingly, embodiments may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, embodiments may take the form of a computer program product embodied in a computer readable medium having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for embodiments herein may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Embodiments are described herein with reference to figures processes, apparatus (systems), and computer program products according. It will be understood that each can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the function or act specified in the description.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The description illustrates an architecture, functionality, and operation of possible implementations of systems, methods, and computer program products according to various embodiments. Such product can be implemented by special purpose hardware-based systems that perform the specified functions or acts, or combinations of special purpose hardware and computer instructions.

Further, a data processing system suitable for storing or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An acousto-microwave system to determine a mass M of gas disposed in a vessel, the acousto-microwave system comprising:

a microwave transmitter disposed on the vessel to transmit microwave radiation inside the vessel, a portion of the microwave radiation occurring at a microwave resonance of the vessel;

a microwave receiver disposed on the vessel to receive microwave radiation communicated through an interior of the vessel from the microwave transmitter;

an acoustic transmitter disposed on the vessel to transmit acoustic radiation inside the vessel, a portion of the acoustic radiation occurring at an acoustic resonance of the gas in the vessel; and an acoustic receiver disposed on the vessel to receive acoustic radiation communicated through the gas from the acoustic transmitter;

a pressure meter to provide a pressure of the gas in the vessel;

a microwave source in electrical communication with the microwave transmitter, the microwave source to provide the microwave radiation to the microwave transmitter prior to the transmission of the microwave radiation inside the vessel;

an acoustic driver in electrical communication with the acoustic transmitter, the acoustic driver to control the acoustic transmitter for production of the acoustic radiation by the acoustic transmitter in response to an acoustic control signal provided to the acoustic transmitter from the acoustic driver; and a processor to receive microwave data from the microwave receiver, acoustic data from the acoustic receiver, temperature data from the pressure meter, the processor to determine the mass M of the gas disposed in the vessel based on the microwave data, acoustic data, and temperature data.

2. The acousto-microwave system of claim 1, wherein the processor determines a volume of the vessel from the microwave data, and determines a speed of sound in the gas from the acoustic data.

3. The acousto-microwave system of claim 2, wherein the mass M of the gas is determined by the processor according to $$M = \rho(p, u)V \approx \frac{\gamma_0 p V}{u^2}\left[1 + (\beta_\alpha - B)\frac{p}{RT}\right],$$

wherein M is the mass of the gas; $\rho$ is the density of the gas; $\gamma_0$ is a zero-pressure heat-capacity ratio that is equal to $C_p/C_v$, wherein $C_p$ is a constant pressure heat capacity of the gas, and $C_v$ is the constant volume heat capacity of the gas; p is the pressure of the gas; V is the volume of the vessel; u is the speed of sound in the gas; $\beta_\alpha$ is an acoustic virial coefficient; B is a density virial coefficient; R is an ideal gas constant; and T is an average temperature of the gas in the vessel.

4. A process for determining a mass M of a gas disposed in a vessel, the process comprising:

subjecting an interior of the vessel with microwave radiation transmitted by a microwave transmitter disposed on the vessel, a portion of the microwave radiation occurring at a microwave resonance of the vessel;

communicating the microwave radiation through an interior of the vessel;

receiving, by a microwave receiver disposed on the vessel, the microwave radiation communicated through the interior of the vessel;

transmitting, by an acoustic transmitter disposed on the vessel, acoustic radiation;

subjecting the gas disposed in the vessel with the acoustic radiation transmitted by the acoustic transmitter, a portion of the acoustic radiation occurring at an acoustic resonance of the gas in the vessel;

communicating the acoustic radiation through the gas disposed in the vessel;

receiving, by an acoustic receiver disposed on the vessel, the acoustic radiation communicated through the gas disposed in the vessel; and analyzing the microwave radiation received by the microwave receiver and the acoustic radiation received by the acoustic receiver to determine the mass M of the gas disposed in the vessel.

5. The process of claim 4, further comprising determining a pressure of the gas disposed in the vessel.

6. The process of claim 5, wherein determining the pressure of the gas disposed in the vessel comprises acquiring a pressure signal from a pressure meter disposed on the vessel.

7. The process of claim 6, wherein analyzing the microwave radiation comprises:

determining a microwave frequency of a microwave resonance of the vessel based on the microwave radiation received by the microwave receiver;

determining an acoustic frequency of an acoustic resonance of the gas based on the acoustic radiation received by the acoustic receiver; and combining the pressure of the gas, the microwave frequency of the microwave resonance of the vessel, and the acoustic frequency of the acoustic resonance of the gas to determine the mass of the gas disposed in the vessel.

8. The process of claim 7, further comprising determining a volume of the vessel from the microwave frequency of the microwave resonance of the vessel.

9. The process of claim 8, wherein determining the volume of the vessel comprises:

providing a model shape of the vessel;

providing a plurality of model geometric parameters of the vessel;

computing a model microwave resonance of the vessel based on the model shape and the model geometric parameters;

fitting the microwave resonance and the model microwave resonance;

adjusting the model geometric parameters to obtain a best fit of the microwave resonance and the model microwave resonance; and determining the volume of the vessel from the geometric parameters used to obtain the best fit.

10. The process of claim 9, further comprising determining an average temperature of the gas in the vessel from the acoustic frequency of the acoustic resonance of the gas in the vessel.

11. The process of claim 10, wherein determining the average temperature of the gas comprises determining a speed of sound in the gas from the acoustic frequency of the acoustic resonance of the gas in the vessel.

12. The process of claim 11, further comprising determining a density of the gas in the vessel from an equation of state of the gas, wherein the mass M of the gas is determined according to $$M = \rho(p, u)V \approx \frac{\gamma_0 pV}{u^2}\left[1 + (\beta_\alpha - B)\frac{p}{RT}\right],$$

wherein M is the mass of the gas; $\rho$ is the density of the gas; $\gamma_0$ is a zero-pressure heat-capacity ratio that is equal to $C_p/C_v$, wherein $C_p$ is a constant pressure heat capacity of the gas, and $C_v$ is the constant volume heat capacity of the gas; p is the pressure of the gas; V is the volume of the vessel; u is the speed of sound in the gas; $\beta_\alpha$ is an acoustic virial coefficient; B is a density virial coefficient; R is an ideal gas constant; and T is an average temperature of the gas in the vessel.

13. A process for detecting a leak of a gas disposed in a vessel, the process comprising:
determining a pressure p of the gas disposed in the vessel;
transmitting, by an acoustic transmitter disposed on the vessel, acoustic radiation inside the vessel;
subjecting the gas in the vessel to acoustic radiation;
receiving, by an acoustic receiver disposed on the vessel, acoustic radiation communicated through the gas from the acoustic transmitter;
determining an acoustic frequency of an acoustic resonance $f_a$ of the gas based on the acoustic radiation received by the acoustic receiver; and
combining the pressure of the gas and the acoustic frequency of the acoustic resonance $f_a$ of the gas to detect the leak of the gas disposed in the vessel according to a decrease in $p/(f_a)^2$.

14. The process of claim 13, further comprising:
subjecting an interior of the vessel with microwave radiation transmitted by a microwave transmitter disposed on the vessel, a portion of the microwave radiation occurring at a microwave resonance of the vessel;
communicating the microwave radiation through an interior of the vessel;
receiving, by a microwave receiver disposed on the vessel, the microwave radiation communicated through the interior of the vessel; and
determining a microwave frequency of a microwave resonance $f_m$ of the vessel based on the microwave radiation received by the microwave receiver; and
determining a volume of the vessel from the microwave frequency of the microwave resonance $f_m$ of the vessel.

15. The process of claim 14, wherein determining the volume of the vessel comprises:
providing a model shape of the vessel;
providing a plurality of model geometric parameters of the vessel;
computing a model microwave frequency of the microwave resonance of the vessel based on the model shape and the model geometric parameters;
fitting the microwave resonance and the model microwave frequency;
adjusting the model geometric parameters to obtain a best fit of the microwave resonance and the model microwave frequency; and
determining the volume of the vessel from the geometric parameters used to obtain the best fit.

16. The process of claim 15, further comprising:
determining an average temperature of the gas in the vessel from the acoustic frequency of the acoustic resonance $f_a$ of the gas in the vessel; and
determining a mass M of the gas in the vessel according to $$M = \rho(p, u)V \approx \frac{\gamma_0 pV}{u^2}\left[1 + (\beta_\alpha - B)\frac{p}{RT}\right],$$

wherein M is the mass of the gas; $\rho$ is the density of the gas; $\gamma_0$ is a zero-pressure heat-capacity ratio that is equal to $C_p/C_v$, wherein $C_p$ is a constant pressure heat capacity of the gas, and $C_v$ is the constant volume heat capacity of the gas; p is the pressure of the gas; V is the volume of the vessel; u is the speed of sound in the gas; $\beta_\alpha$ is an acoustic virial coefficient; B is a density virial coefficient; R is an ideal gas constant; and T is an average temperature of the gas in the vessel.

\* \* \* \* \*